US009115112B2

(12) United States Patent
Hong et al.

(10) Patent No.: US 9,115,112 B2
(45) Date of Patent: *Aug. 25, 2015

(54) AMINOANTHRACENE DERIVATIVE AND AN ORGANIC ELECTROLUMINESCENT ELEMENT EMPLOYING THE SAME

(75) Inventors: Jin-Seok Hong, Suwon-si (KR); Kyoung-Soo Kim, Yuseong-gu (KR); Tae-Hyung Kim, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 575 days.

This patent is subject to a terminal disclaimer.

(21) Appl. No.: 13/378,781

(22) PCT Filed: Jun. 1, 2010

(86) PCT No.: PCT/KR2010/003521

§ 371 (c)(1), (2), (4) Date: Mar. 6, 2012

(87) PCT Pub. No.: WO2010/147318

PCT Pub. Date: Dec. 23, 2010

(65) Prior Publication Data

US 2012/0161615 A1 Jun. 28, 2012

(30) Foreign Application Priority Data

Jun. 19, 2009 (KR) ........................ 10-2009-0054903

(51) Int. Cl.

*H01L 51/50* (2006.01)
*C07C 211/61* (2006.01)
*C07D 333/34* (2006.01)
*C07D 213/74* (2006.01)
*C07D 241/20* (2006.01)
*C09K 11/06* (2006.01)
*H01L 51/00* (2006.01)

(52) U.S. Cl.

CPC ............ *C07D 333/34* (2013.01); *C07D 213/74* (2013.01); *C07D 241/20* (2013.01); *C09K 11/06* (2013.01); *H01L 51/006* (2013.01); *H01L 51/0055* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1092* (2013.01); *H01L 51/5012* (2013.01)

(58) Field of Classification Search

CPC .. C07D 213/74; C07D 241/20; C07D 333/34; C09K 11/06; C09K 2211/1011; C09K 2211/1029; C09K 2211/1044; C09K 2211/1092; C09K 2211/1007; H01L 51/0055; H01L 51/006; H01L 51/5012

See application file for complete search history.

(56) References Cited

U.S. PATENT DOCUMENTS

| | | | | |
|---|---|---|---|---|
| 8,395,144 B2 * | 3/2013 | Lee et al. | ........................ | 257/40 |
| 8,525,158 B2 * | 9/2013 | Shin et al. | ........................ | 257/40 |
| 2007/0278938 A1 | 12/2007 | Yabunouchi et al. | | |
| 2008/0315754 A1 | 12/2008 | Kawamura et al. | | |
| 2012/0286246 A1 * | 11/2012 | Kim et al. | ........................ | 257/40 |
| 2012/0286249 A1 * | 11/2012 | Lee et al. | ........................ | 257/40 |

FOREIGN PATENT DOCUMENTS

| | | | |
|---|---|---|---|
| JP | 2010-238924 | A | 10/2010 |
| JP | 2012-510154 | A | 4/2012 |
| JP | 2012-510988 | A | 5/2012 |
| KR | 10-2008-0080306 | A | 9/2008 |
| KR | 10-2008-0112325 | A | 12/2008 |
| WO | 2007/069569 | A1 | 6/2007 |
| WO | 2007/125714 | A1 | 11/2007 |
| WO | WO 2010/062107 | * | 6/2010 |
| WO | WO 2010/064871 | * | 6/2010 |
| WO | WO 2010/150988 | * | 12/2010 |

OTHER PUBLICATIONS

Japanese Patent Office, Communication dated Mar. 18, 2014, issued in the corresponding Japanese Patent Application No. 2012-515965.

* cited by examiner

*Primary Examiner* — Dawn Garrett
(74) *Attorney, Agent, or Firm* — Sughrue Mion, PLLC

(57) ABSTRACT

Disclosed are a novel amino anthracene derivative and an organic electro-luminescence device using the same. More specifically, the disclosed amino anthracene derivative has a core (e.g., indenoanthracene core) of an anthracene moiety (with a high device characteristic) linked to a fluorene moiety (with a high fluorescence characteristic), in which in the core is substituted with at least one amine group represented by Formula 2 and the disclosed organic electro-luminescence device uses the amino anthracene derivative as a light emitting layer material so as to be enhanced in efficiency, operating voltage, and life span.

5 Claims, No Drawings

AMINOANTHRACENE DERIVATIVE AND AN ORGANIC ELECTROLUMINESCENT ELEMENT EMPLOYING THE SAME

TECHNICAL FIELD

The present invention relates to a novel anthracene derivative, and an organic electro-luminescence device using the novel anthracene derivative as a light emitting layer material, in which the device is enhanced in efficiency, operating voltage, and life span.

BACKGROUND ART

In general, an organic light emitting phenomenon indicates conversion of electric energy into light energy by means of an organic material. An organic electro-luminescence device using the organic light emitting phenomenon generally has a structure including an anode, a cathode, and an organic material layer interposed therebetween. Herein, in many cases, the organic material layer may have a multi-layered structure having respective different materials in order to improve efficiency and stability of an organic light emitting device. For example, it may include a hole injection layer, a hole transport layer, a light emitting layer, an electron transport layer, an electron injection layer, and the like.

When such an organic electro-luminescence device is applied with a forward voltage, holes and electrons are injected from an anode and a cathode, respectively. Then, the holes and the electrons recombine in a light emitting layer, thereby forming excitons (electron-hole pairs). When the excitons are converted from an excited state of pi-electrons per molecule to a ground state, the corresponding energy is converted into light. In order to enhance the color purity and efficiency of emitted light, there has been recently known a method for doping a small amount of a fluorescent or phosphorescent pigment into the light emitting layer forming excitons. The method is based on the principle that if a small amount of a fluorescent or phosphorescent pigment (hereinafter, referred to as a dopant) having a smaller energy band gap than molecules forming a light emitting layer is mixed with the light emitting layer, excitons which are generated in the light emitting layer are transported to the dopant, thus emitting a light having a high efficiency.

Various materials emitting green light, such as 8-hydroquinoline aluminum salt, have been conventionally used as a host. However, there are some problems to be improved in view of luminous efficiency and life span.

Technical Problem

Therefore, the present invention has been made in view of the above-mentioned problems, and the present invention provides a novel light emitting material and an organic electro-luminescence device using the same, in which the device is enhanced in luminous efficiency, and brightness, and can be operated at a low voltage.

Technical Solution

In accordance with an aspect of the present invention, there is provided a compound represented by Formula 1 below.

(Formula 1)

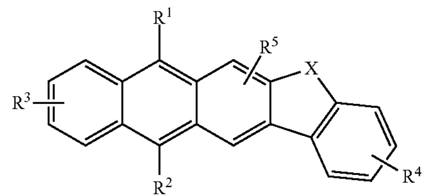

In Formula 1, X is selected from the group consisting of $CR^6R^7$, $NR^6$, O, S, S(=O), $S(=O)_2$ and $SiR^6R^7$, $R^1$ to $R^7$ are the same or different, and each is independently selected from the group consisting of hydrogen, deuterium, an alkyl group of $C_1$~$C_{40}$, an alkenyl group of $C_2$~$C_{40}$, an alkynyl group of $C_2$~$C_{40}$, an aryl group of $C_5$~$C_{40}$, a heteroaryl group of $C_5$~$C_{40}$, an aryloxy group of $C_5$~$C_{40}$, an alkyloxy group of $C_1$~$C_{40}$, an arylalkyl group of $C_6$~$C_{40}$, a cycloalkyl group of $C_3$~$C_{40}$, a heterocycloalkyl group of $C_3$~$C_{40}$ and a substituent represented by Formula 2 below; or a group binding with an adjacent group to form a fused aliphatic ring, a fused aromatic ring, a fused heteroaliphatic ring or a fused heteroaromatic ring;

wherein, at least one of $R^1$ to $R^4$ is a substituent represented by Formula 2 below,

[Formula 2]

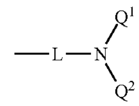

In Formula 2, $Q^1$ and $Q^2$ are the same or different, and each is independently selected from the group consisting of hydrogen, deuterium, an alkyl group of $C_1$~$C_{40}$, an alkenyl group of $C_2$~$C_{40}$, an alkynyl group of $C_2$~$C_{40}$, an aryl group of $C_5$~$C_{40}$, a heteroaryl group of $C_5$~$C_{40}$, an aryloxy group of $C_5$~$C_{40}$, an alkyloxy group of $C_1$~$C_{40}$, an arylalkyl group of $C_6$~$C_{40}$, a cycloalkyl group of $C_3$~$C_{40}$, and a heterocycloalkyl group of $C_3$~$C_{40}$; or a group binding with an adjacent group to form a fused aliphatic ring, a fused aromatic ring, a fused heteroaliphatic ring or a fused heteroaromatic ring;

L is selected from the group consisting of a single bond, an alkylene group of $C_1$~$C_{40}$, an alkenylene group of $C_2$~$C_{40}$, an alkynylene group of $C_2$~$C_{40}$, an arylene group of $C_5$~$C_{40}$, a heteroarylene group of $C_5$~$C_{40}$, an aryloxy group of $C_5$~$C_{40}$, an alkyloxy group of $C_1$~$C_{40}$, an arylalkylene group of $C_6$~$C_{40}$, a cycloalkylene group of $C_3$~$C_{40}$, and a heterocycloalkylene group of $C_3$~$C_{40}$.

According to another aspect of the present invention, there is provided an organic electro-luminescence device including an (i) anode, (ii) a cathode, and (iii) one or more organic material layers intervened between the anode and the cathode, wherein at least one layer of the organic material layers includes the compound represented by Formula 1 according to the present invention.

In the organic electro-luminescence device, the organic material layer including the compound represented by Formula 1 is preferably a light emitting layer.

Advantageous Effects

When employed as a light emitting layer material for an organic electro-luminescence device, the inventive compound represented by Formula 1 is excellent in luminous efficiency, brightness, power efficiency, operating voltage, and life span. Accordingly, it is possible to achieve a remarkable effect on performance maximization and life span improvement in a full-color organic EL panel.

BEST MODE

The inventive compound represented by Formula 1 is an amino anthracene derivative having a core (e.g., indenoanthracene core) of an anthracene moiety (with a high device characteristic) linked to a fluorene moiety (with a high fluorescence characteristic), in which the core is substituted with at least one amine group represented by Formula 2.

The inventive compound represented by Formula 1 is a material having a light-emitting capability, and preferably is a green or orange light-emitting capability.

In the inventive compound, in $R^1$ to $R^7$, and $Q^1$ and $Q^2$, the alkyl group of $C_1$~$C_{40}$, the alkenyl group of $C_2$~$C_{40}$, the alkynyl group of $C_2$~$C_{40}$, the aryl group of $C_5$~$C_{40}$, the heteroaryl group of $C_5$~$C_{40}$, the aryloxy group of $C_5$~$C_{40}$, the alkyloxy group of $C_1$~$C_{40}$, the arylamino group of $C_5$~$C_{40}$, the diarylamino group of $C_5$~$C_{40}$, the arylalkyl group of $C_6$~$C_{40}$, the cycloalkyl group of $C_3$~$C_{40}$, and the heterocycloalkyl group of $C_3$~$C_{40}$ are each independently unsubstituted or substituted by at least one substituent selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$, and a heteroaryl group of $C_5$~$C_{40}$.

Also, among the substituents that can be introduced at the alkyl group of $C_1$~$C_{40}$, the alkenyl group of $C_2$~$C_{40}$, the alkynyl group of $C_2$~$C_{40}$, the aryl group of $C_5$~$C_{40}$, the heteroaryl group of $C_5$~$C_{40}$, the aryloxy group of $C_5$~$C_{40}$, the alkyloxy group of $C_1$~$C_{40}$, the arylamino group of $C_5$~$C_{40}$, the diarylamino group of $C_5$~$C_{40}$, the arylalkyl group of $C_6$~$C_{40}$, the cycloalkyl group of $C_3$~$C_{40}$, and the heterocycloalkyl group of $C_3$~$C_{40}$ in $R^1$ to $R^7$, and $Q^1$ and $Q^2$, the alkyl group of $C_1$~$C_{40}$, the alkenyl group of $C_2$~$C_{40}$, the alkoxy group of $C_1$~$C_{40}$, the amino group of $C_1$~$C_{40}$, the cycloalkyl group of $C_3$~$C_{40}$, the heterocycloalkyl group of $C_3$~$C_{40}$, the aryl group of $C_6$~$C_{40}$, and the heteroaryl group of $C_5$~$C_{40}$, may be each independently further substituted by at least one substituent selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$, and a heteroaryl group of $C_5$~$C_{40}$; or may bind with an adjacent group to form a fused aliphatic ring, a fused aromatic ring, a fused heteroaliphatic ring, a fused heteroaromatic ring, or a spiro bond.

Examples of the compound represented by Formula 1 of the present invention include the following compounds represented by Formula 3, but the compound represented by Formula 1 of the present invention is not limited thereto.

[Formula 3]

Inv-1-1

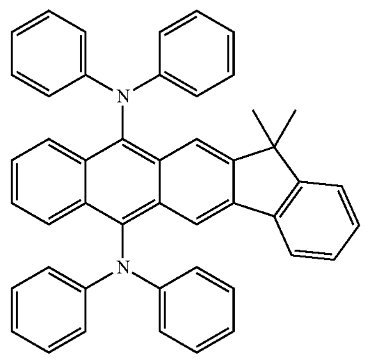

Inv-1-2

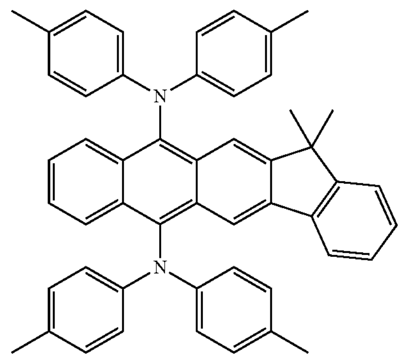

Inv-1-3

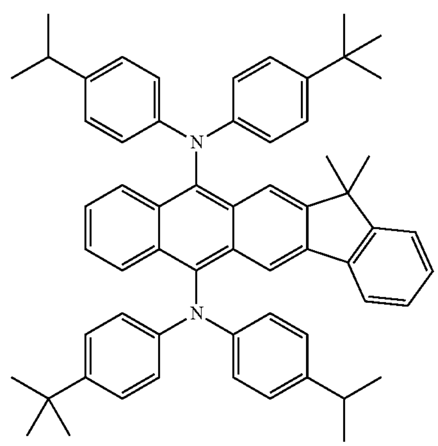

Inv-1-4

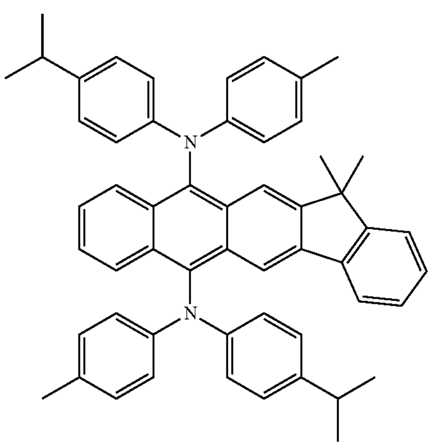

-continued
Inv-1-5
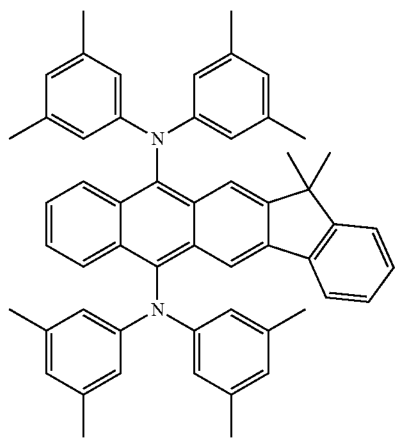
Inv-1-6
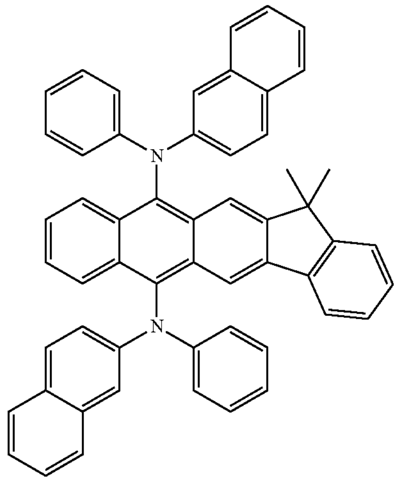
Inv-1-7
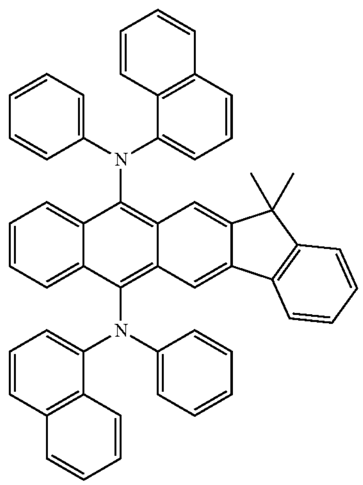
Inv-1-8
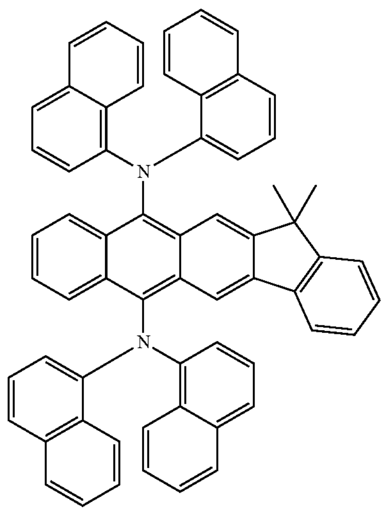
Inv-1-9
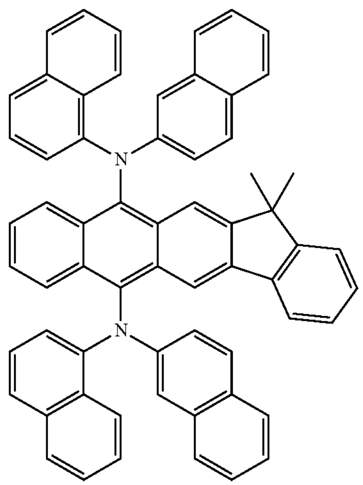
Inv-1-10
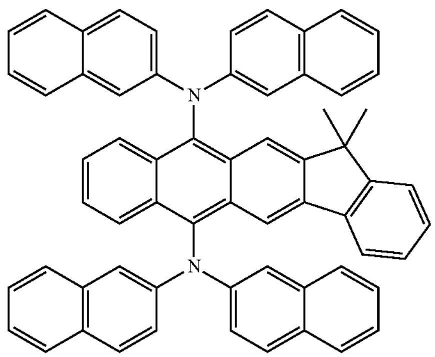

-continued
Inv-1-11
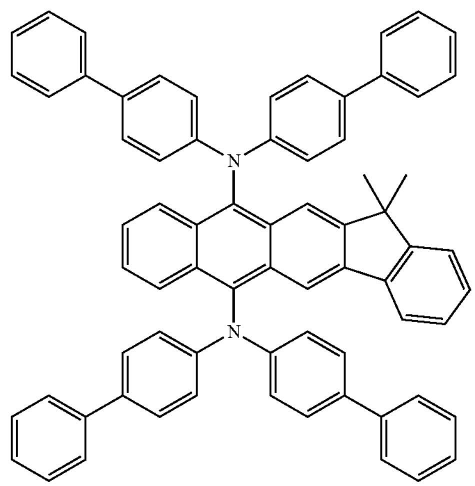
Inv-1-12
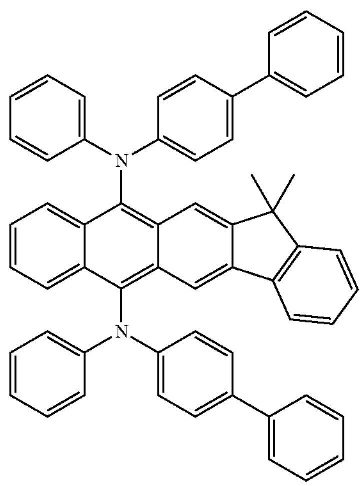
Inv-1-13
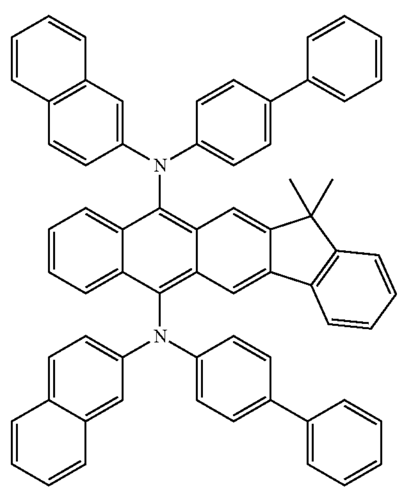
Inv-1-14
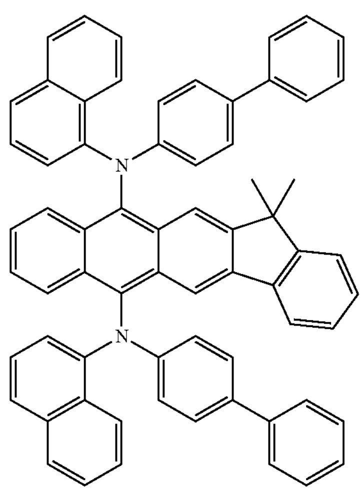
Inv-1-15
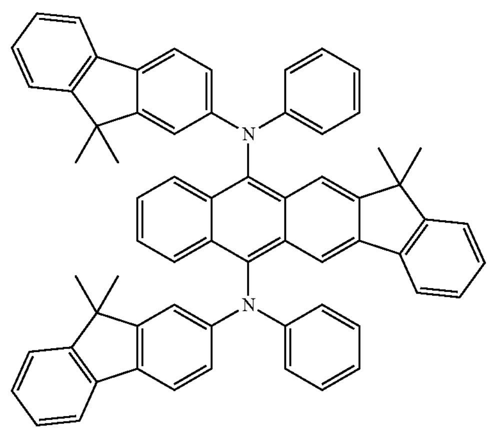
Inv-1-16
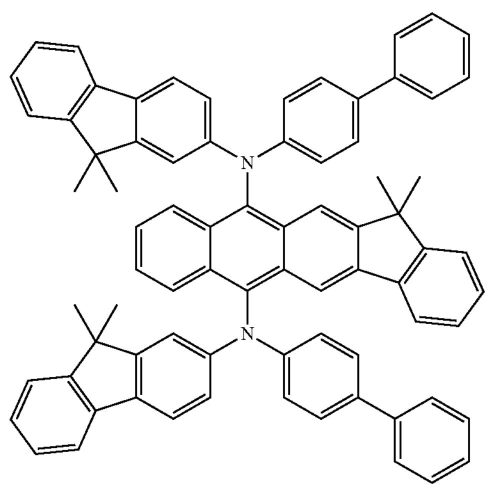

-continued
Inv-1-17
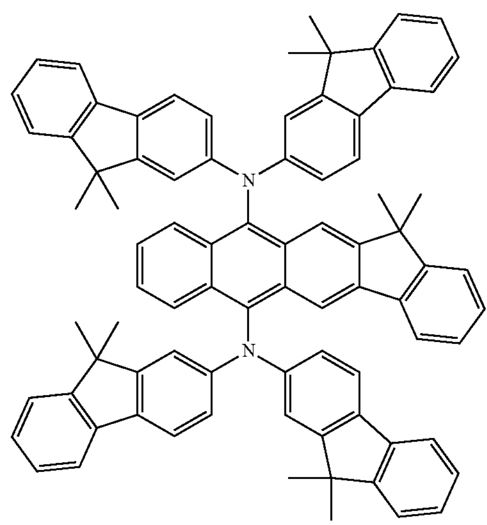
Inv-1-18
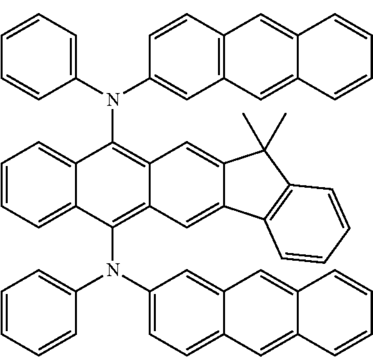
Inv-1-19
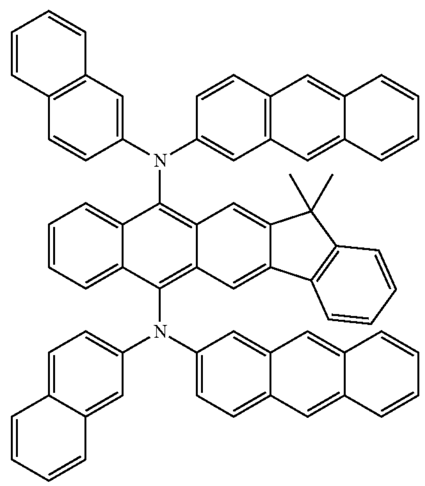
Inv-1-20
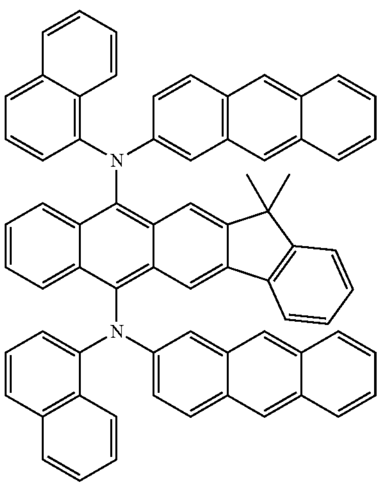
Inv-1-21
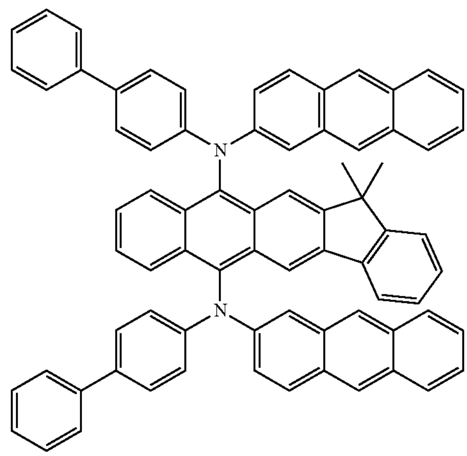
Inv-1-22
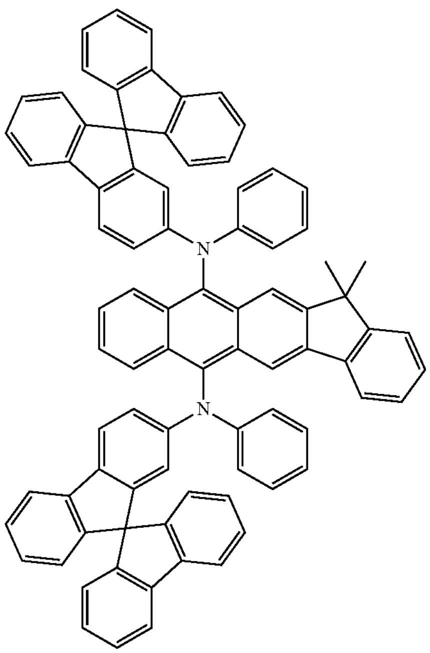

-continued
Inv-1-23
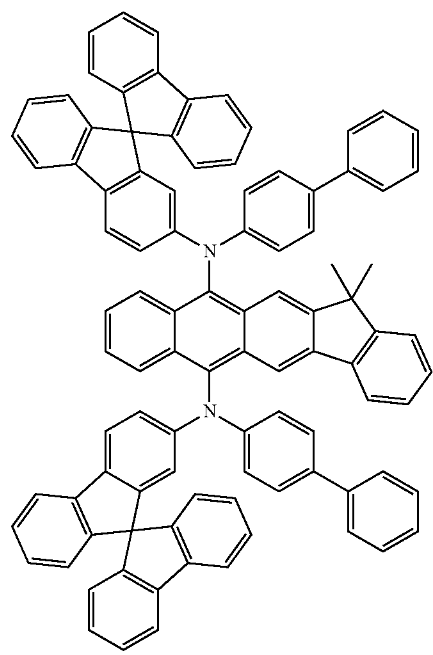
Inv-1-24
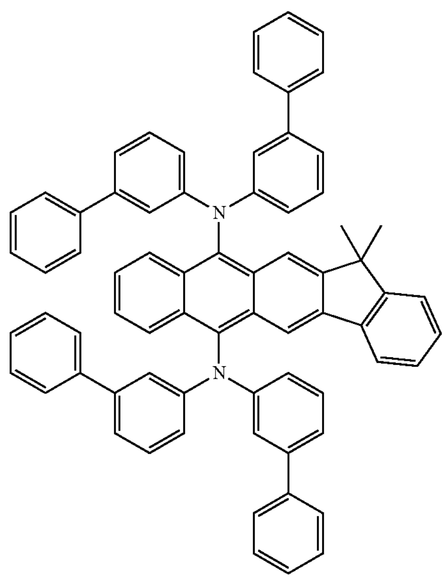
Inv-1-25
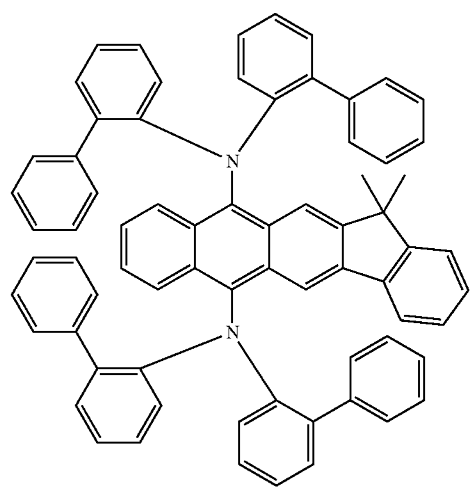
Inv-1-26
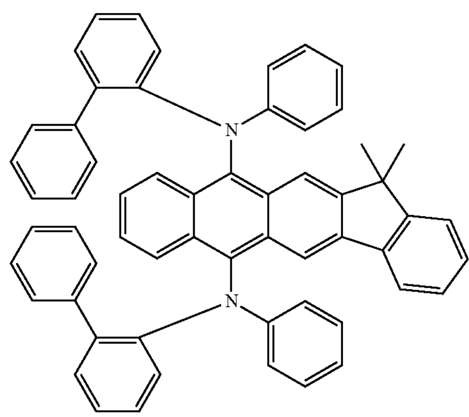
Inv-1-27
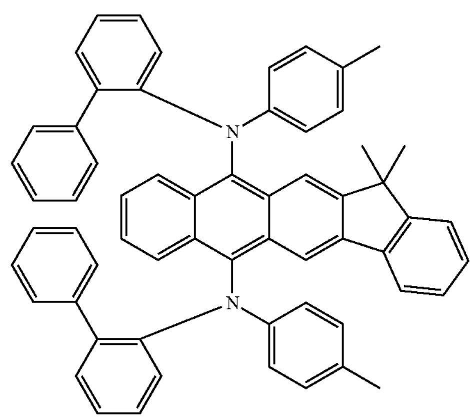
Inv-1-28
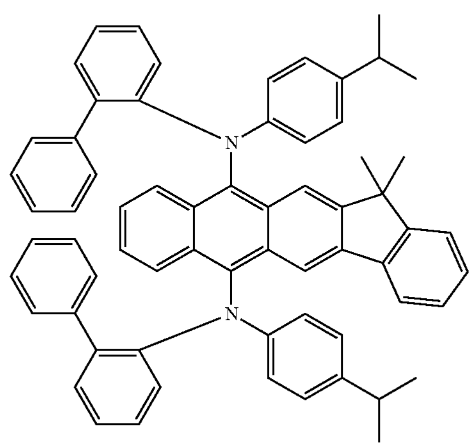

-continued
Inv-1-29
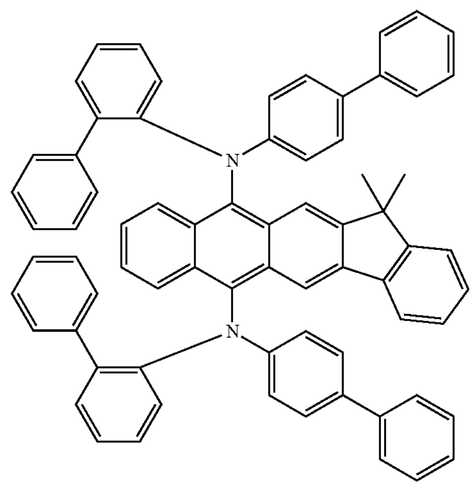
Inv-1-30
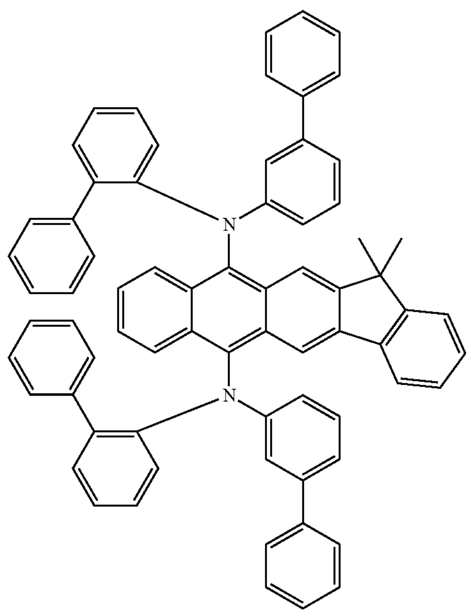
Inv-1-31
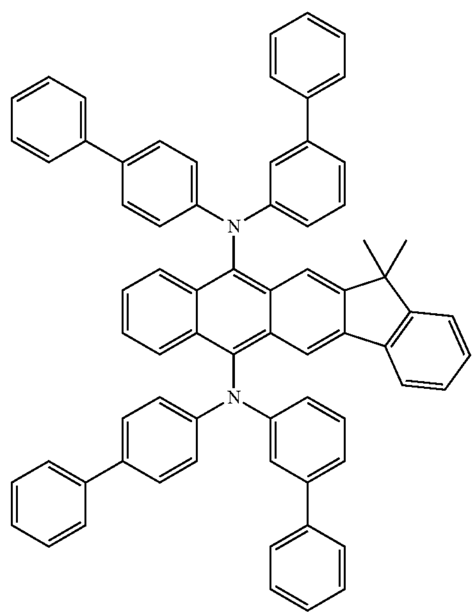
Inv-1-32
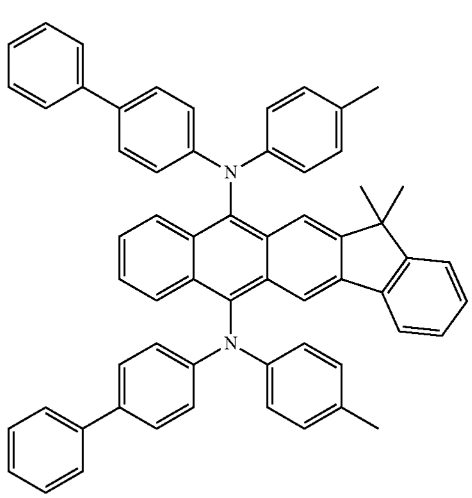
Inv-1-33
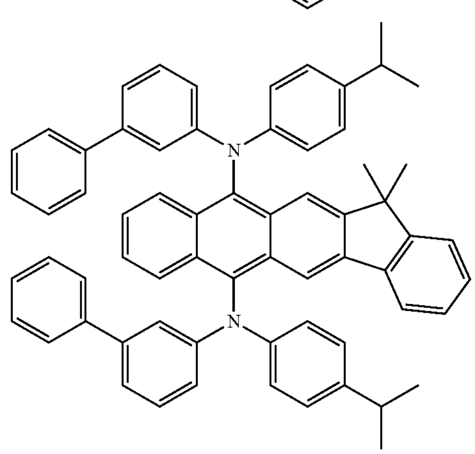
Inv-1-34

-continued
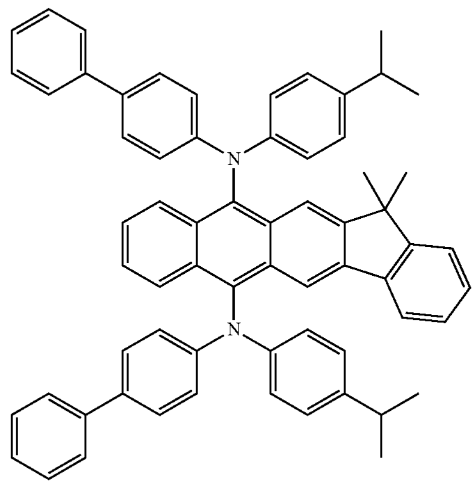
Inv-1-35
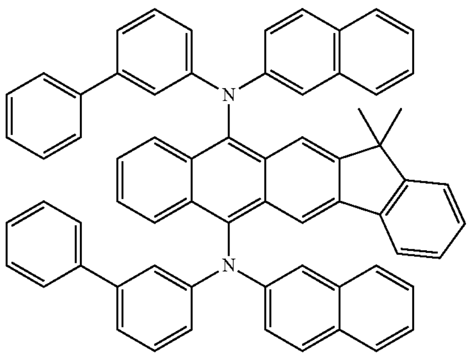
Inv-1-36
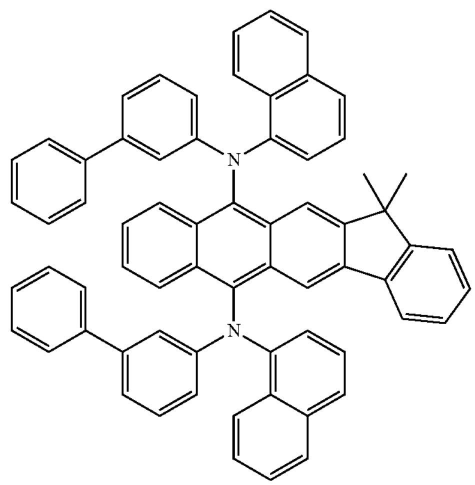
Inv-1-37
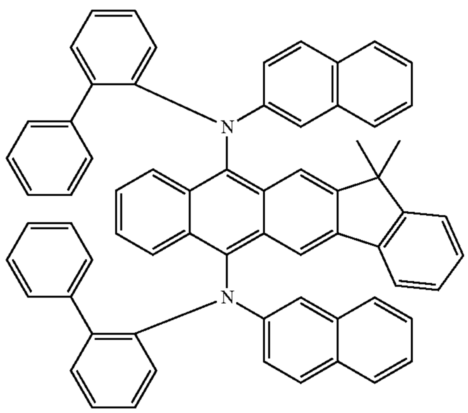
Inv-1-38
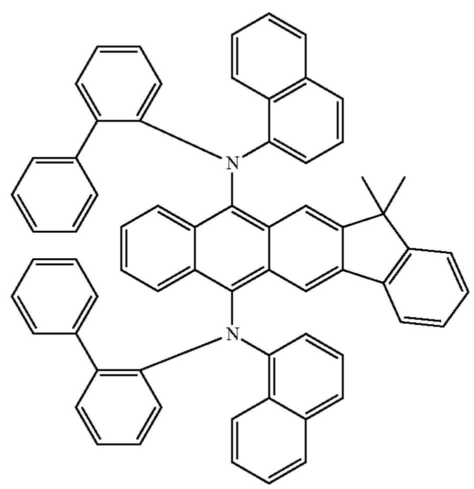
Inv-1-39
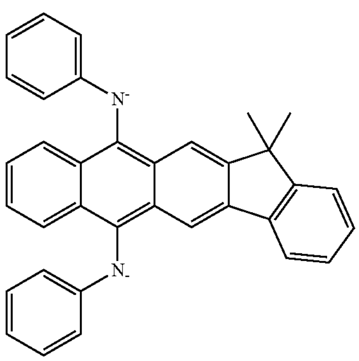
Inv-1-40

-continued
Inv-1-41
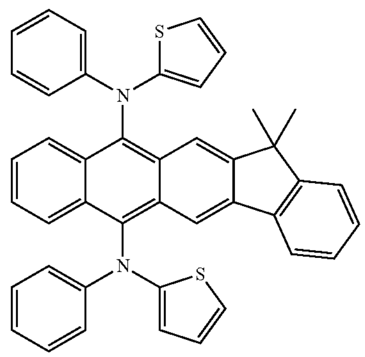
Inv-1-42
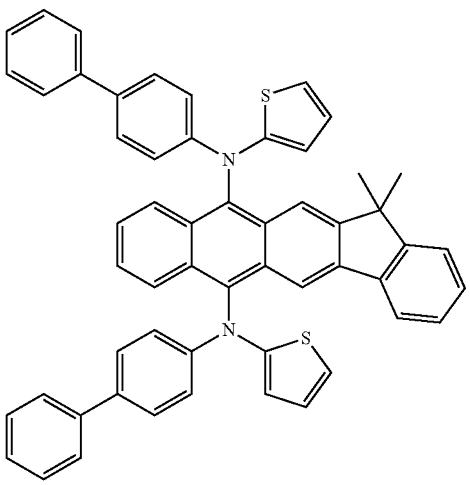
Inv-1-43
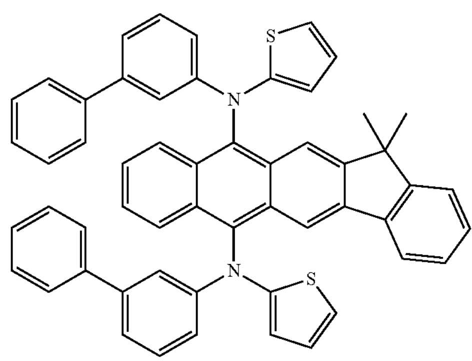
Inv-1-44
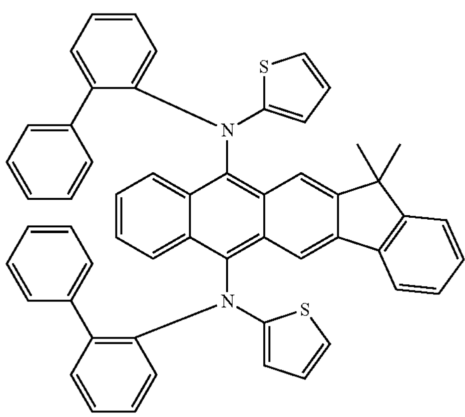
Inv-1-45
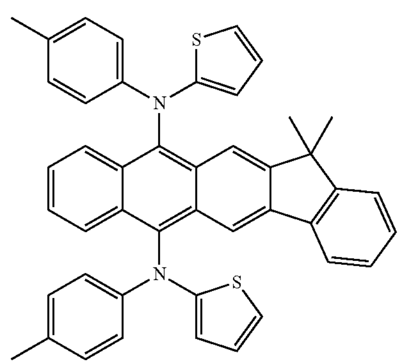
Inv-1-46
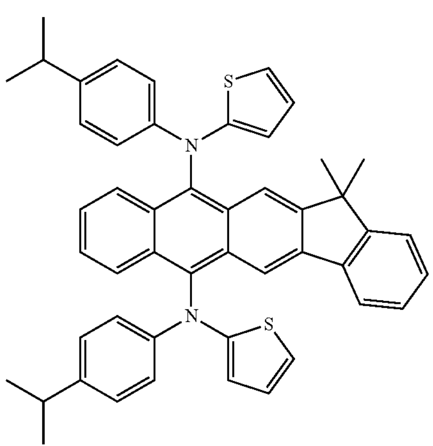

-continued
Inv-1-47
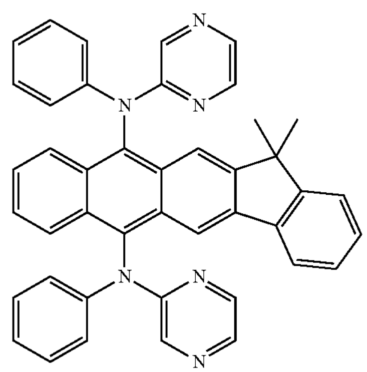
Inv-1-48
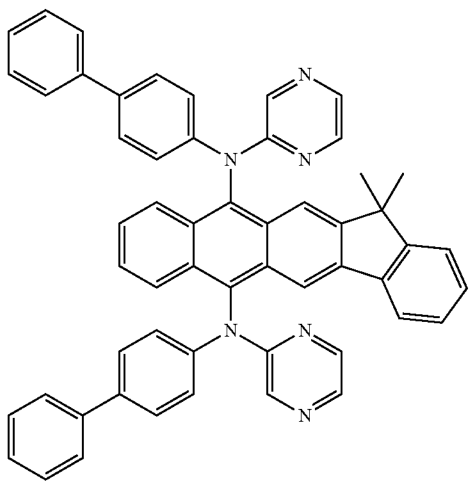
Inv-1-49
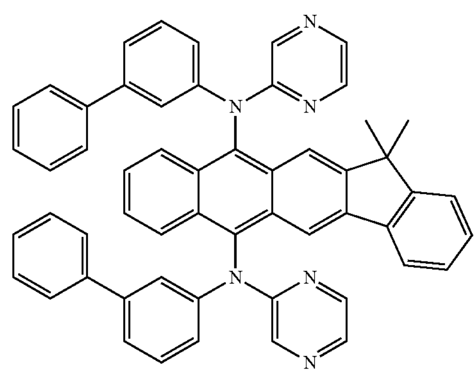
Inv-1-50
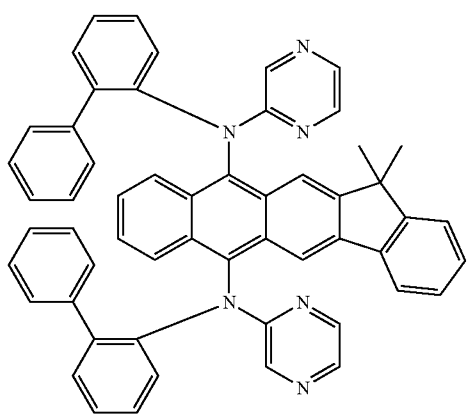
Inv-1-51
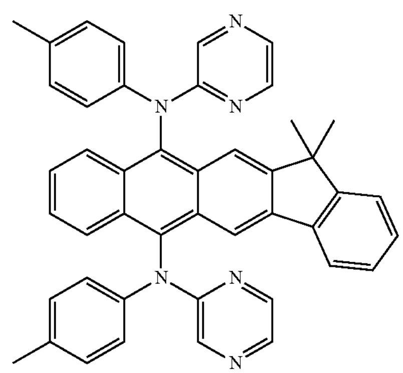
Inv-1-52
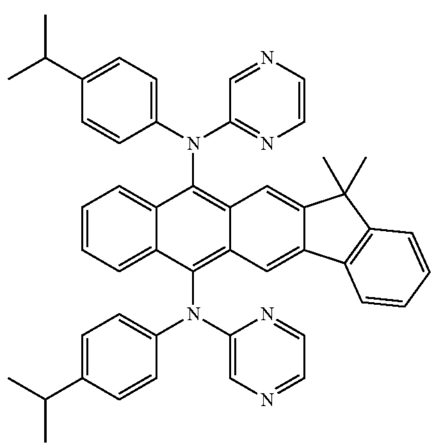

-continued
Inv-1-53
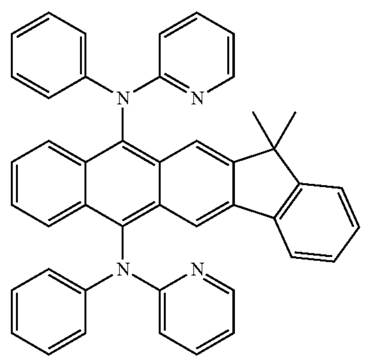
Inv-1-54
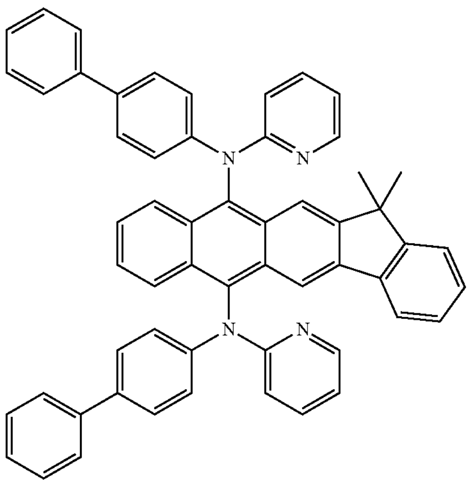
Inv-1-55
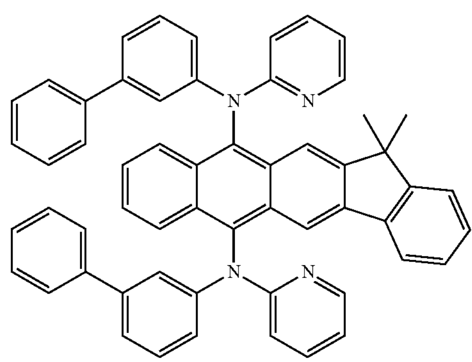
Inv-1-56
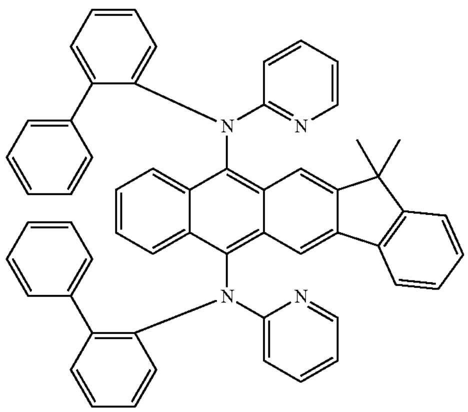
Inv-1-57
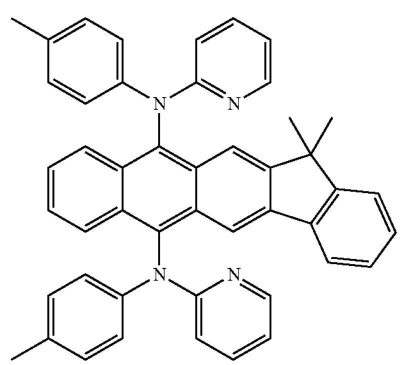
Inv-1-58
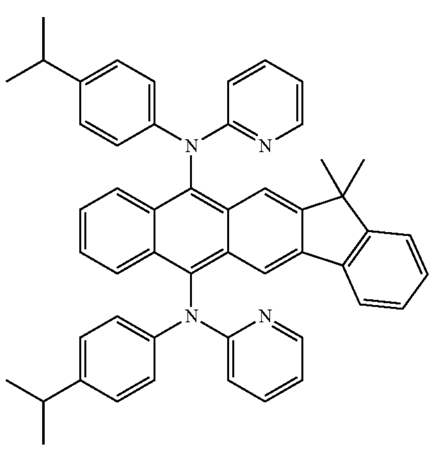

-continued
Inv-1-59
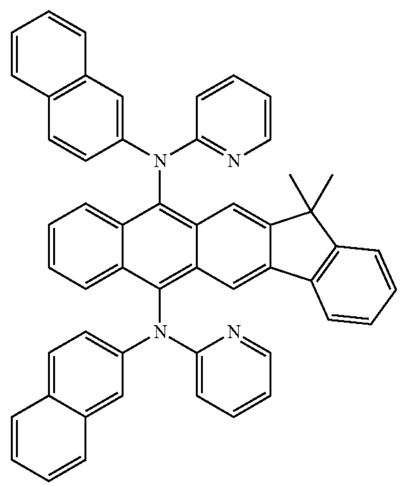
Inv-1-60
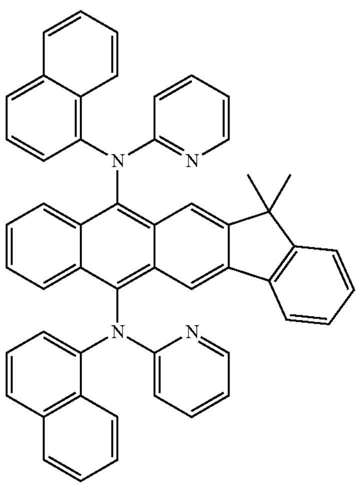
Inv-1-61
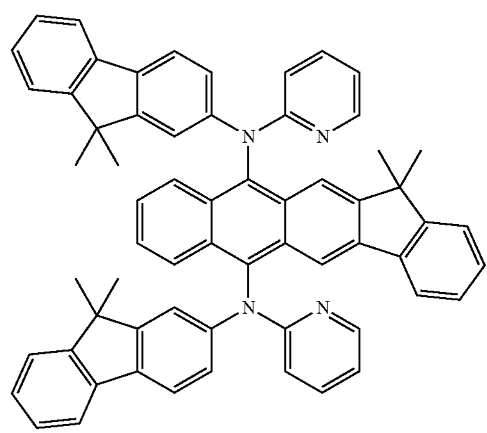
Inv-1-62
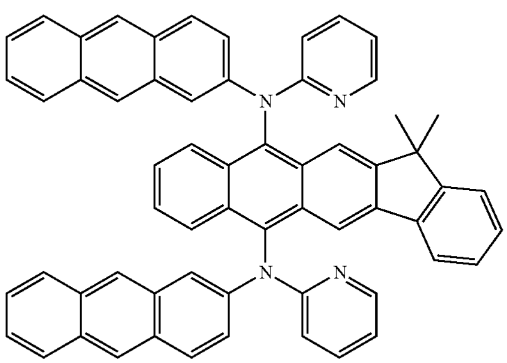
Inv-1-63
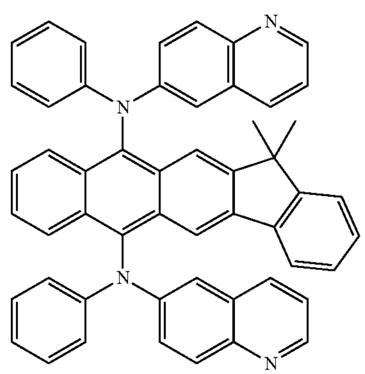
Inv-1-64
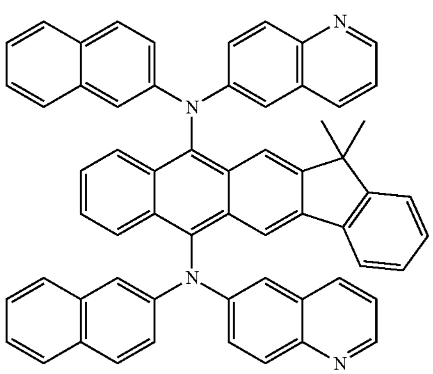

-continued
Inv-1-65
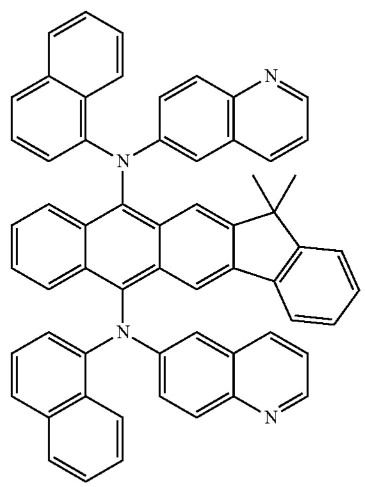
Inv-1-66
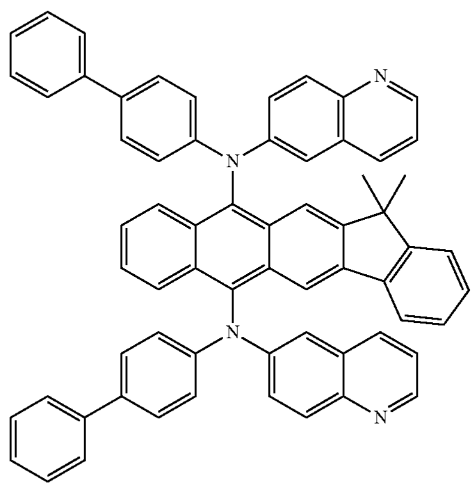
Inv-1-67
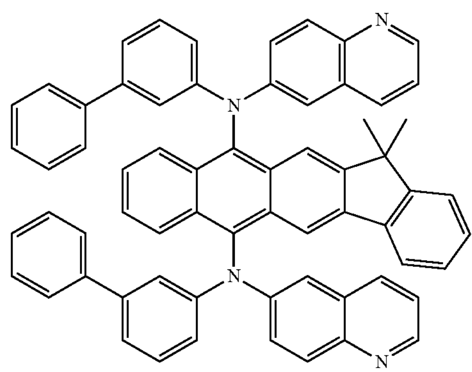
Inv-1-68
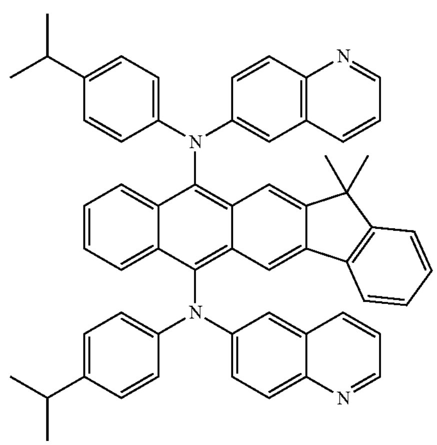
Inv-1-69
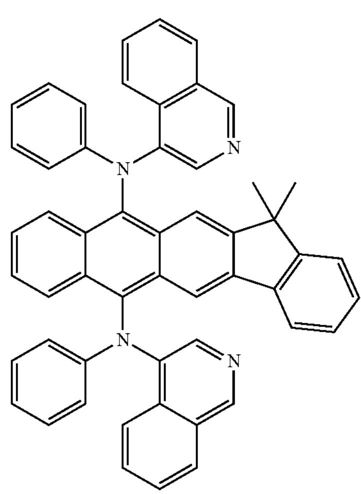
Inv-1-70
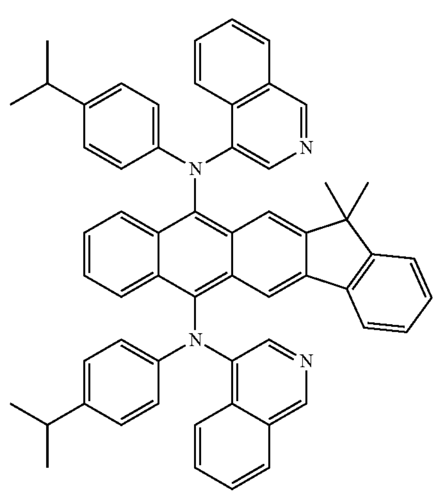

-continued
Inv-1-71
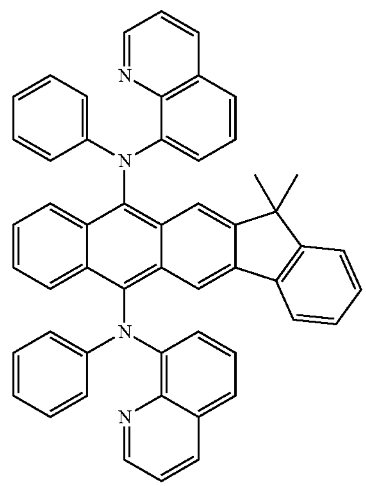
Inv-1-72
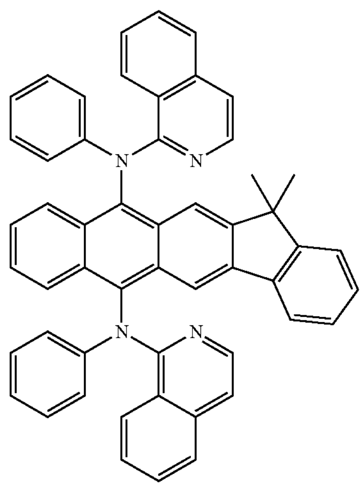
Inv-1-73
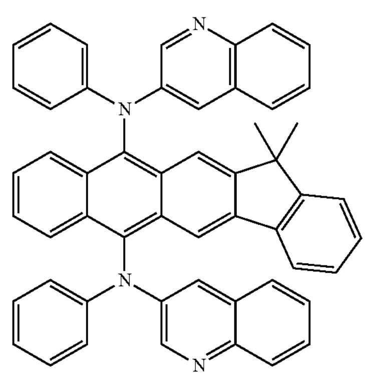
Inv-1-74
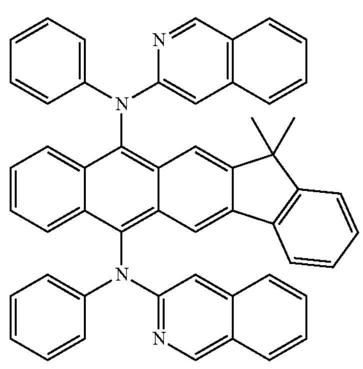
Inv-1-75
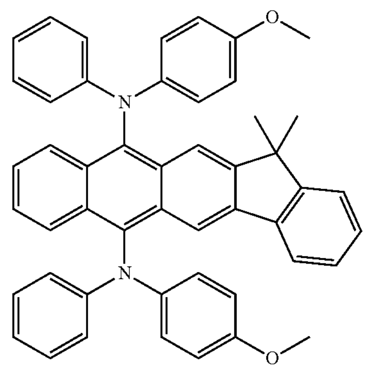
Inv-1-76
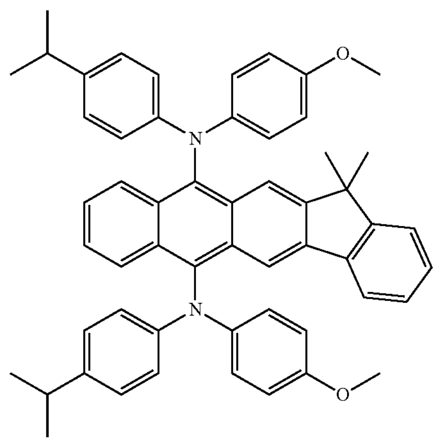

-continued
Inv-1-77
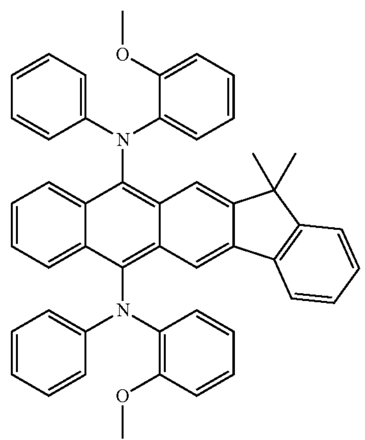
Inv-1-78
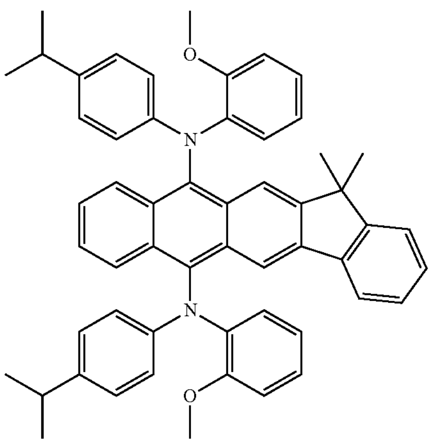
Inv-1-79
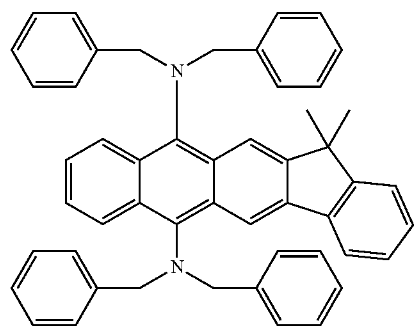
Inv-2-1
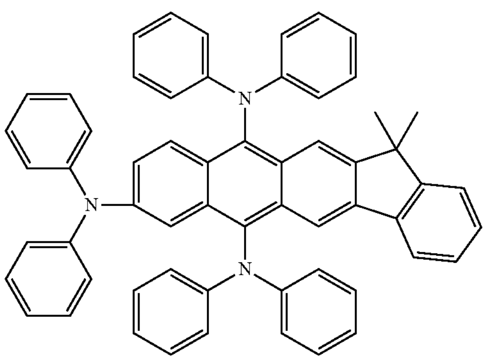
Inv-2-2
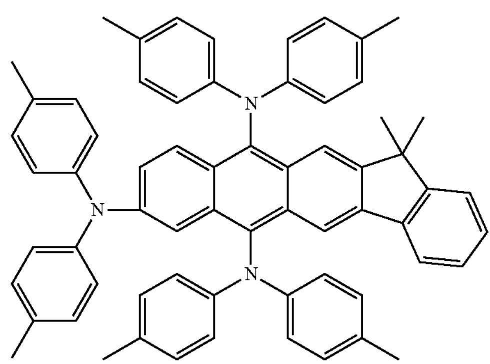
Inv-2-3
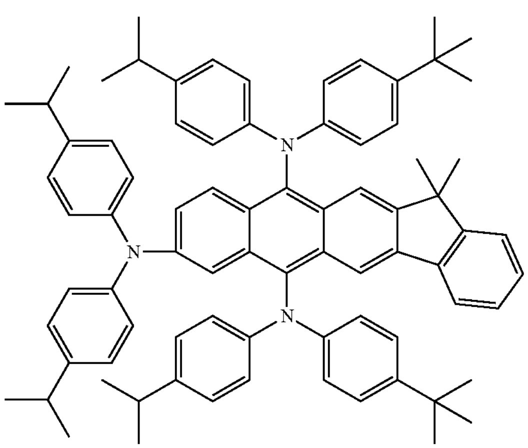

-continued
Inv-2-4
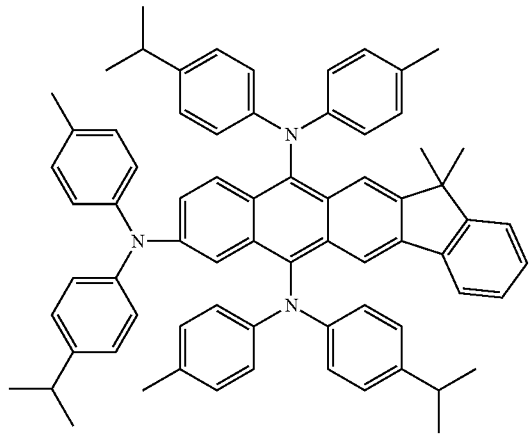
Inv-2-5
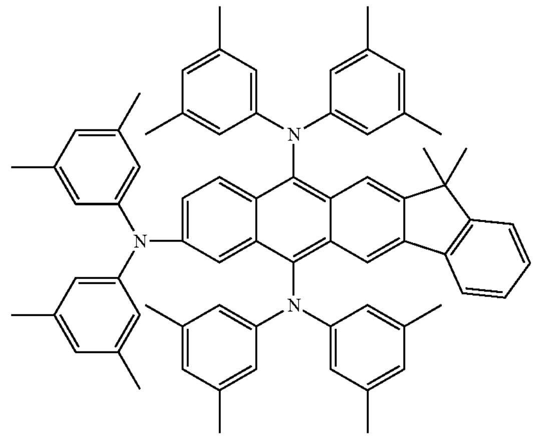
Inv-2-6
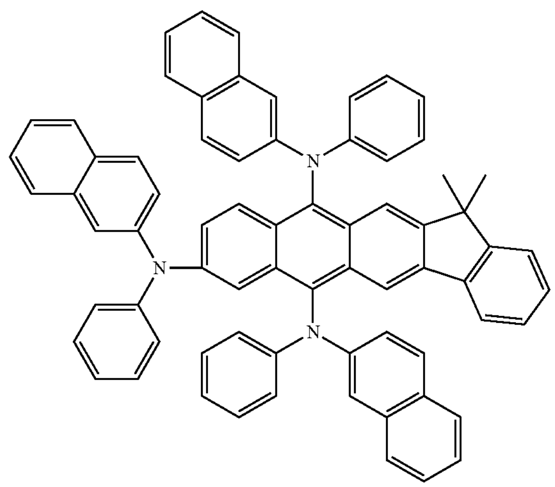
Inv-2-7
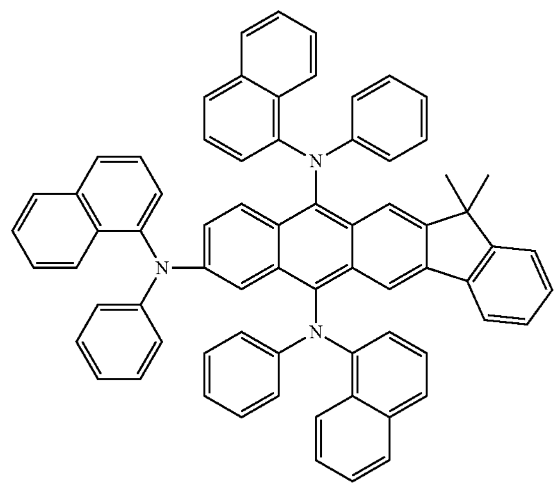
Inv-2-8
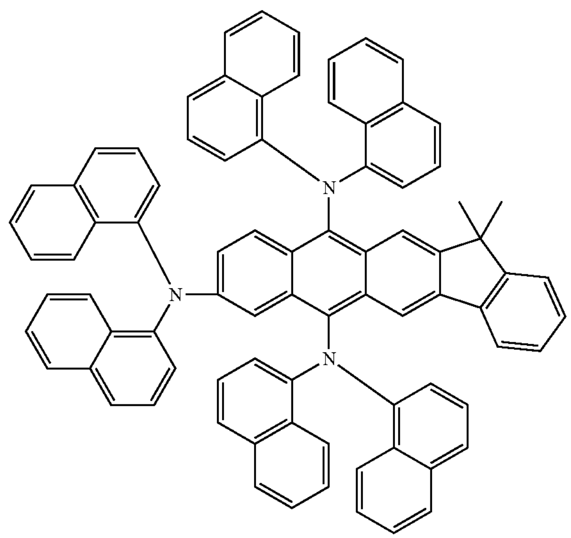
Inv-2-9
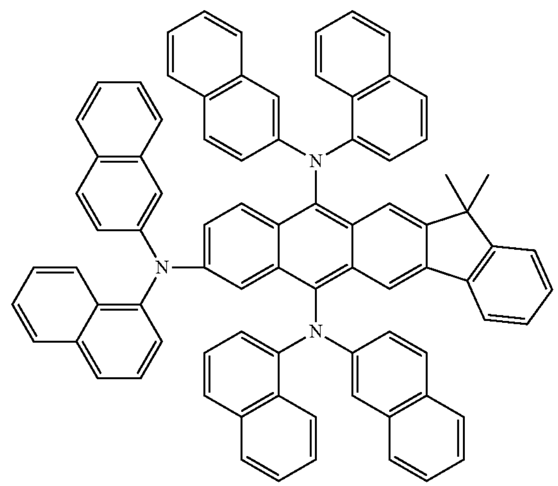

-continued
Inv-2-10
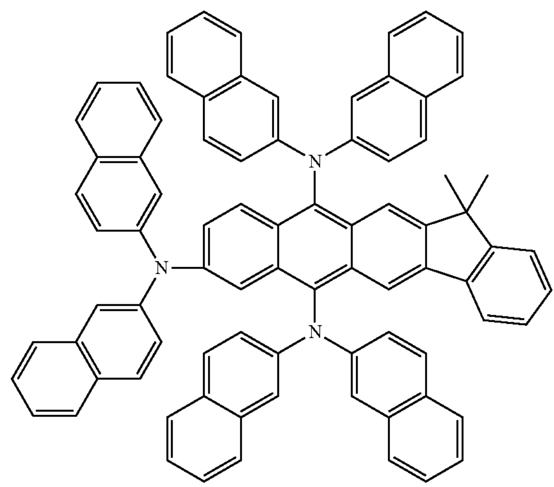
Inv-2-11
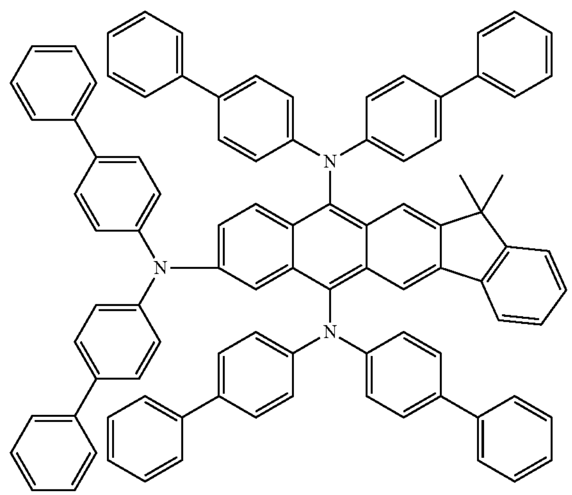
Inv-2-12
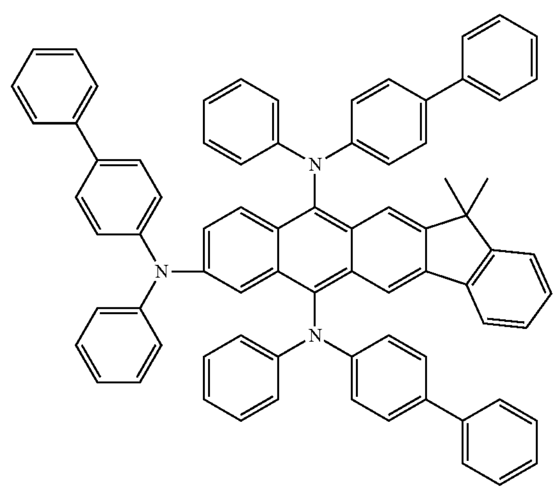
Inv-2-13
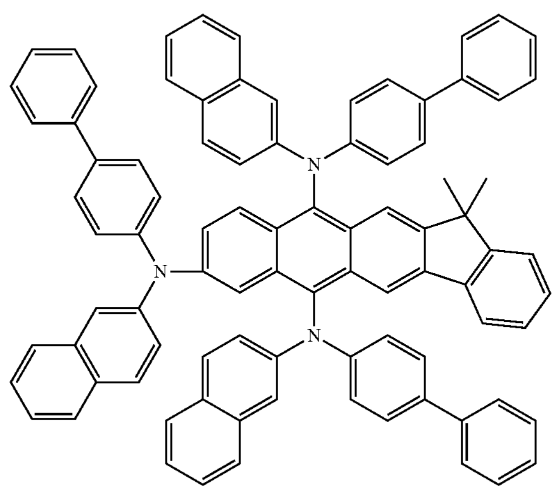
Inv-2-14
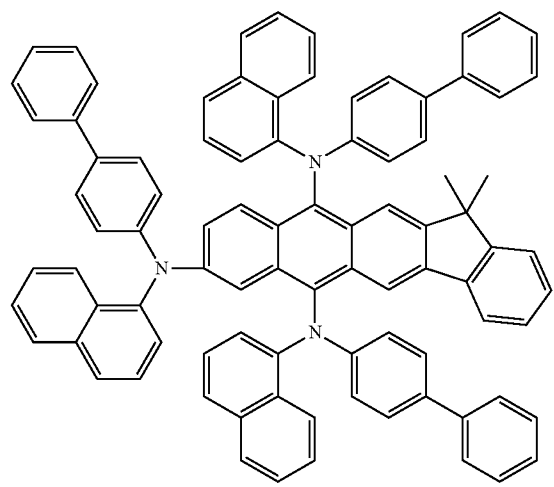
Inv-2-15
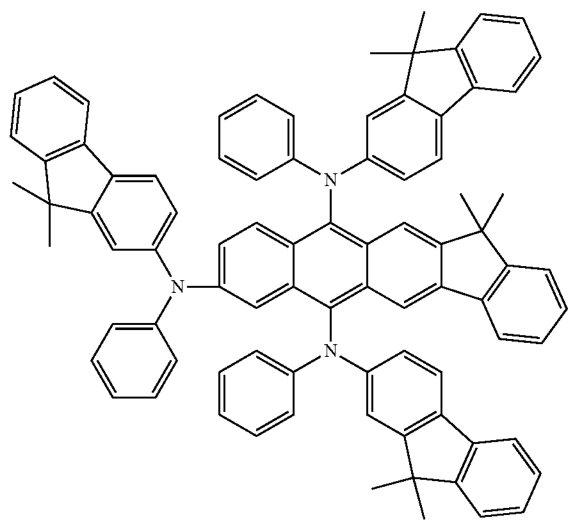

-continued
Inv-2-16
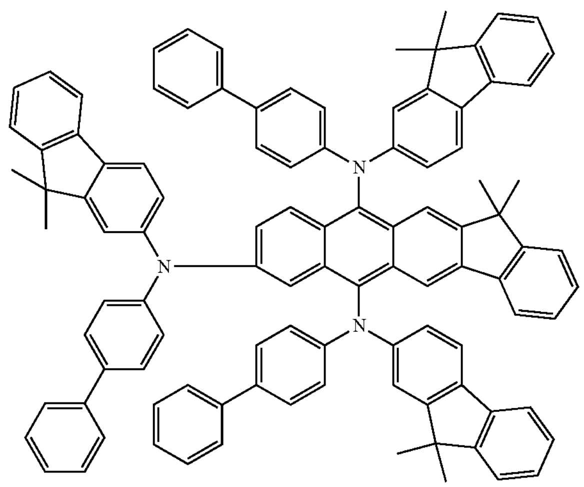
Inv-2-17
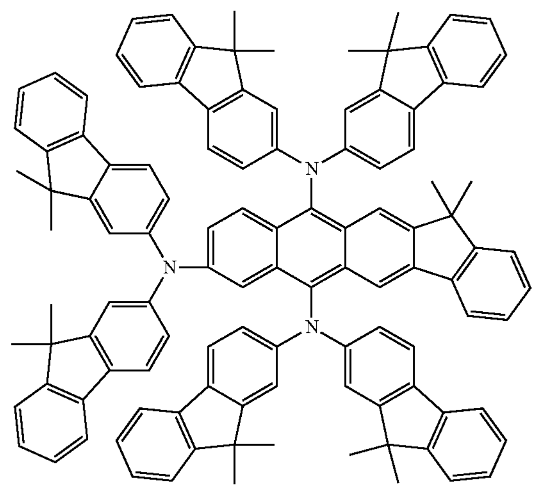
Inv-2-18
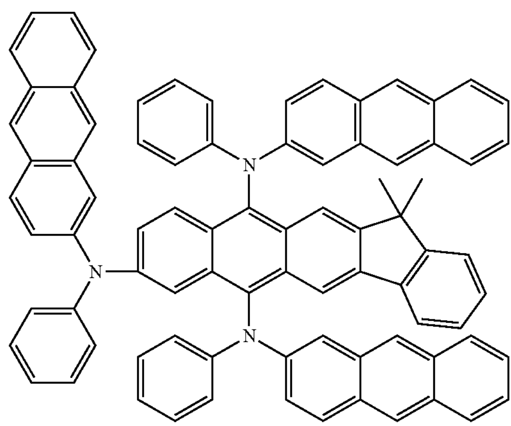
Inv-2-19
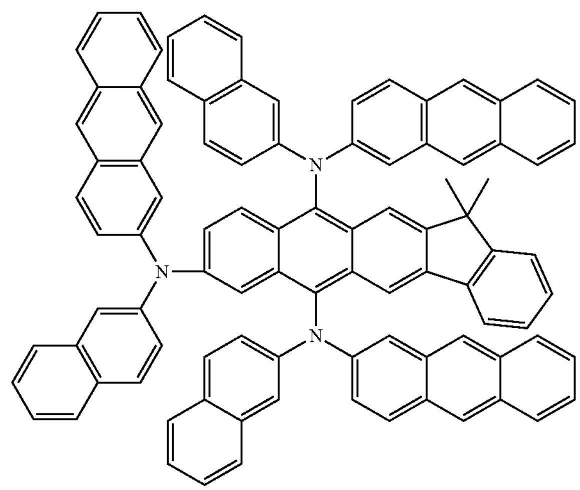
Inv-2-20
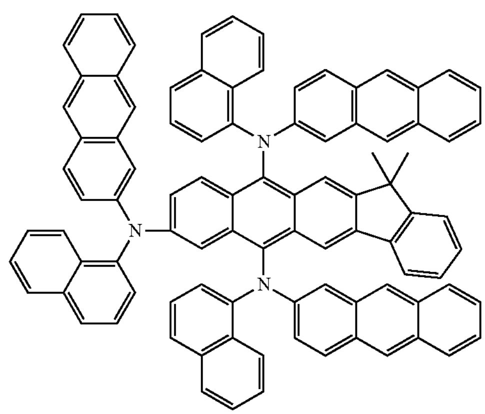
Inv-2-21
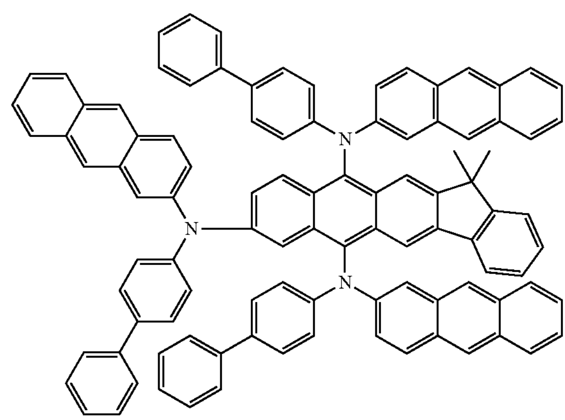

-continued
Inv-2-22
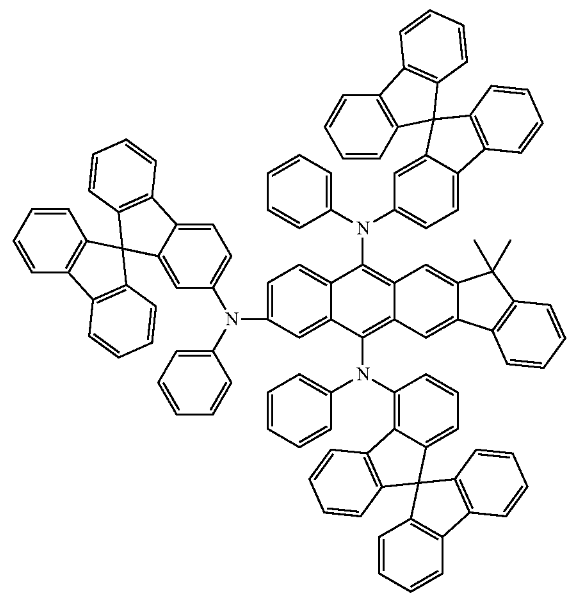
Inv-2-23
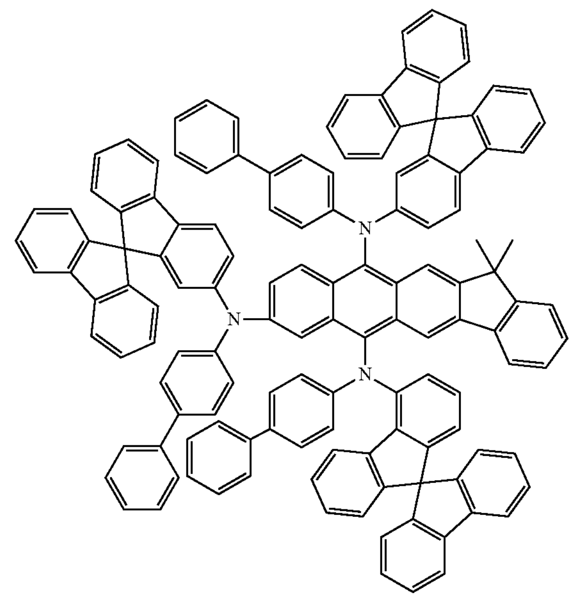
Inv-2-24
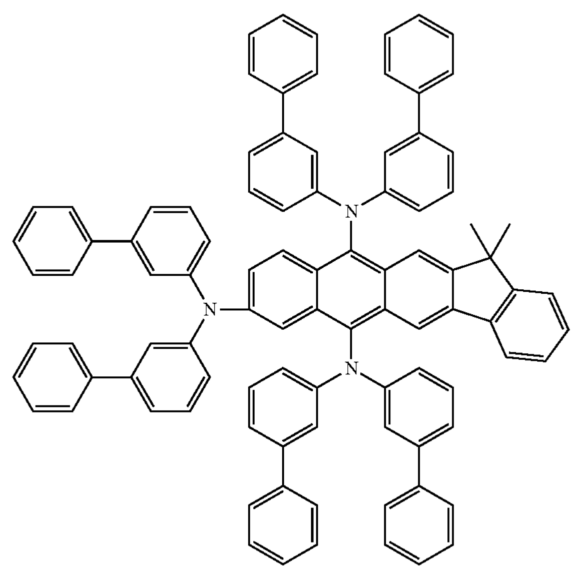
Inv-2-25
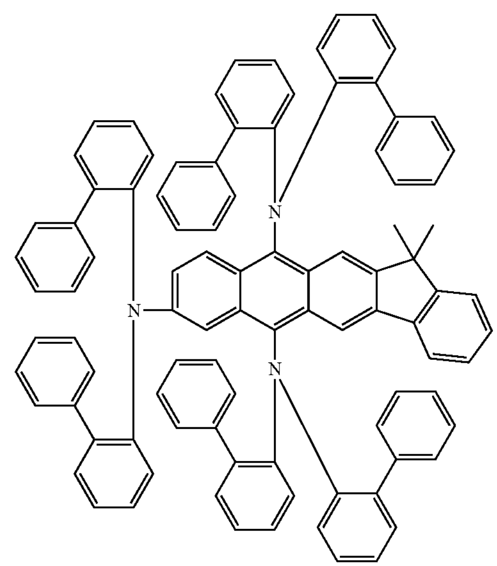

-continued
Inv-2-26
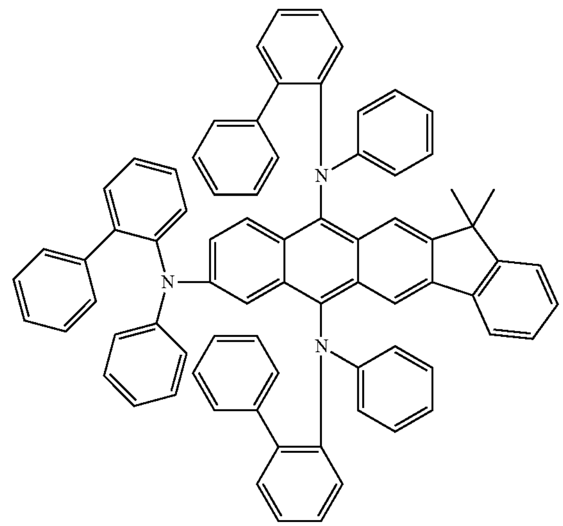
Inv-2-27
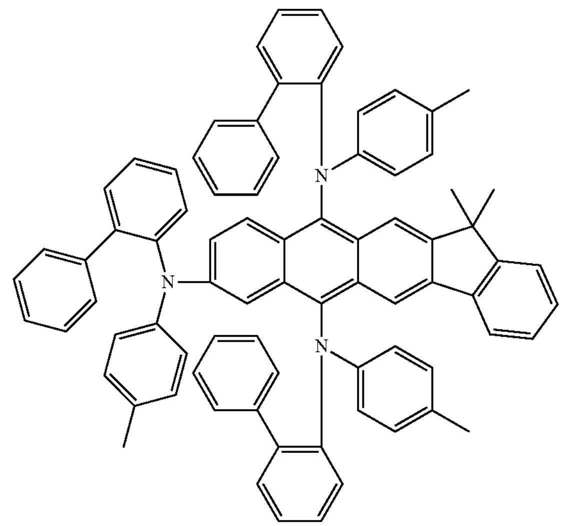
Inv-2-28
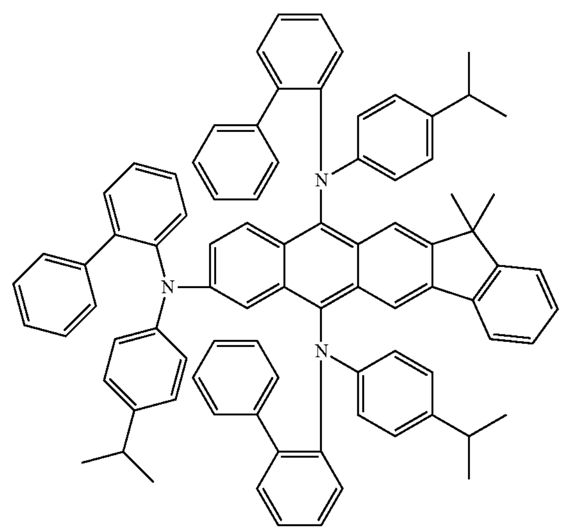
Inv-2-29
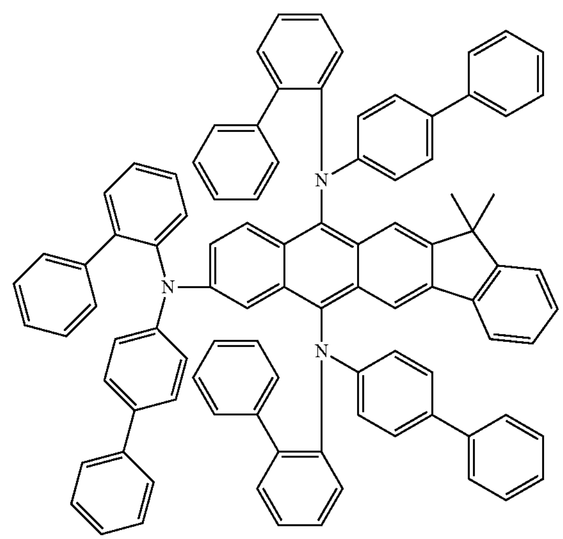

-continued
Inv-2-30
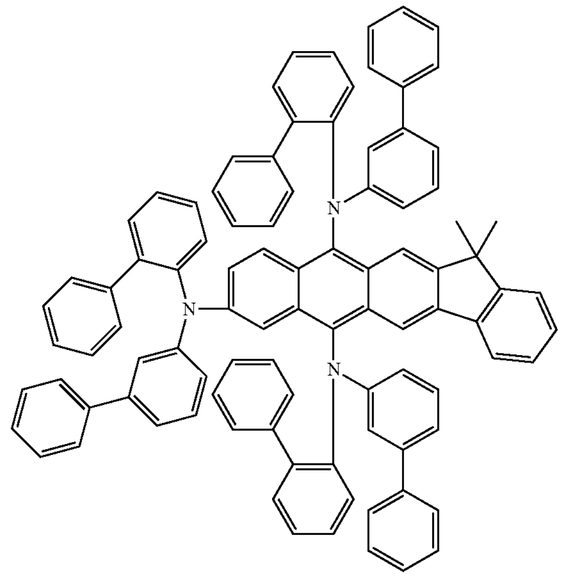
Inv-2-31
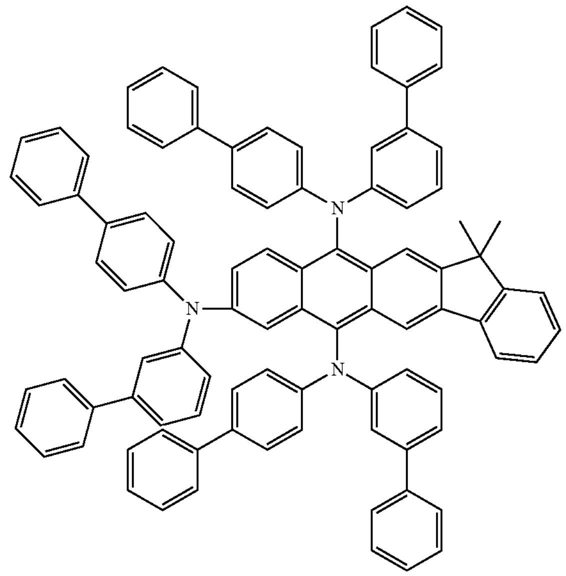
Inv-2-32
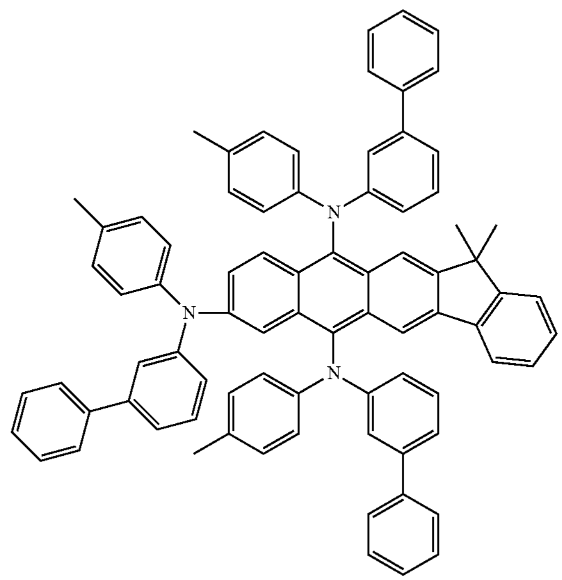
Inv-2-33
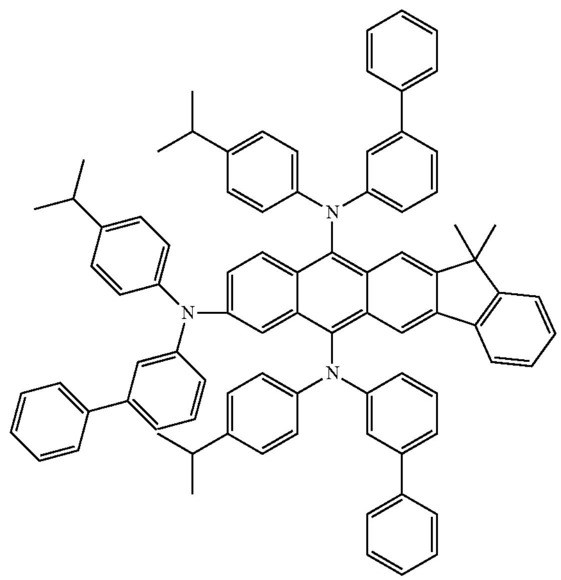

-continued
Inv-2-34
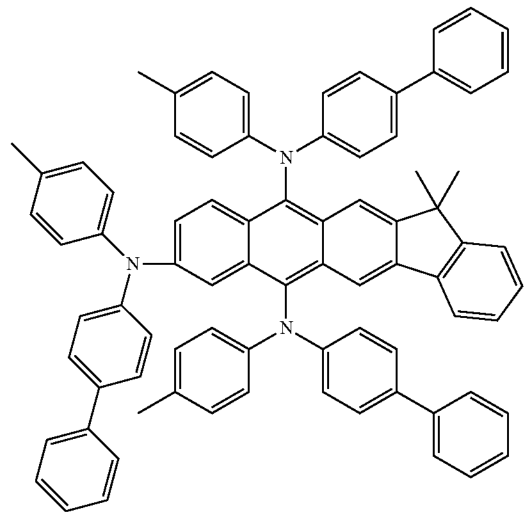
Inv-2-35
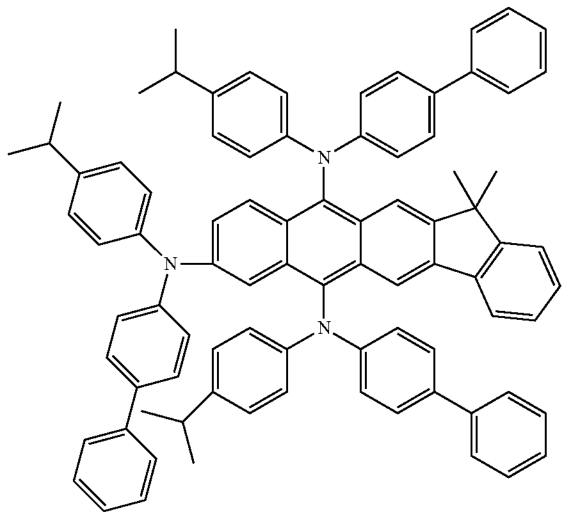
Inv-2-36
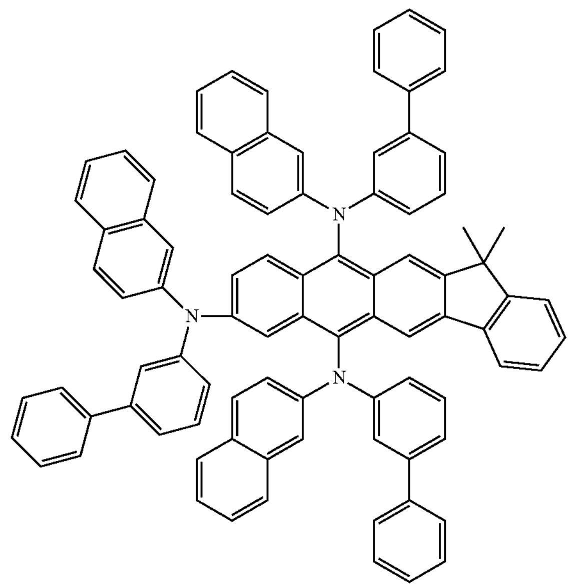
Inv-2-37
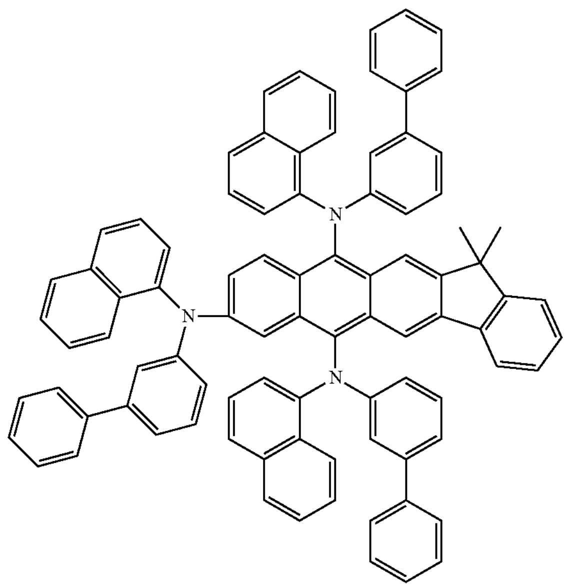

-continued
Inv-2-38
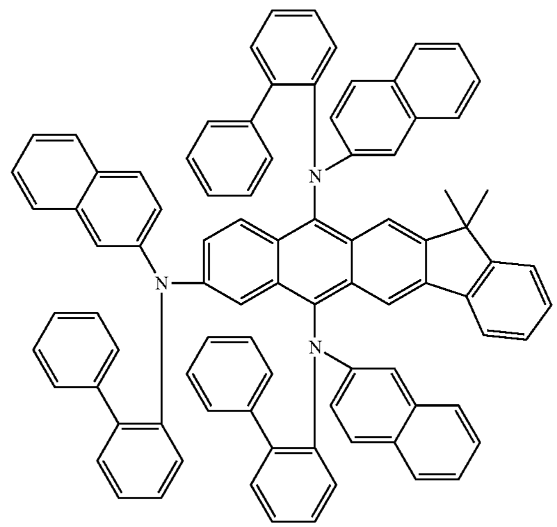
Inv-2-39
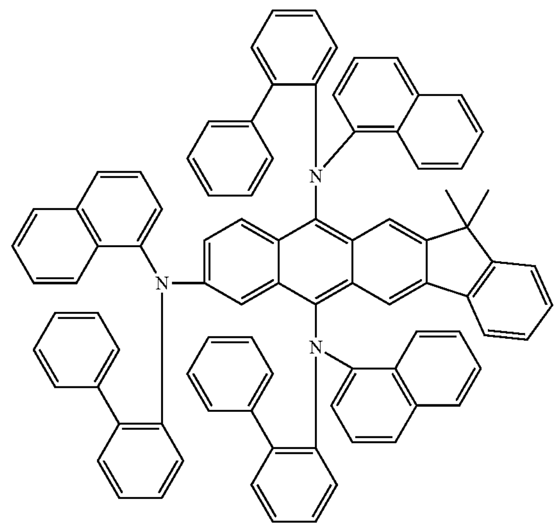
Inv-2-40
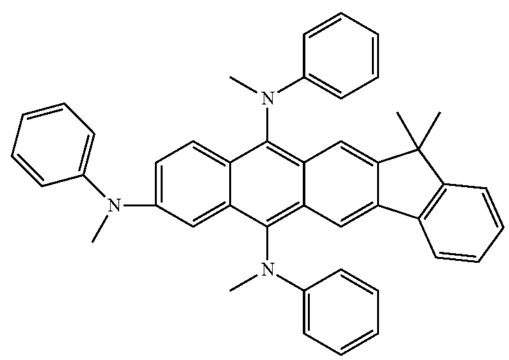
Inv-2-41
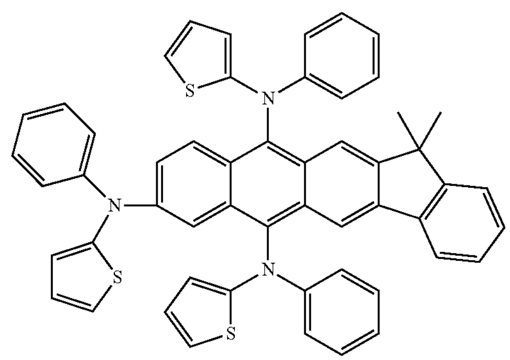
Inv-2-42
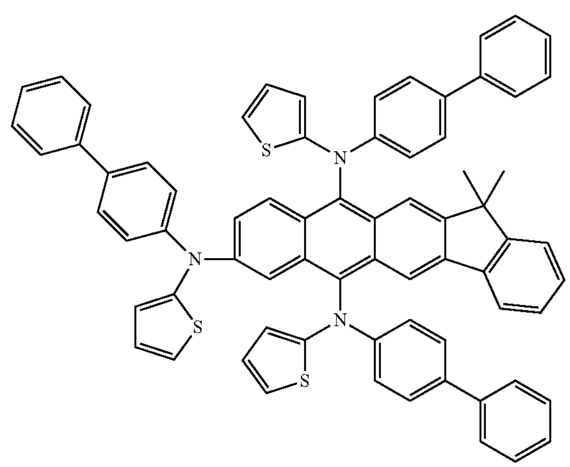
Inv-2-43
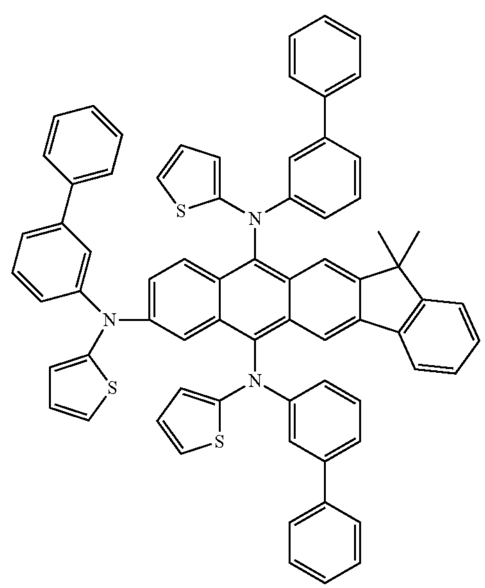

-continued
Inv-2-44
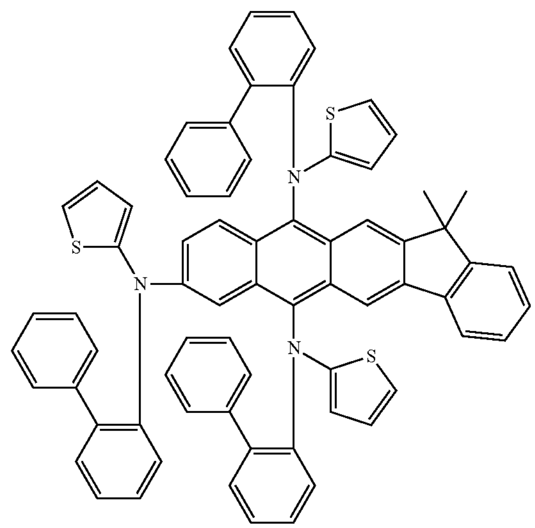
Inv-2-45
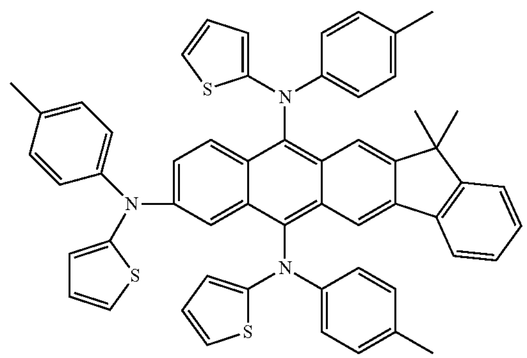
Inv-2-46
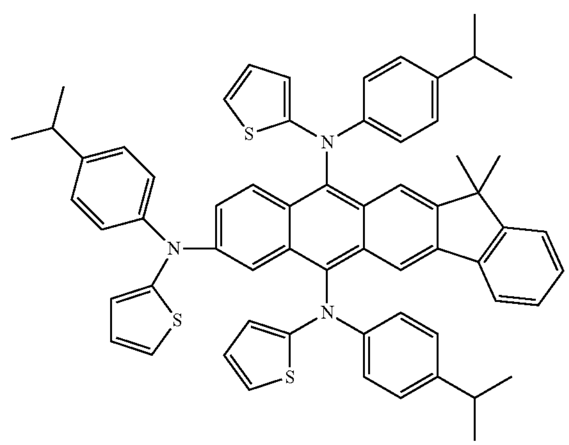
Inv-2-47
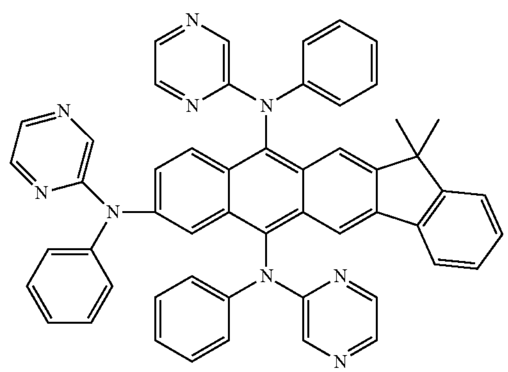
Inv-2-48
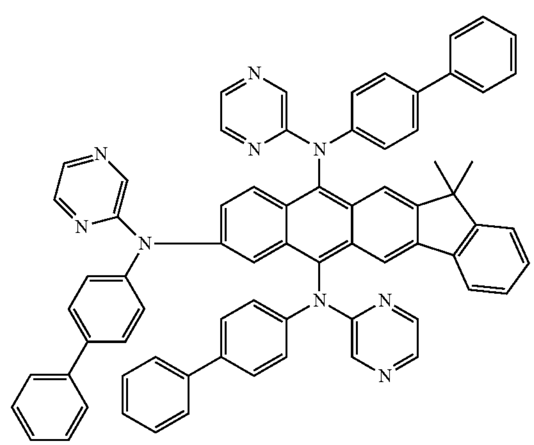
Inv-2-49
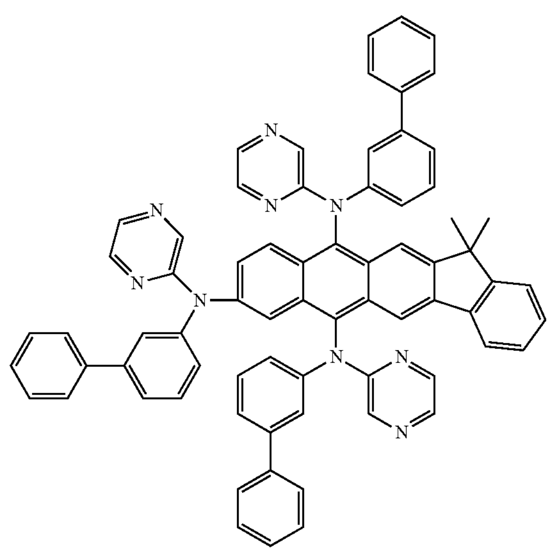

-continued
Inv-2-50
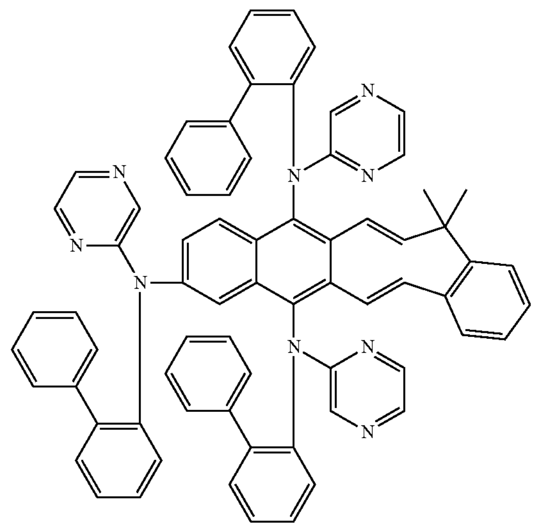
Inv-2-51
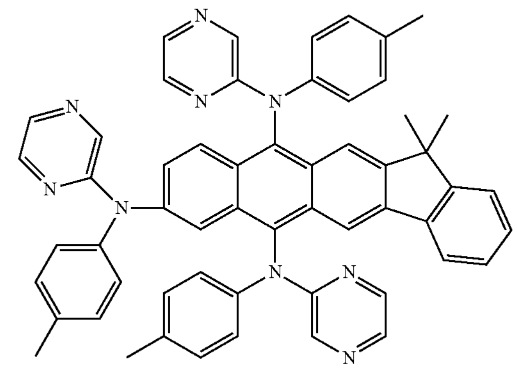
Inv-2-52
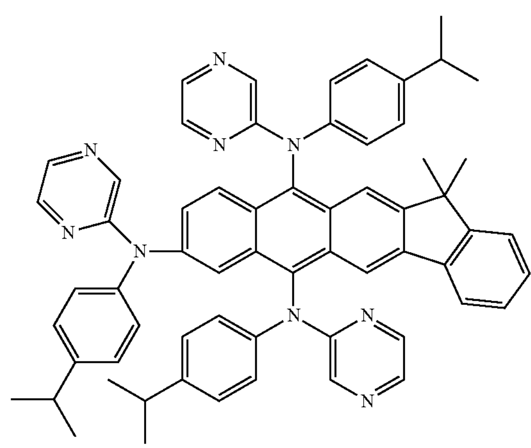
Inv-2-53
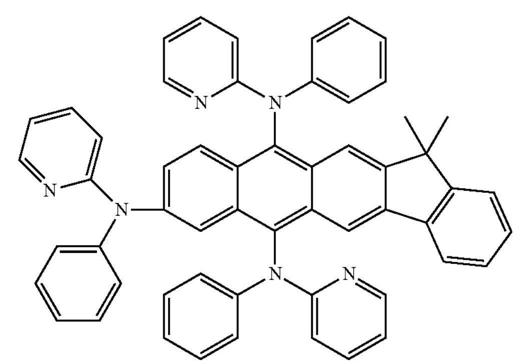
Inv-2-54
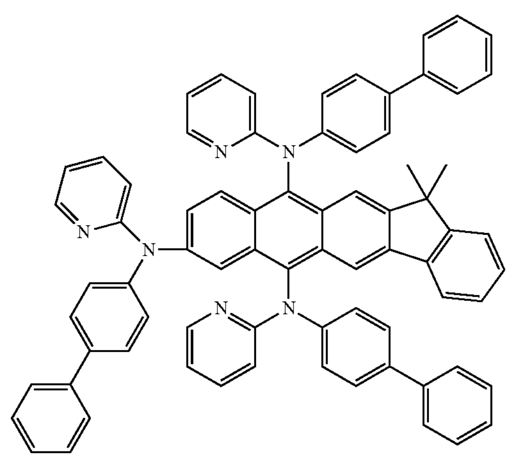
Inv-2-55
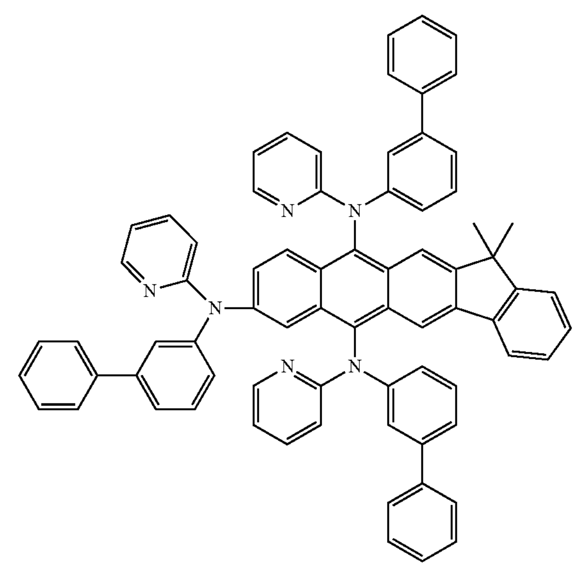

-continued
Inv-2-56
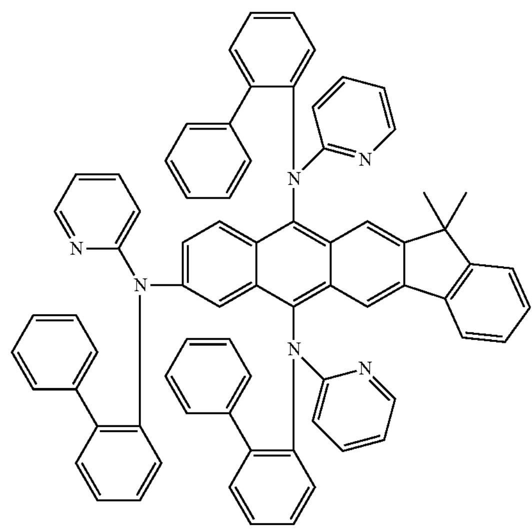
Inv-2-57
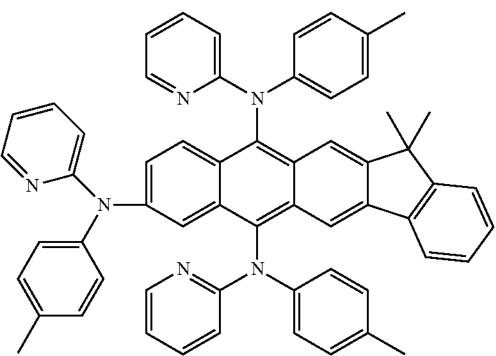
Inv-2-58
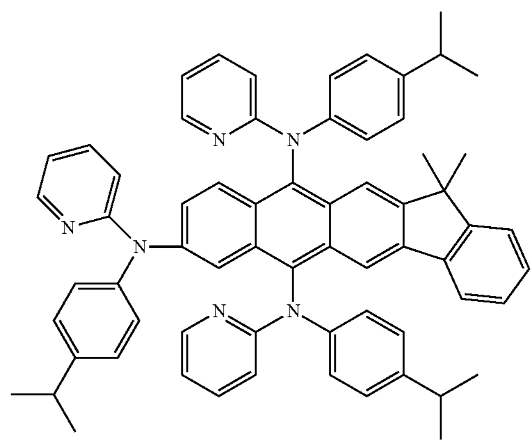
Inv-2-59
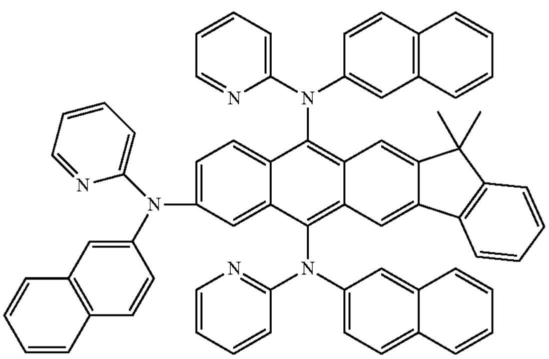
Inv-2-60
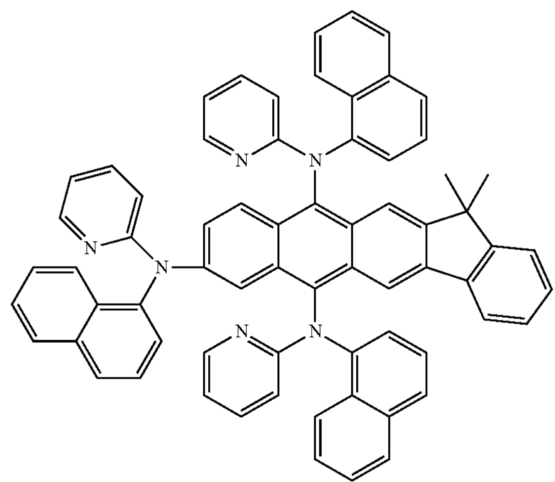
Inv-2-61
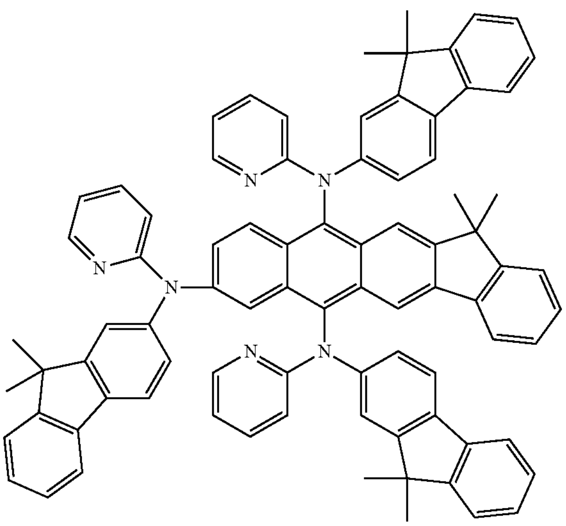

-continued
Inv-2-62
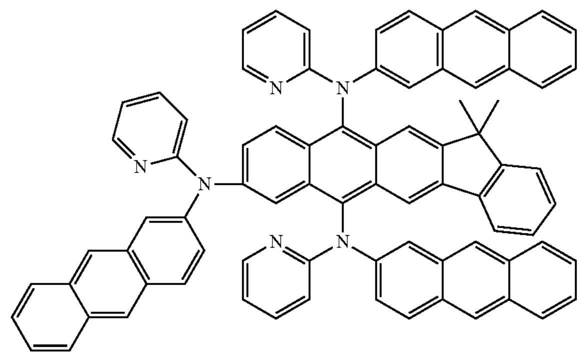
Inv-2-63
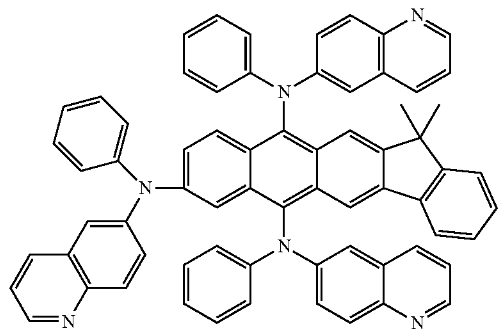
Inv-2-64
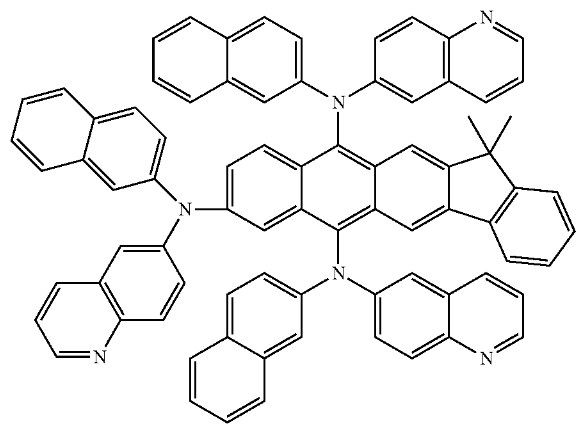
Inv-2-65
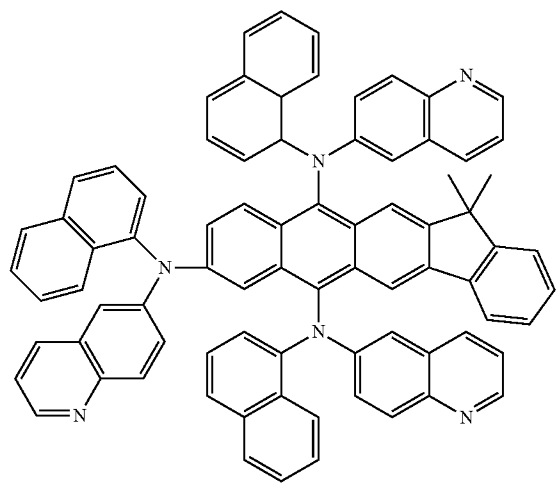
Inv-2-66
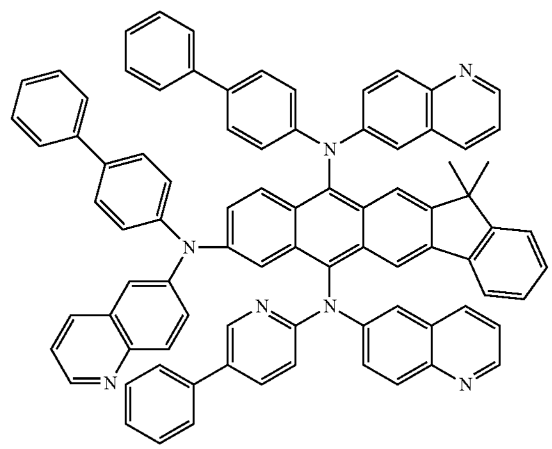
Inv-2-67
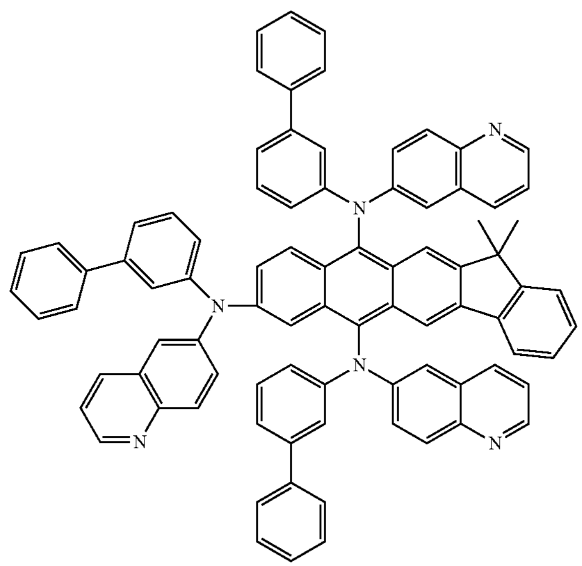

-continued
Inv-2-68
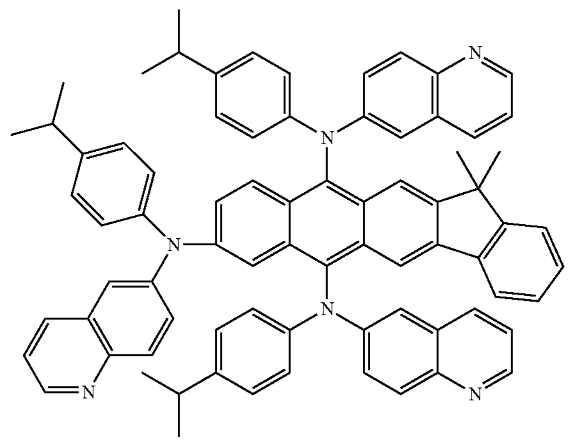
Inv-2-69
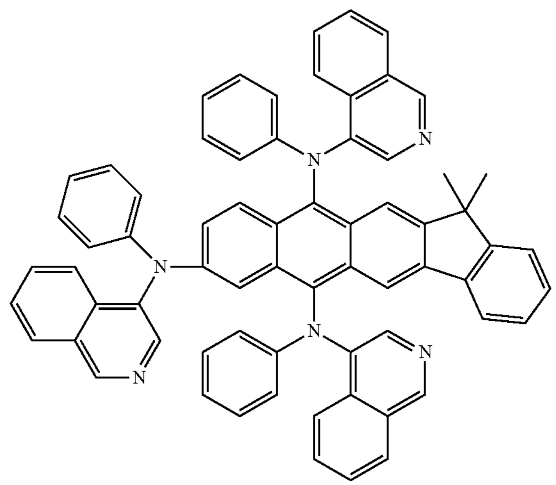
Inv-2-70
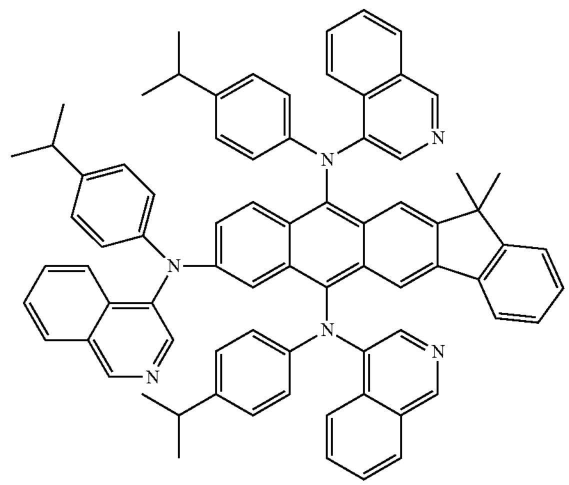
Inv-2-71
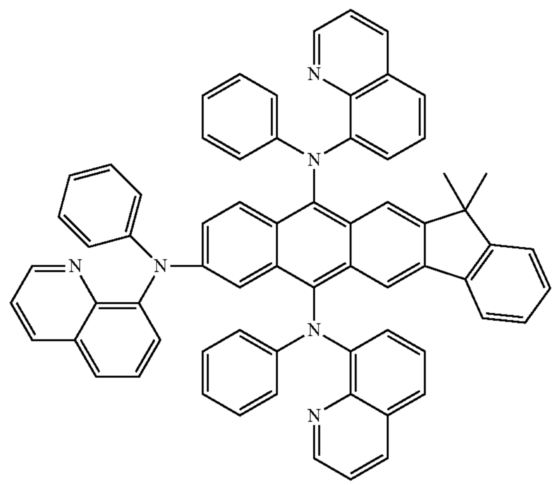
Inv-2-72
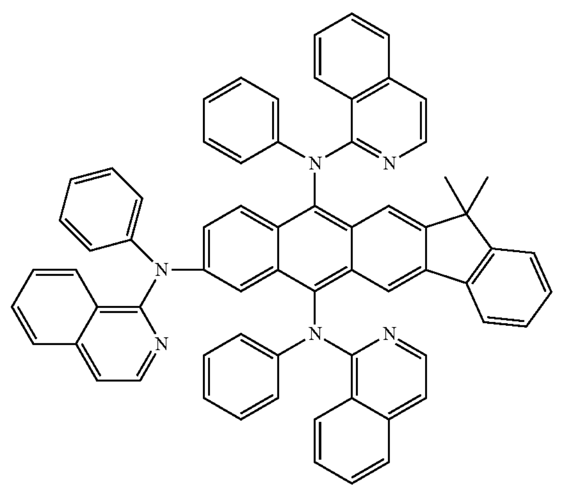
Inv-2-73
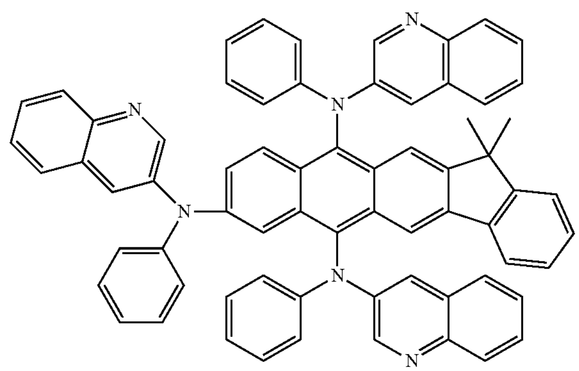

-continued
Inv-2-74
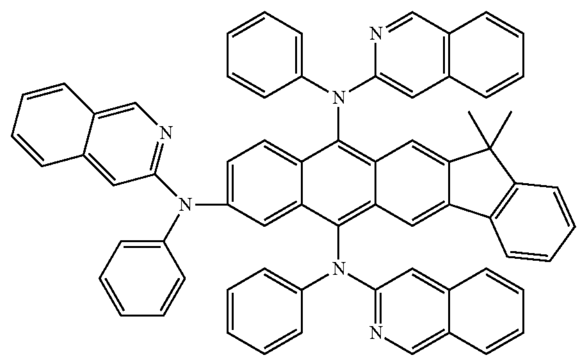
Inv-2-75
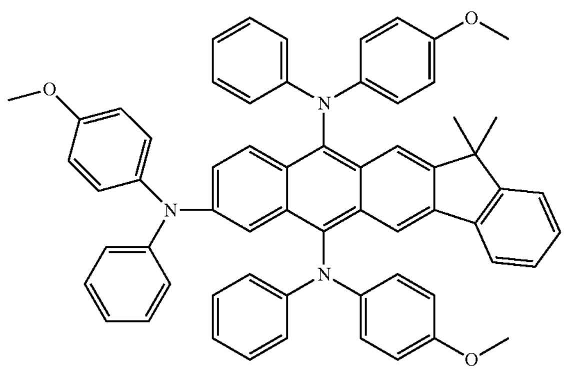
Inv-2-76
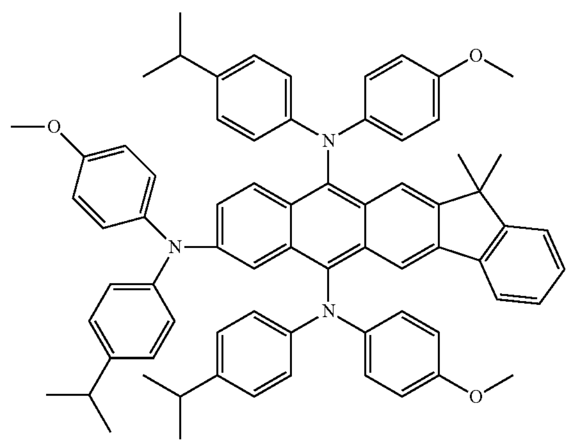
Inv-2-77
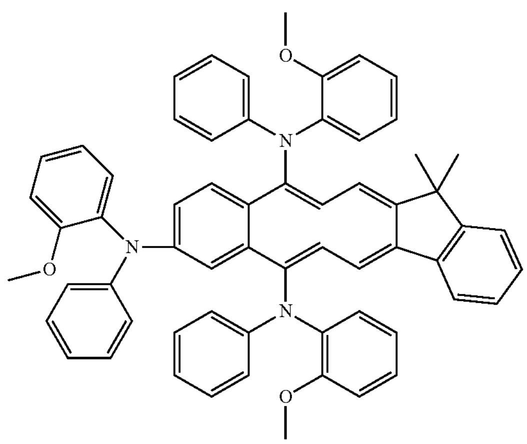
Inv-2-78
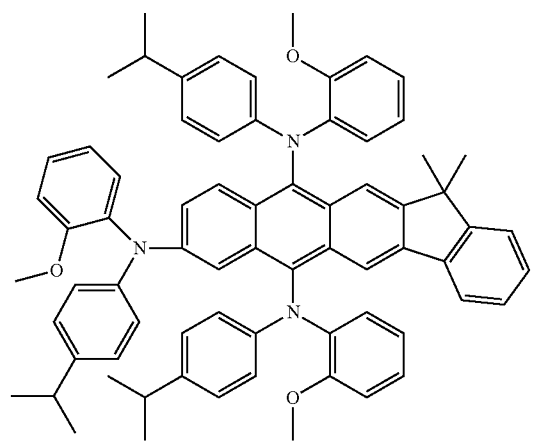
Inv-2-79
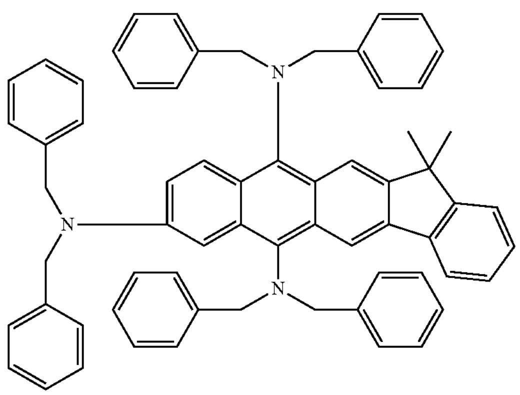

-continued
Inv-3-1
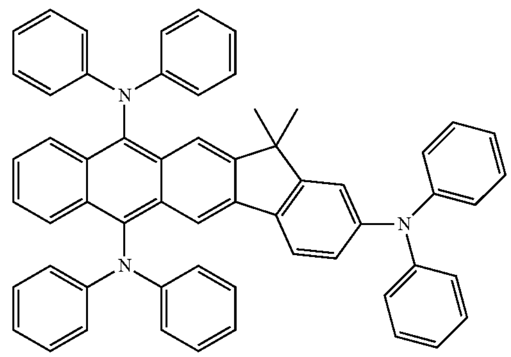
Inv-3-2
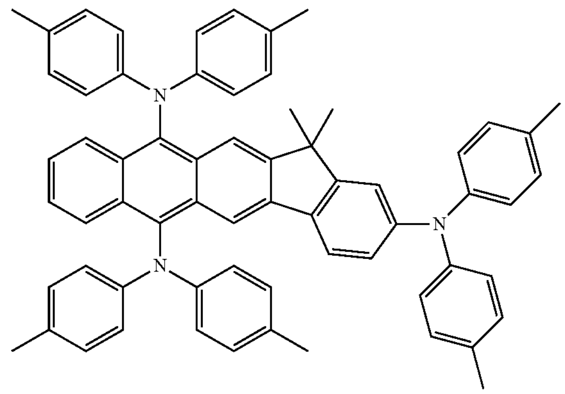
Inv-3-3
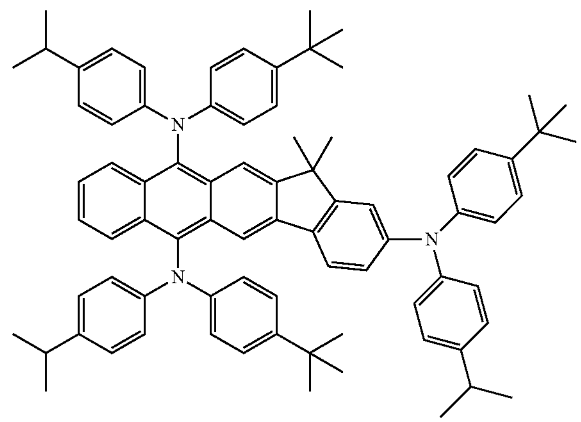
Inv-3-4
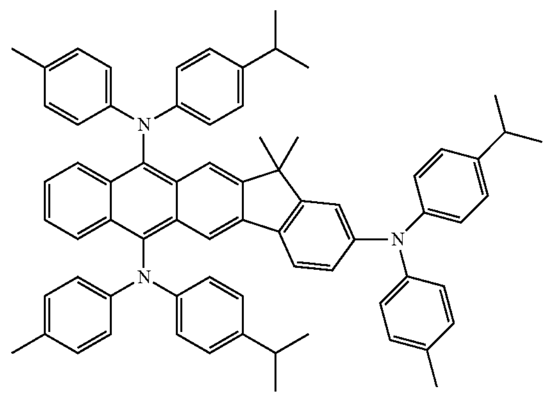
Inv-3-5
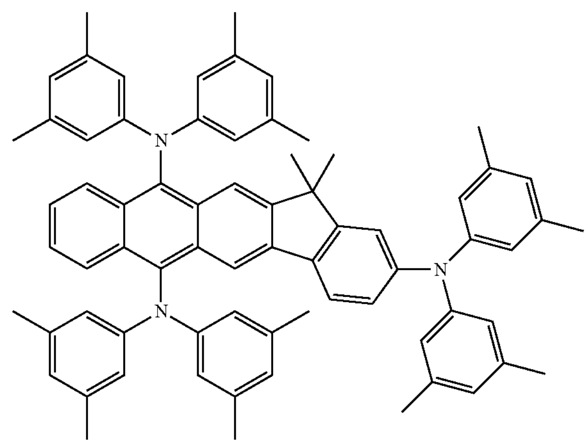
Inv-3-6
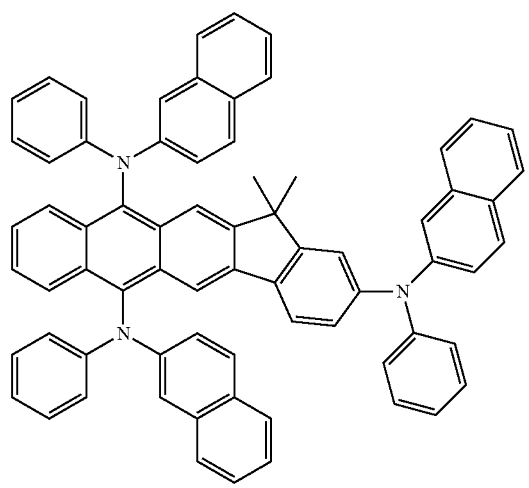

-continued
Inv-3-7
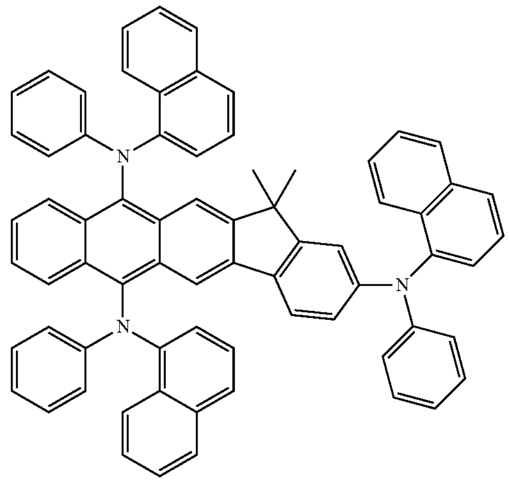
Inv-3-8
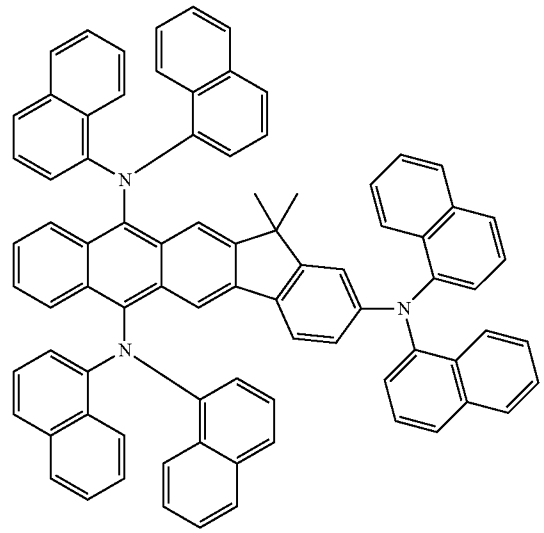
Inv-3-9
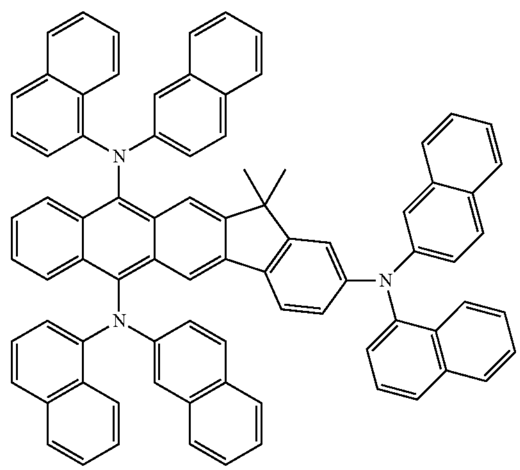
Inv-3-10
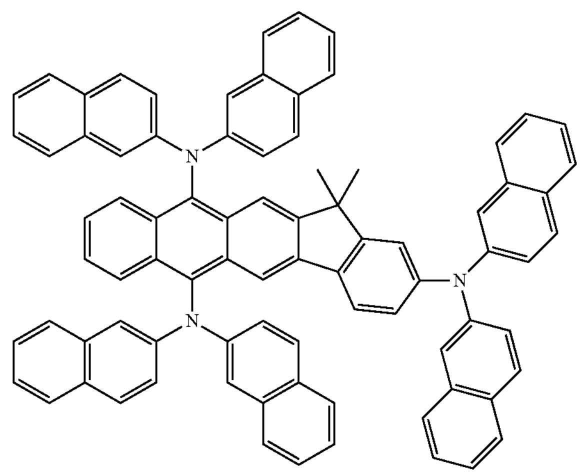
Inv-3-11
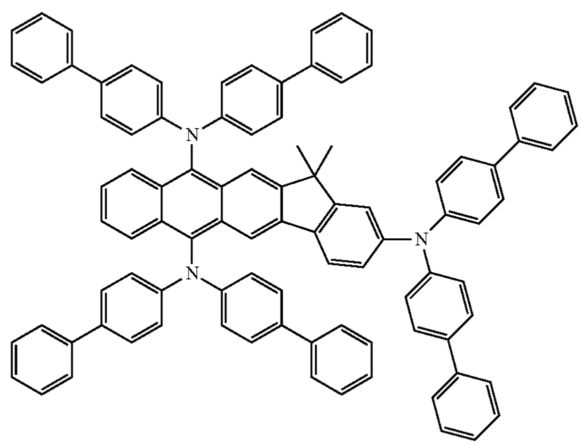
Inv-3-12
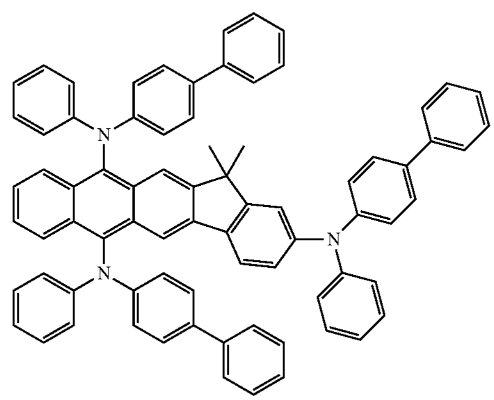

-continued
Inv-3-13
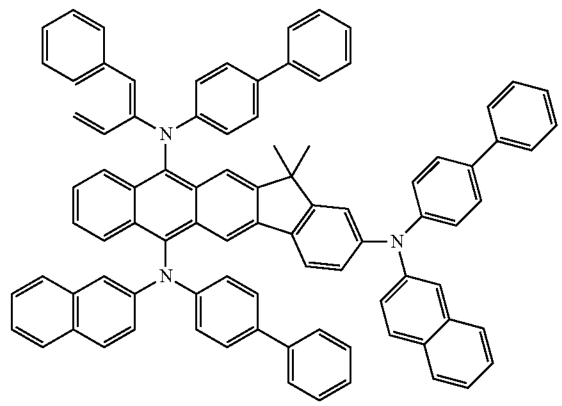
Inv-3-14
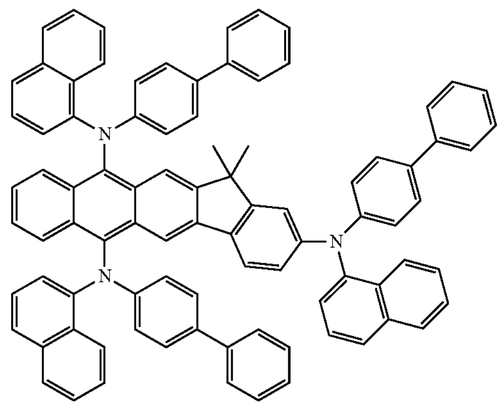
Inv-3-15
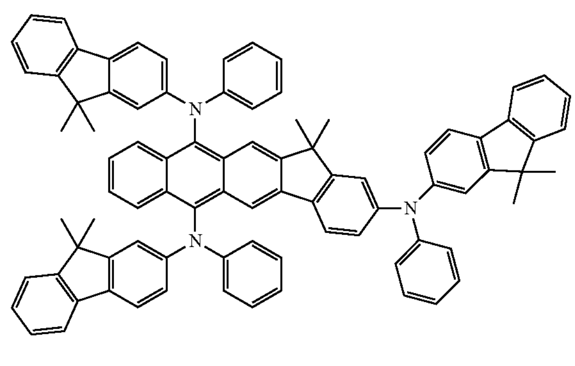
Inv-3-16
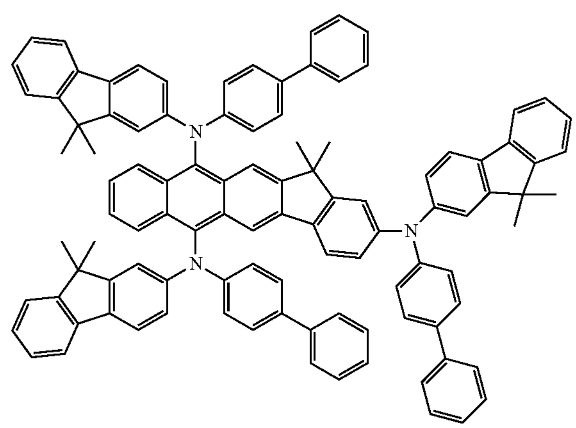
Inv-3-17
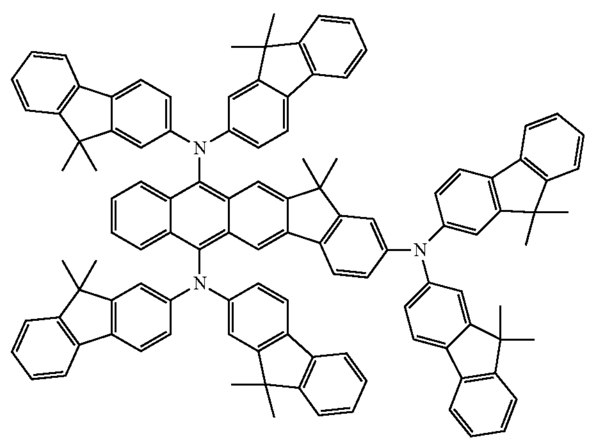
Inv-3-18
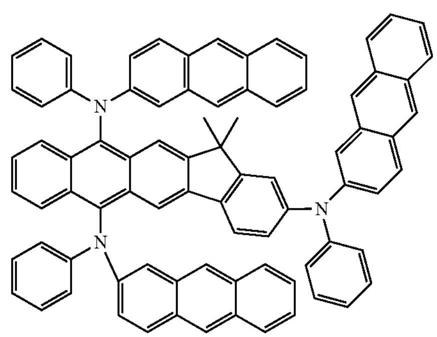

-continued
Inv-3-19
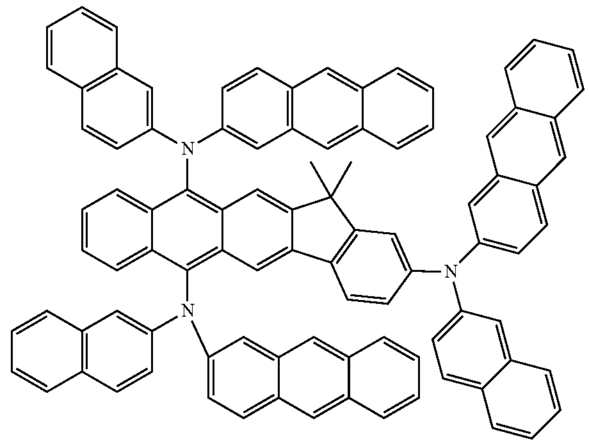
Inv-3-20
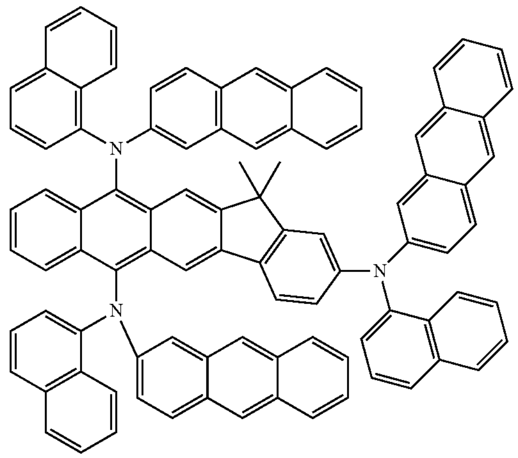
Inv-3-21
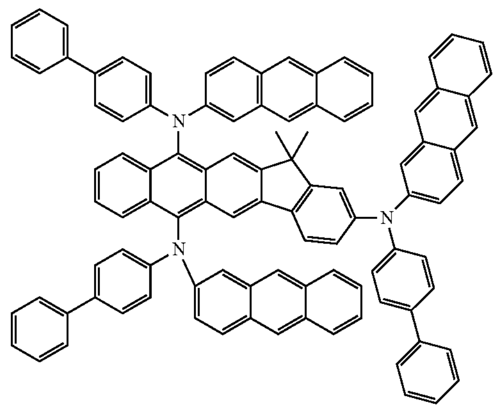
Inv-3-22
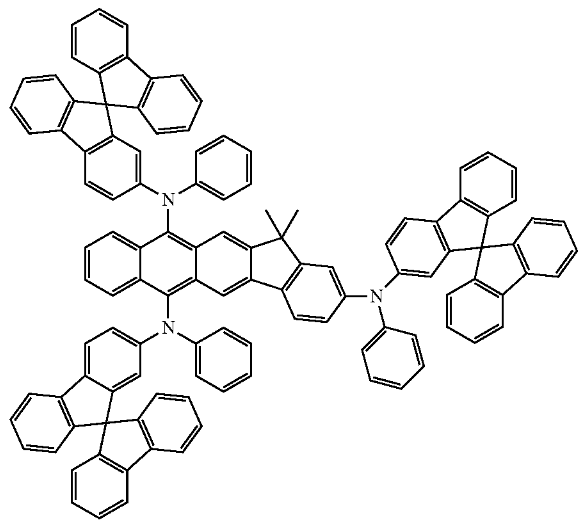
Inv-3-23
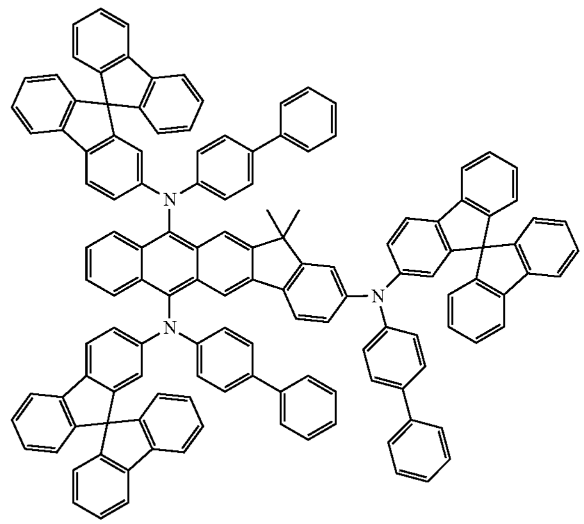
Inv-3-24
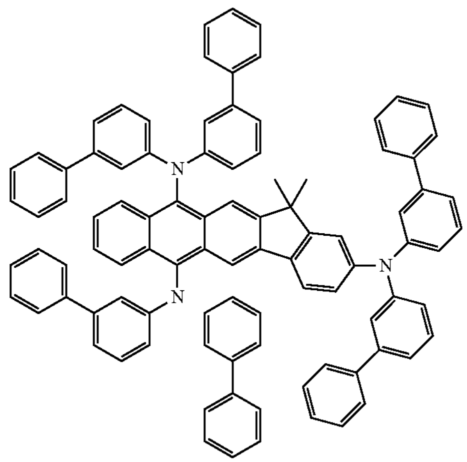

-continued
Inv-3-25
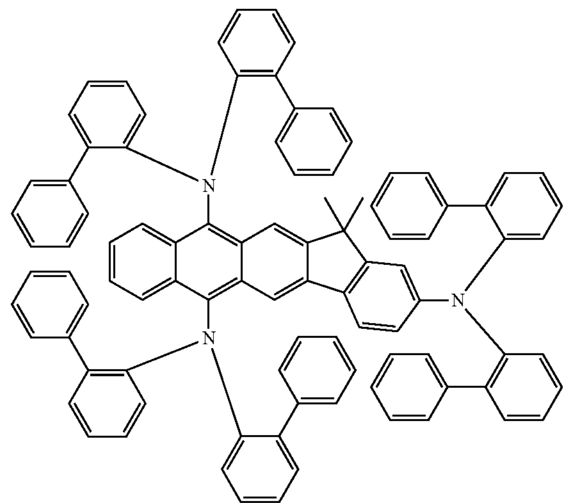
Inv-3-26
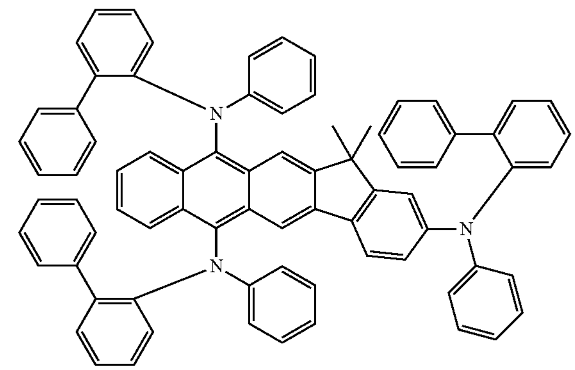
Inv-3-27
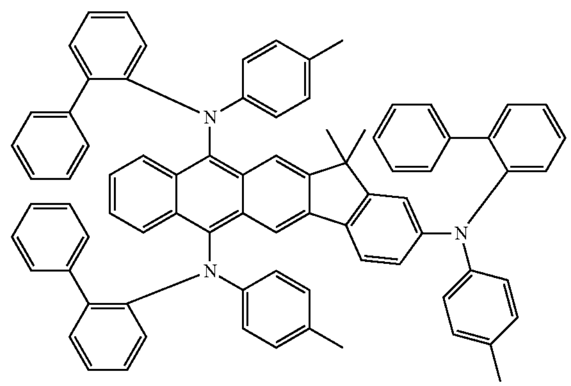
Inv-3-28
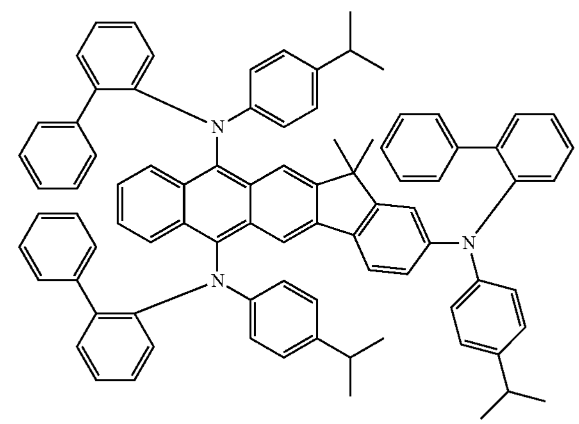
Inv-3-29
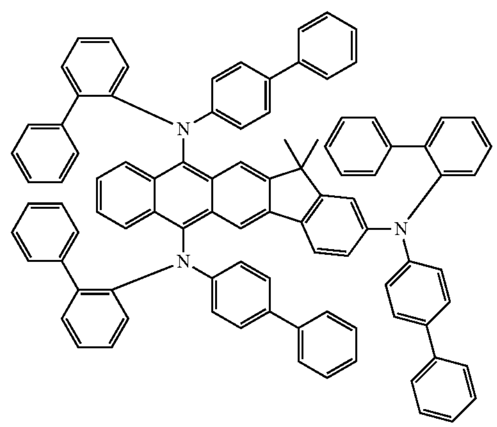
Inv-3-30
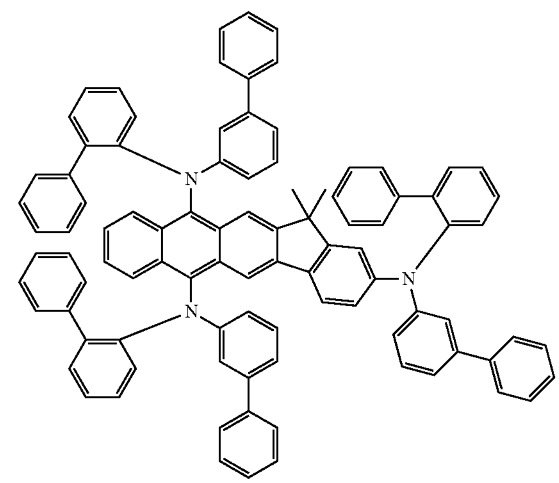

-continued
Inv-3-31
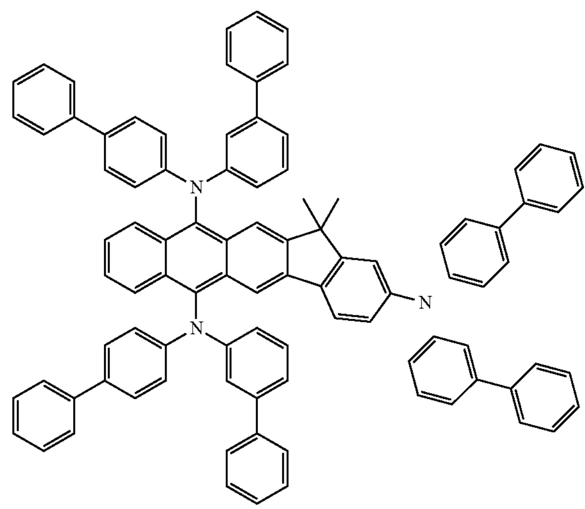
Inv-3-32
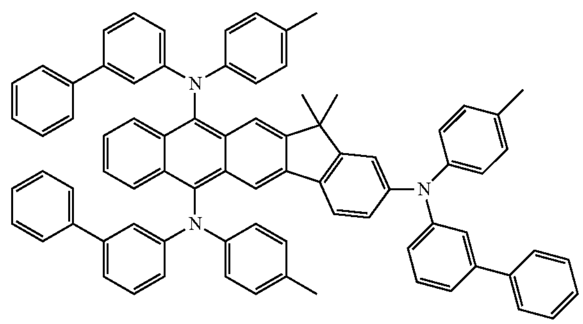
Inv-3-33
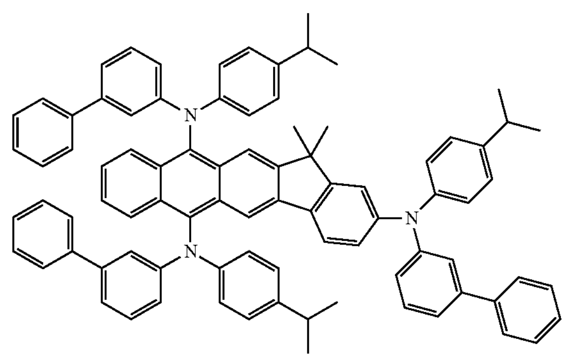
Inv-3-34
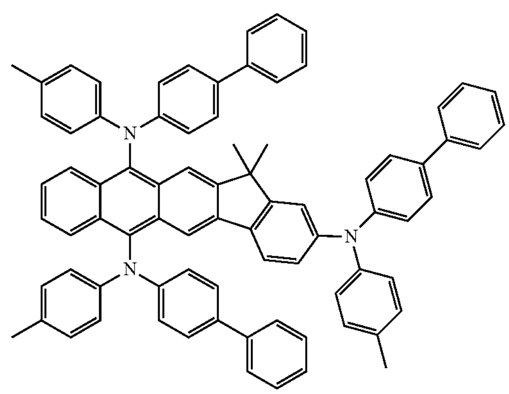
Inv-3-35
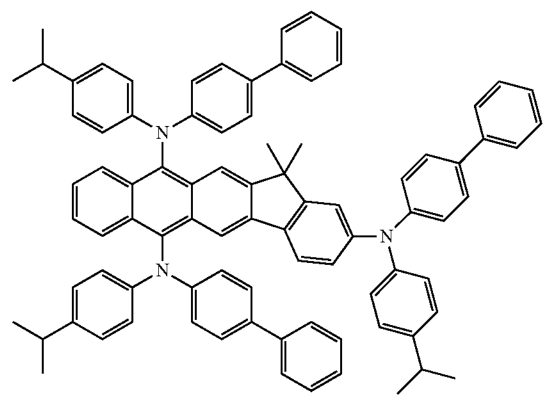
Inv-3-36
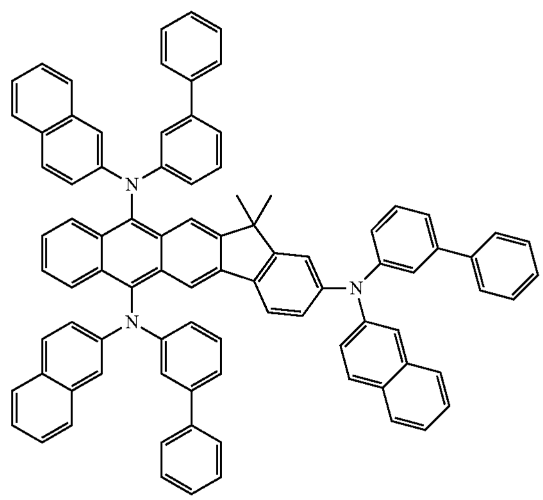

-continued
Inv-3-37
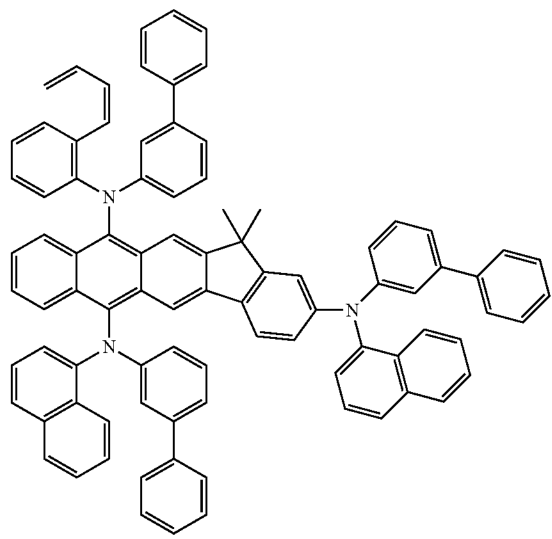
Inv-3-38
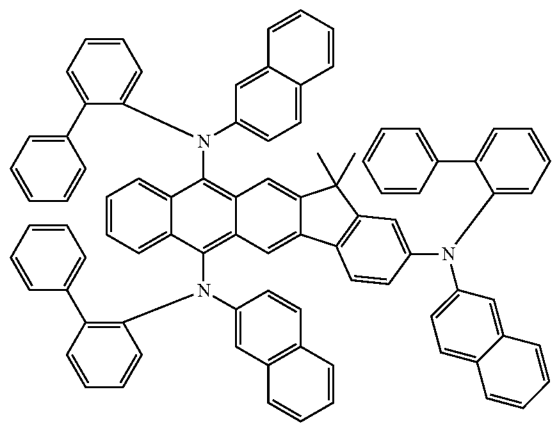
Inv-3-39
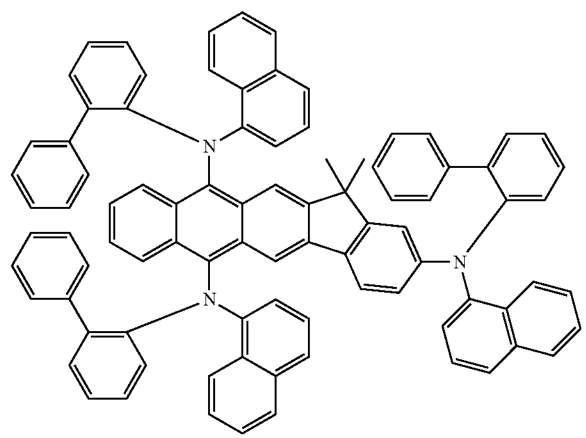
Inv-3-40
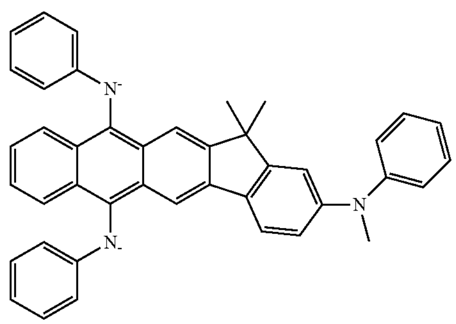
Inv-3-41
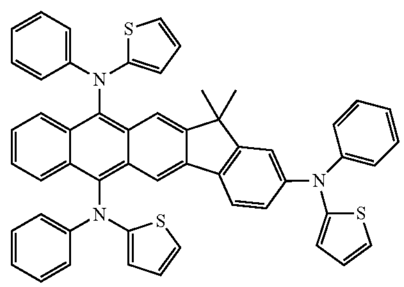
Inv-3-42
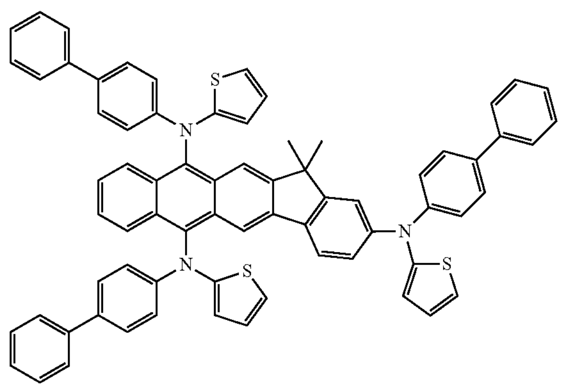

-continued
Inv-3-43
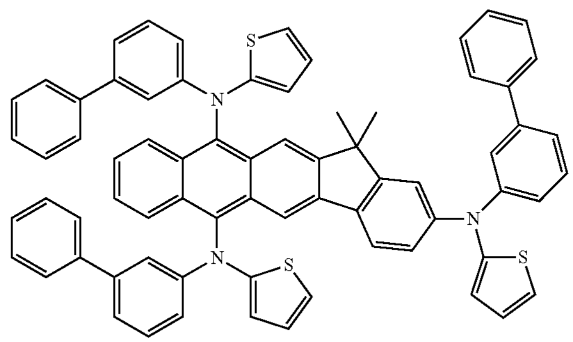
Inv-3-44
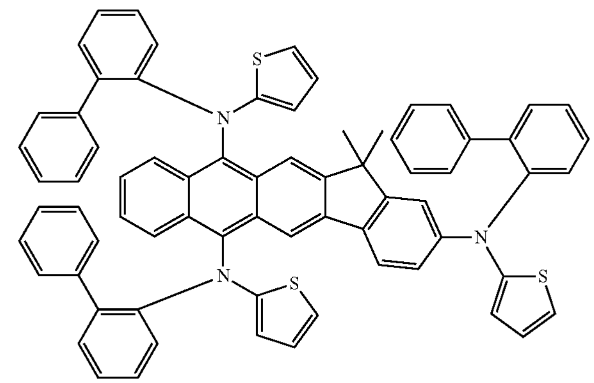
Inv-3-45
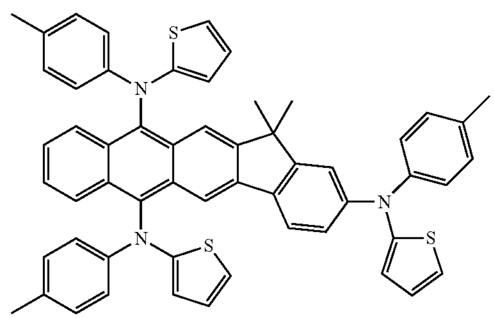
Inv-3-46
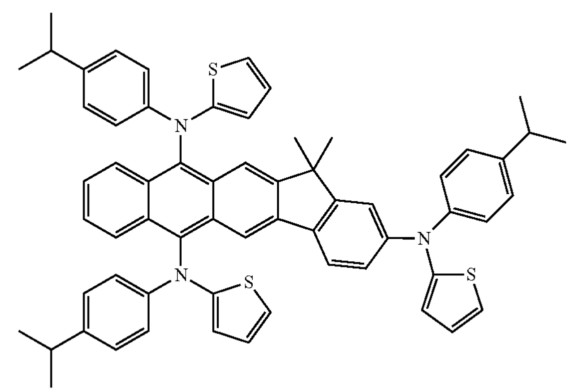
Inv-3-47
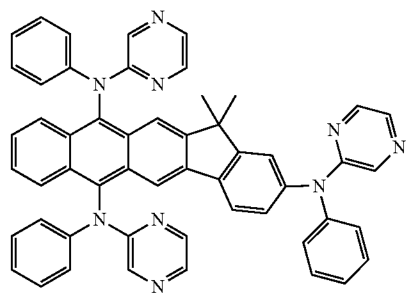
Inv-3-48
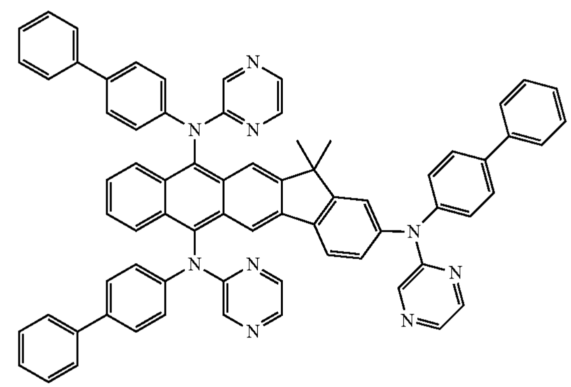
Inv-3-49
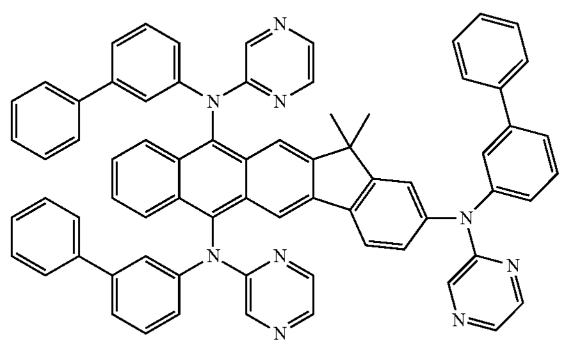
Inv-3-50
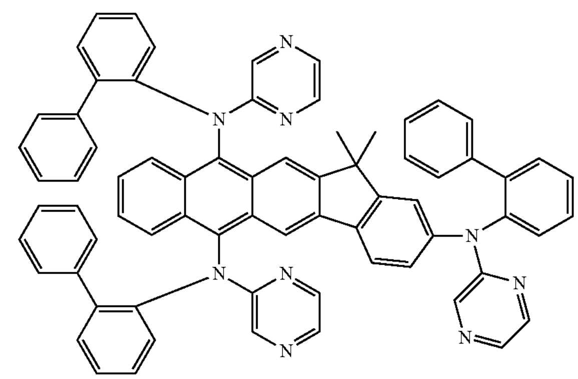

-continued
Inv-3-51
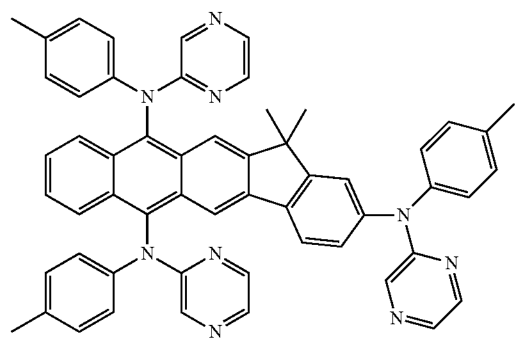
Inv-3-52
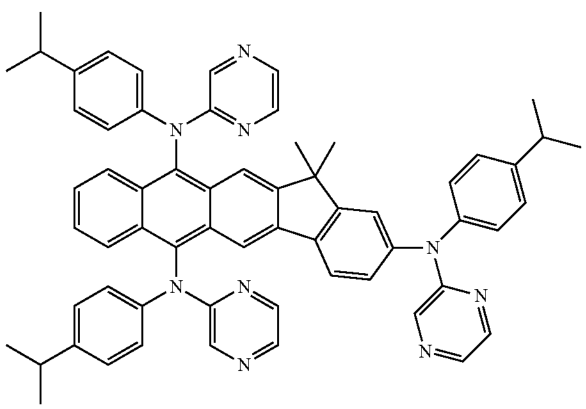
Inv-3-53
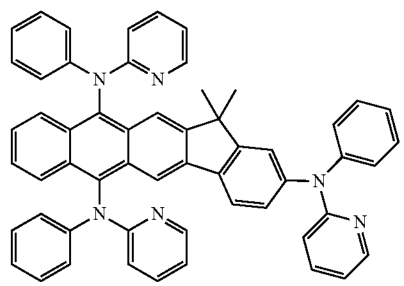
Inv-3-54
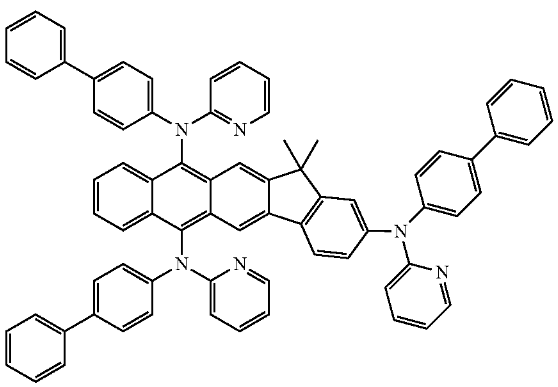
Inv-3-55
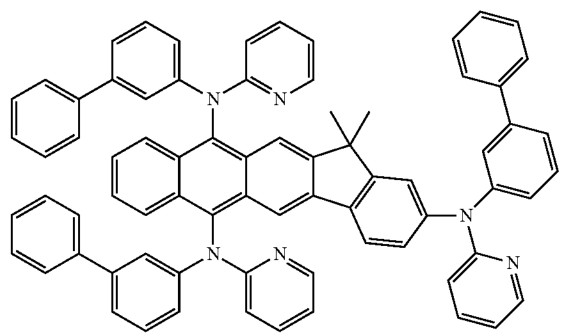
Inv-3-56
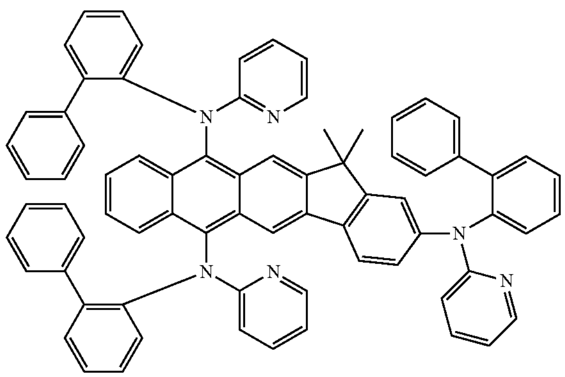
Inv-3-57
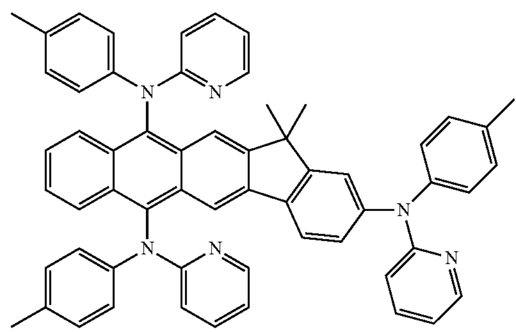
Inv-3-58
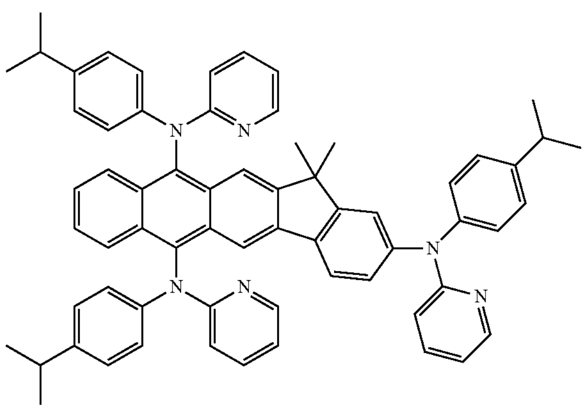

-continued
Inv-3-59
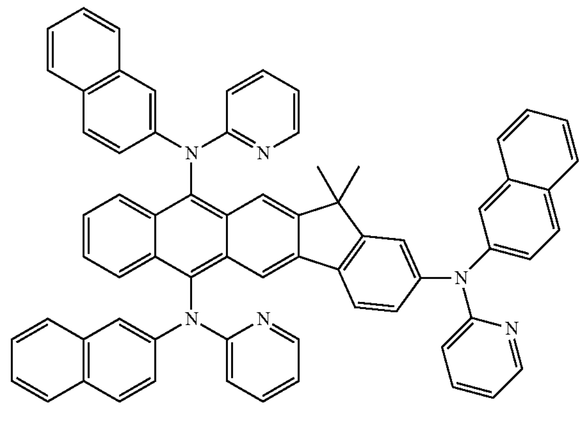
Inv-3-60
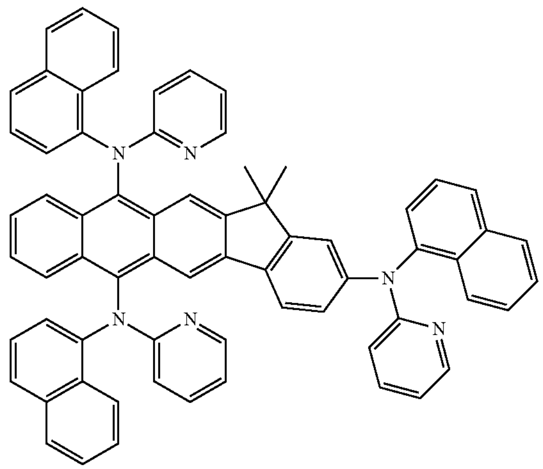
Inv-3-61
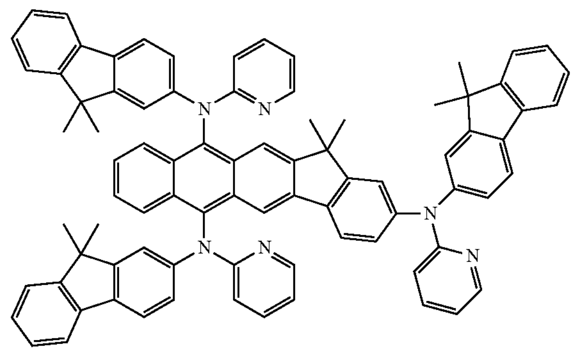
Inv-3-62
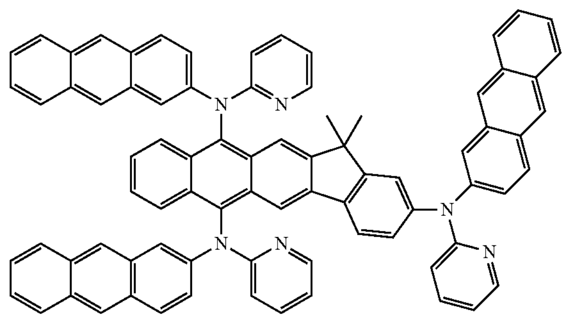
Inv-3-63
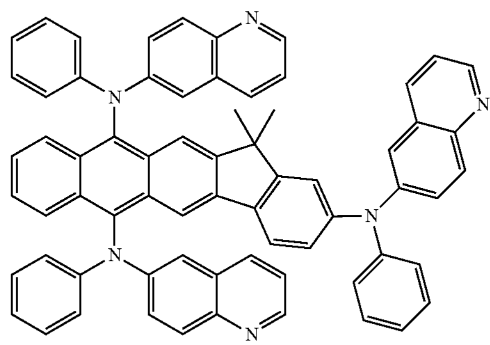
Inv-3-64
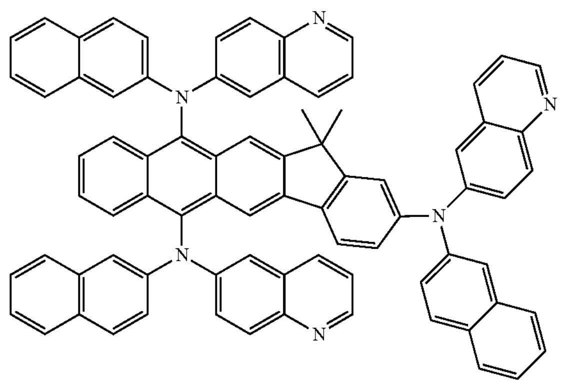

-continued
Inv-3-65
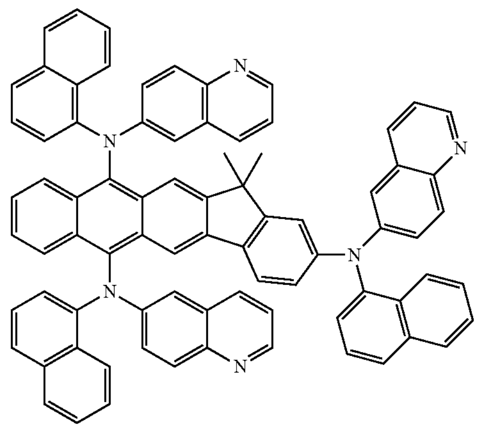
Inv-3-66
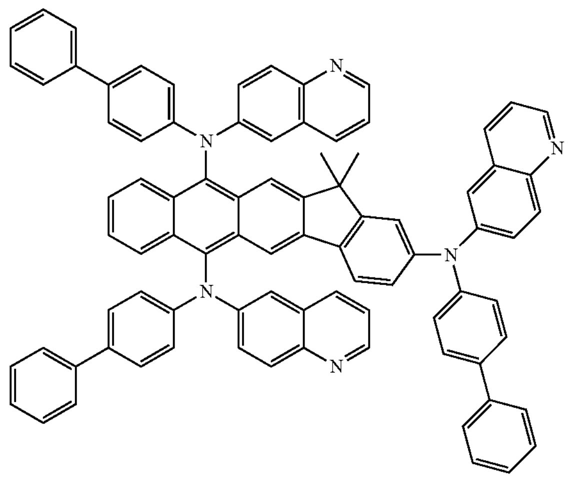
Inv-3-67
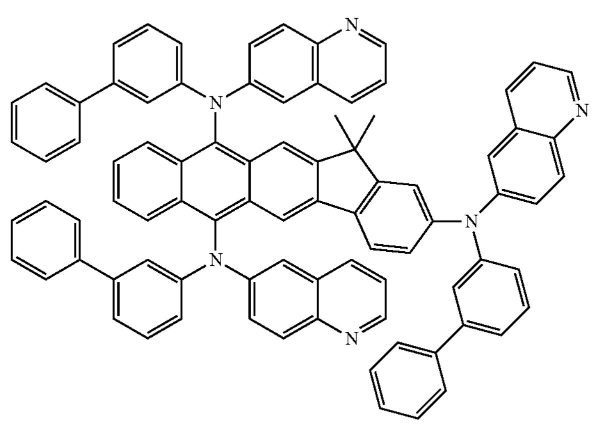
Inv-3-68
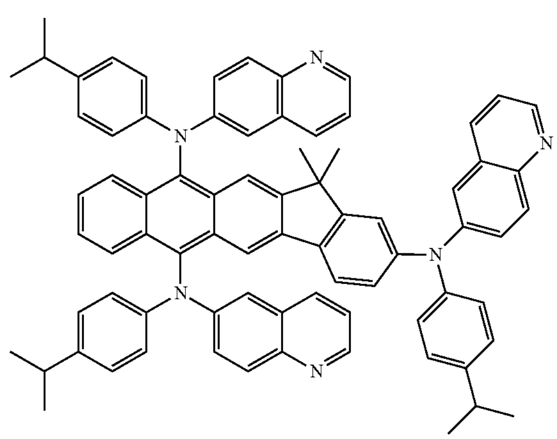
Inv-3-69
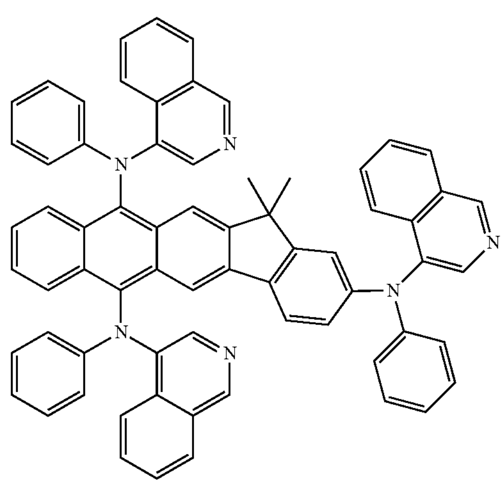
Inv-3-70
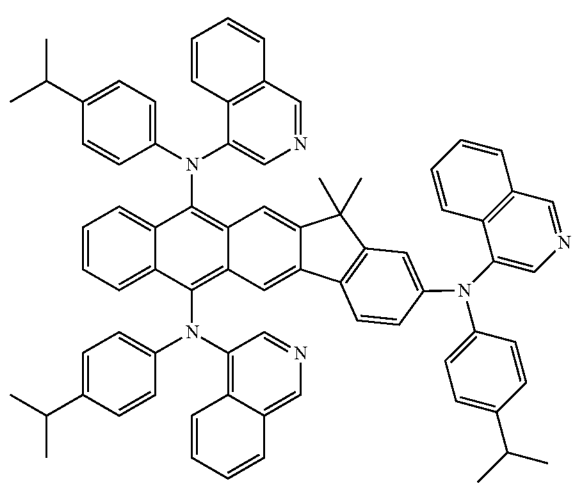

-continued
Inv-3-71
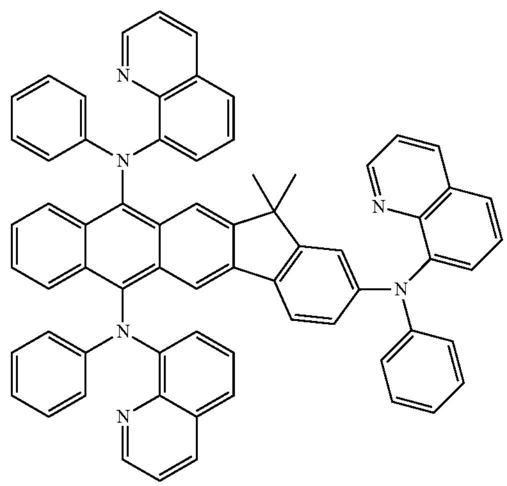
Inv-3-72
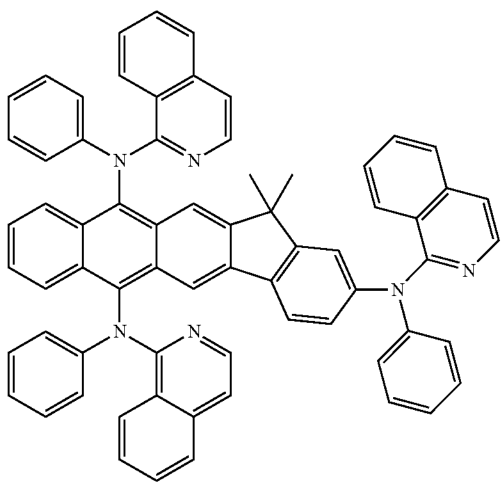
Inv-3-73
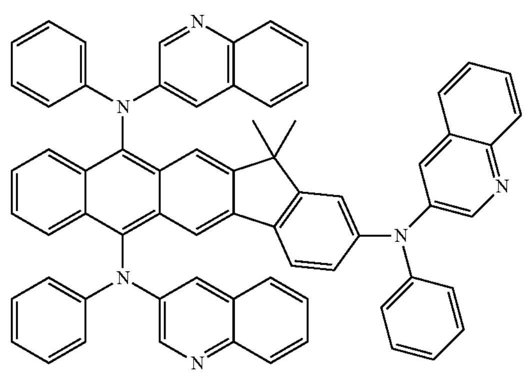
Inv-3-74
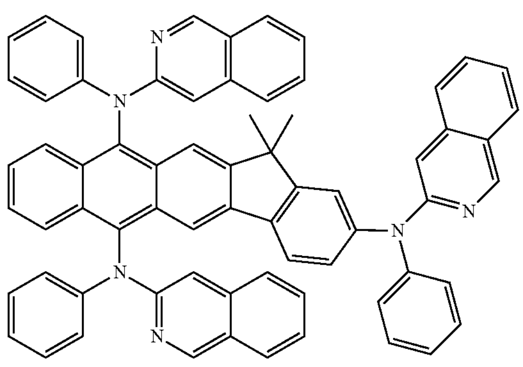
Inv-3-75
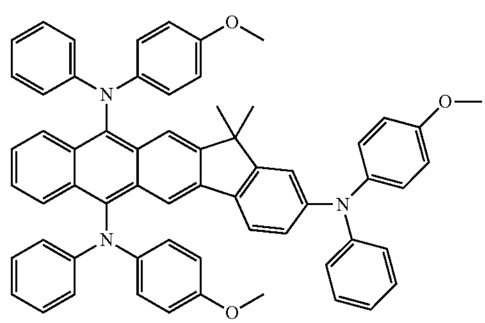
Inv-3-76
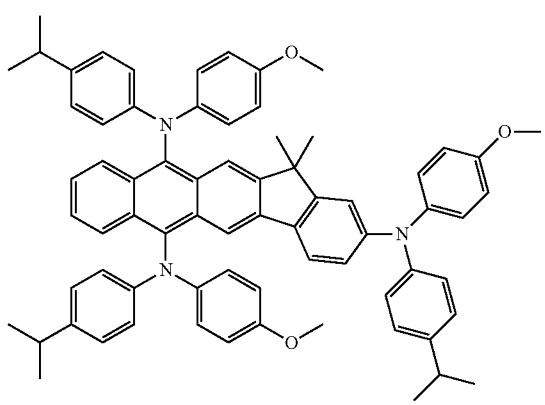

-continued
Inv-3-77
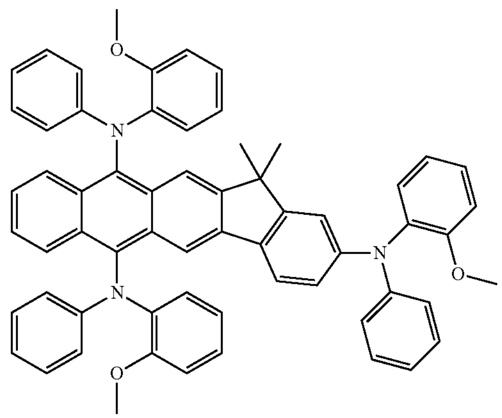
Inv-3-78
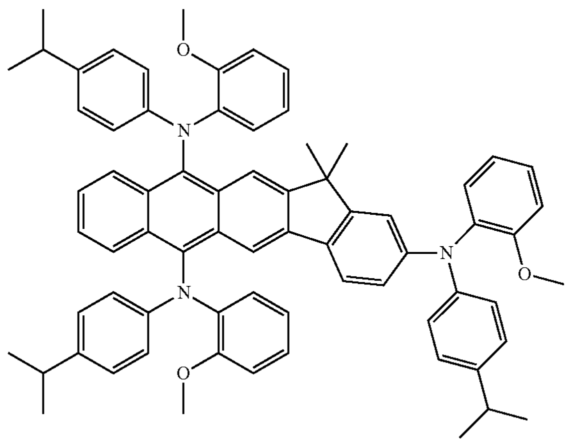
Inv-3-79
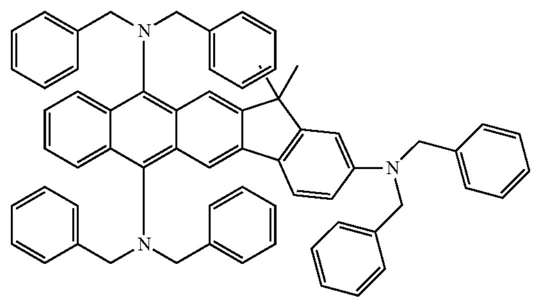
Inv-4-1
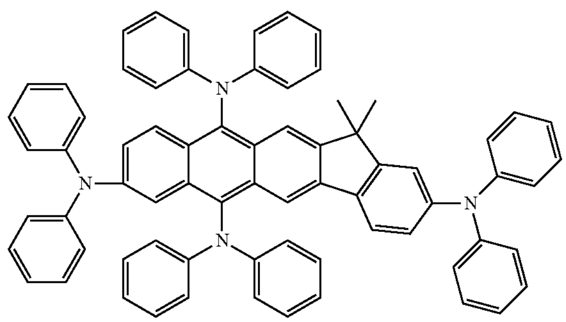
Inv-4-2
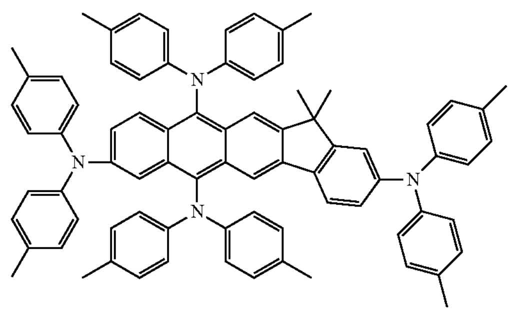
Inv-4-3
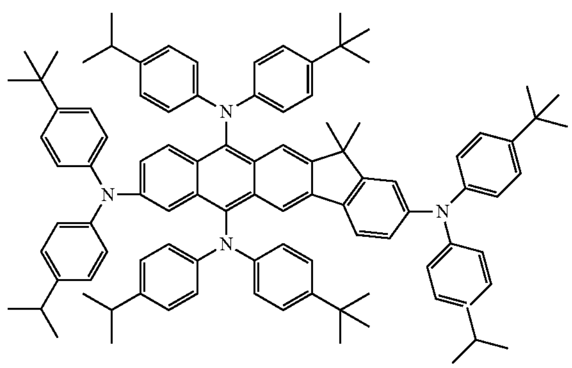
Inv-4-4
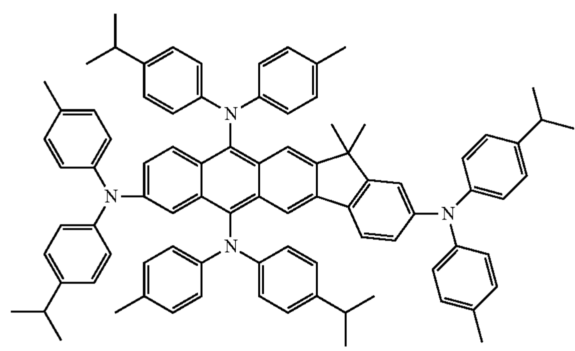
Inv-4-5
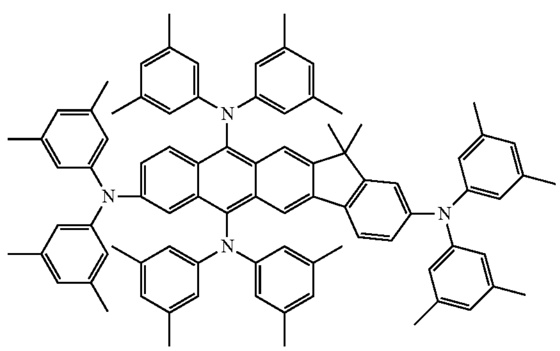

-continued
Inv-4-6
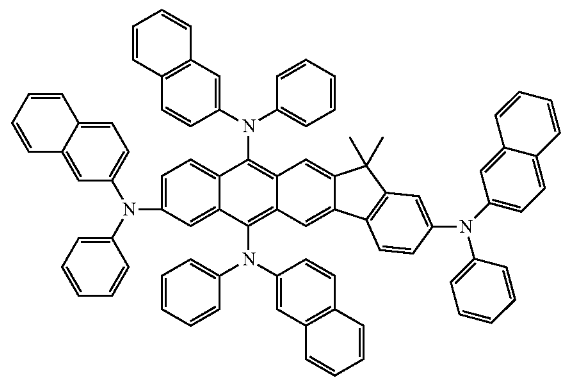
Inv-4-7
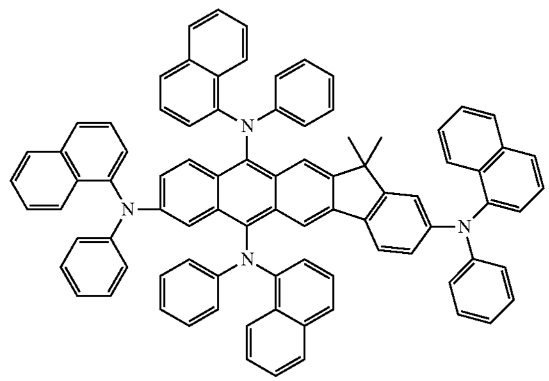
Inv-4-8
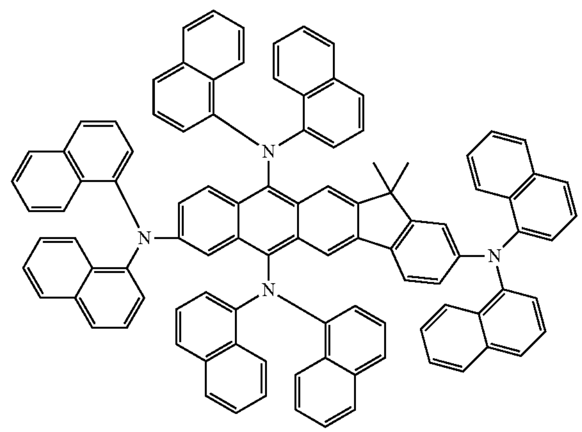
Inv-4-9
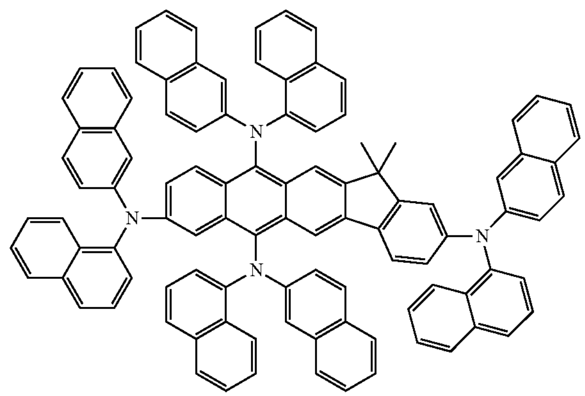
Inv-4-10
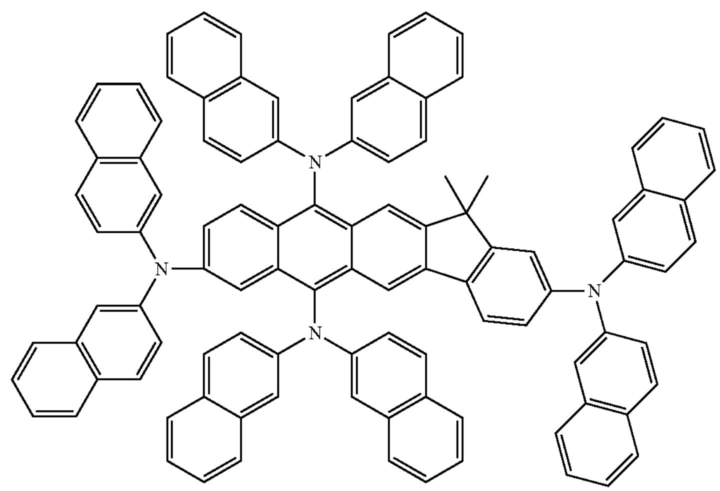

-continued
Inv-4-11
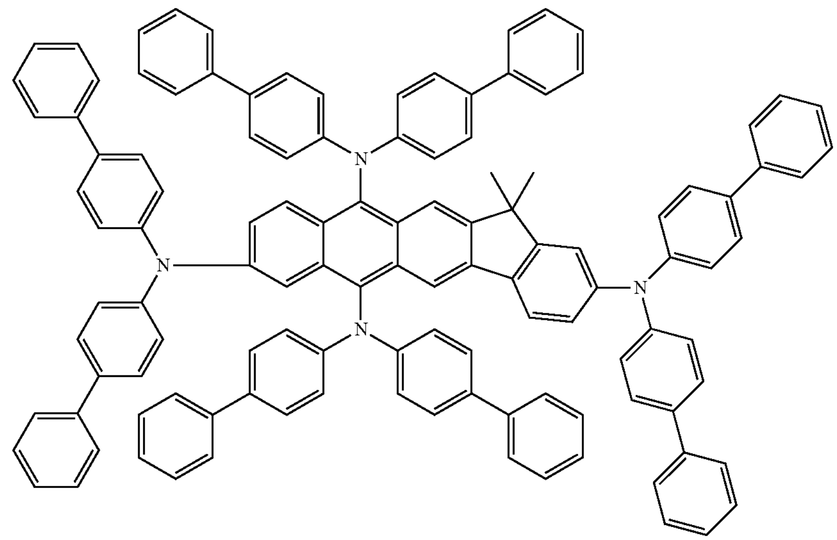
Inv-4-12
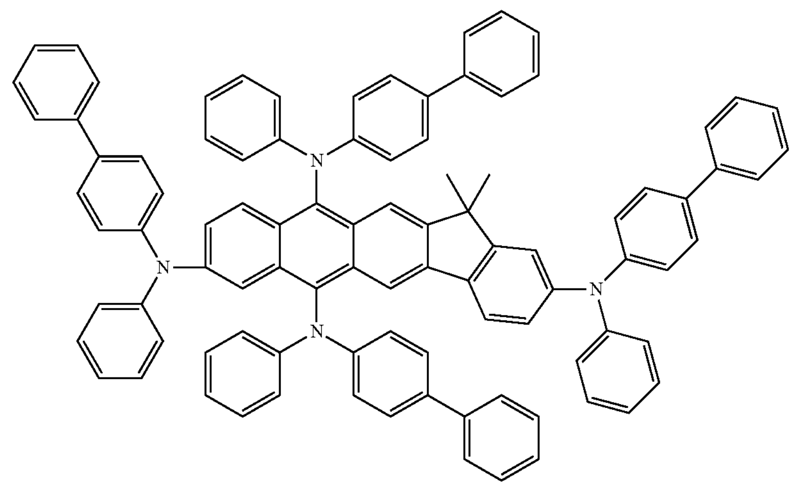
Inv-4-13
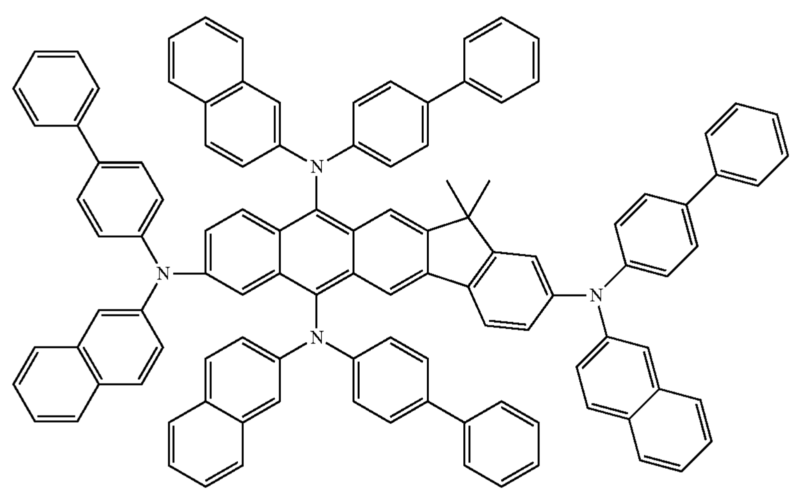

-continued
Inv-4-14
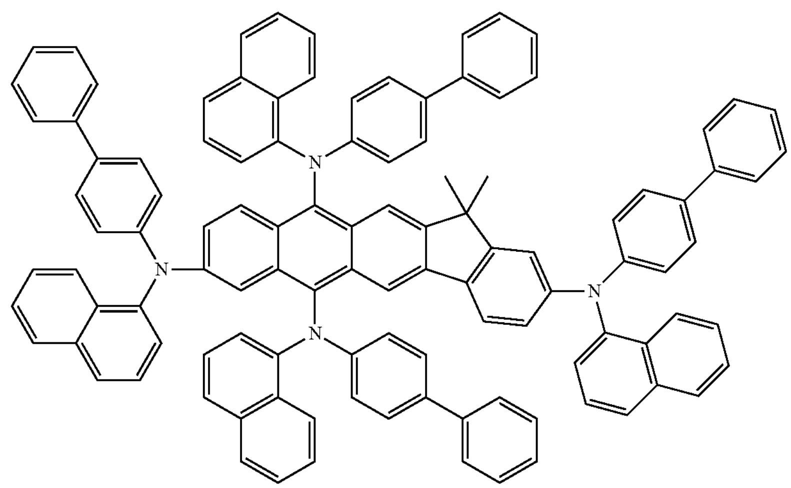
Inv-4-15
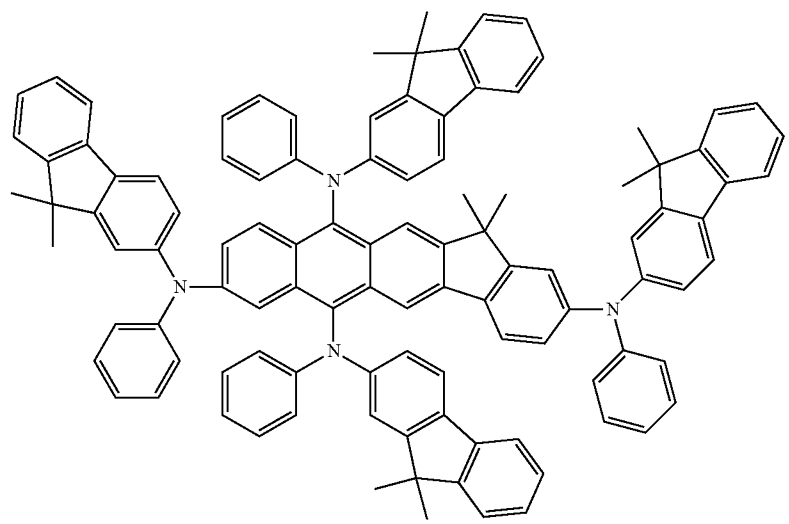
Inv-4-16
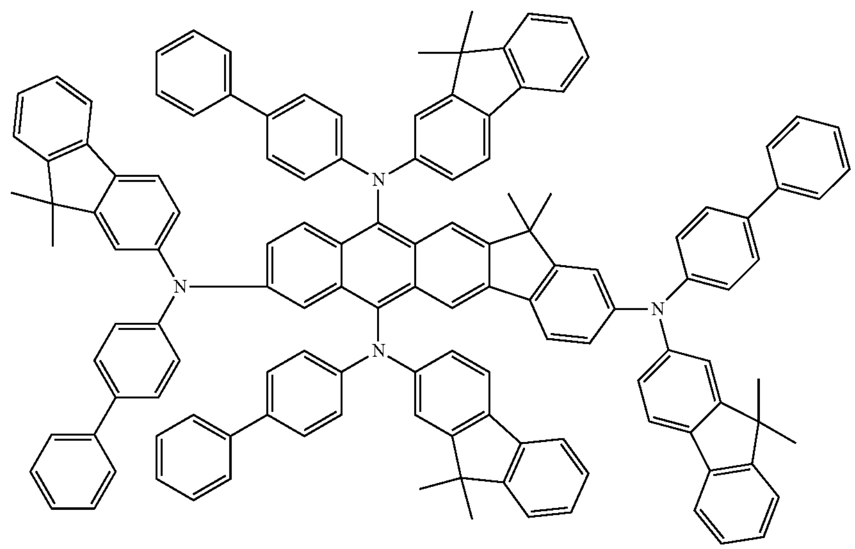

-continued
Inv-4-17
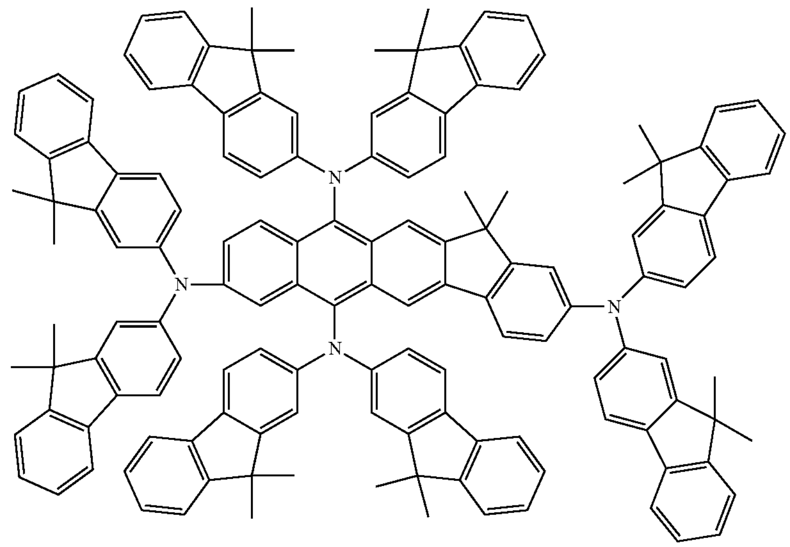
Inv-4-18
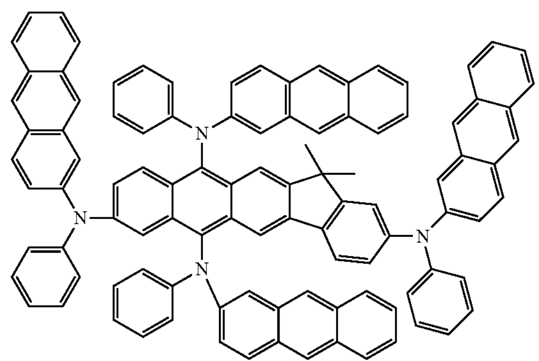
Inv-4-19
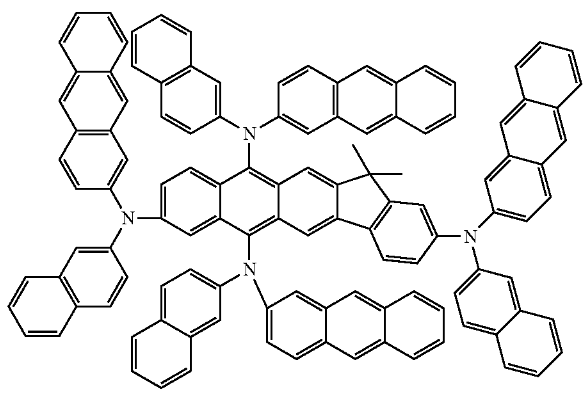
Inv-4-20
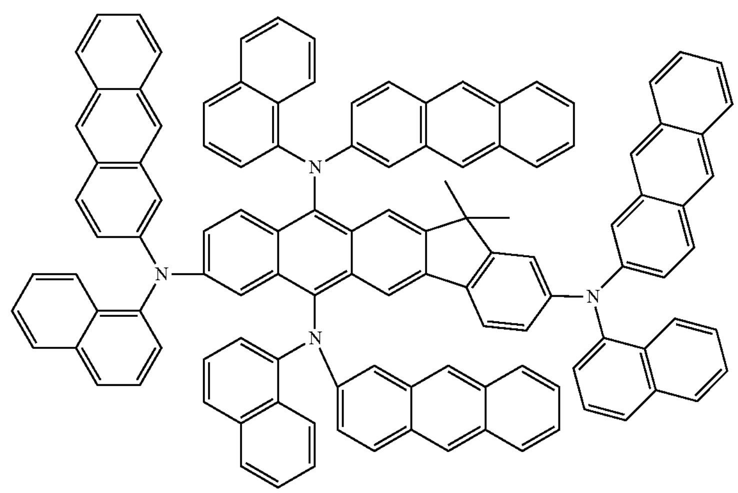

-continued
Inv-4-21
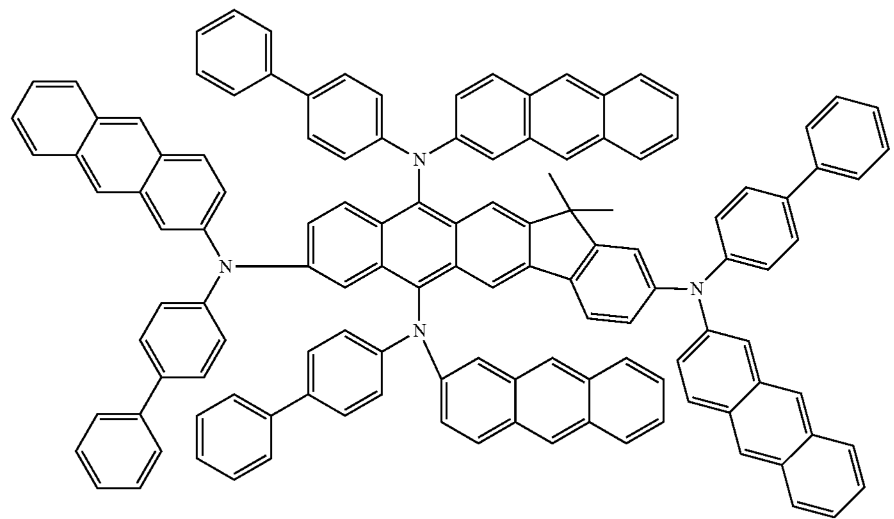
Inv-4-22
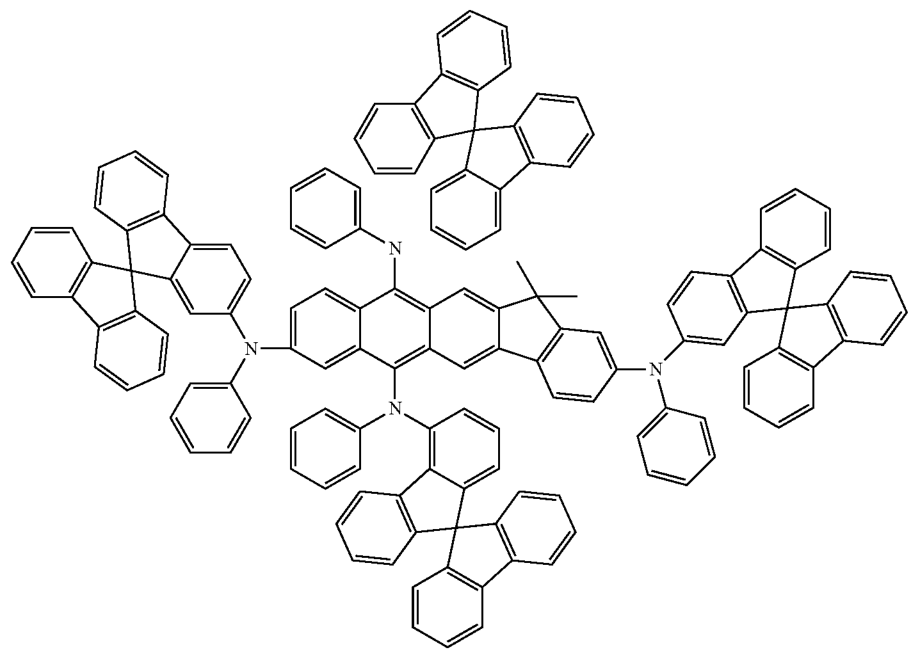

-continued
Inv-4-23
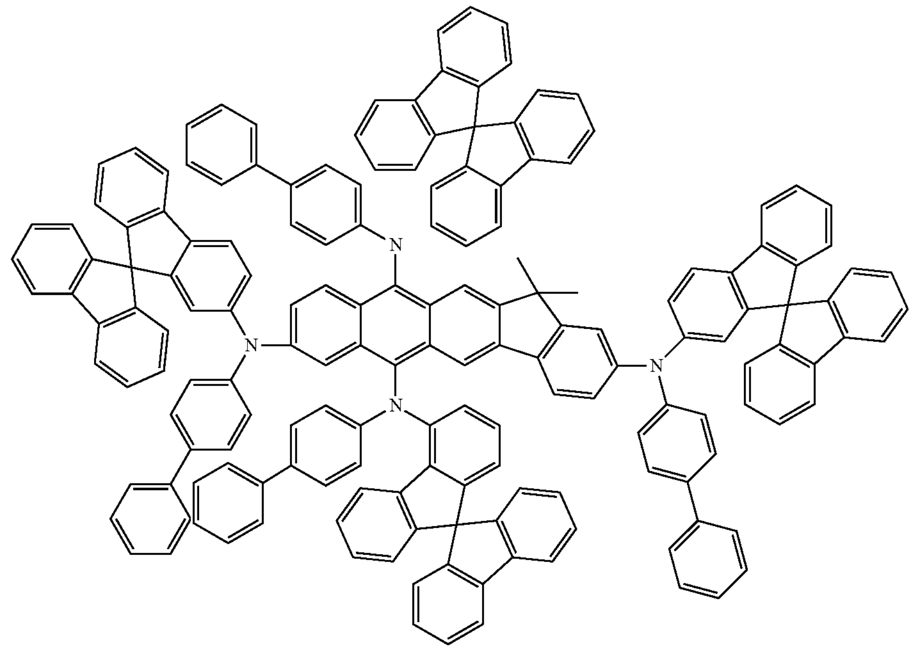
Inv-4-24
Inv-4-25
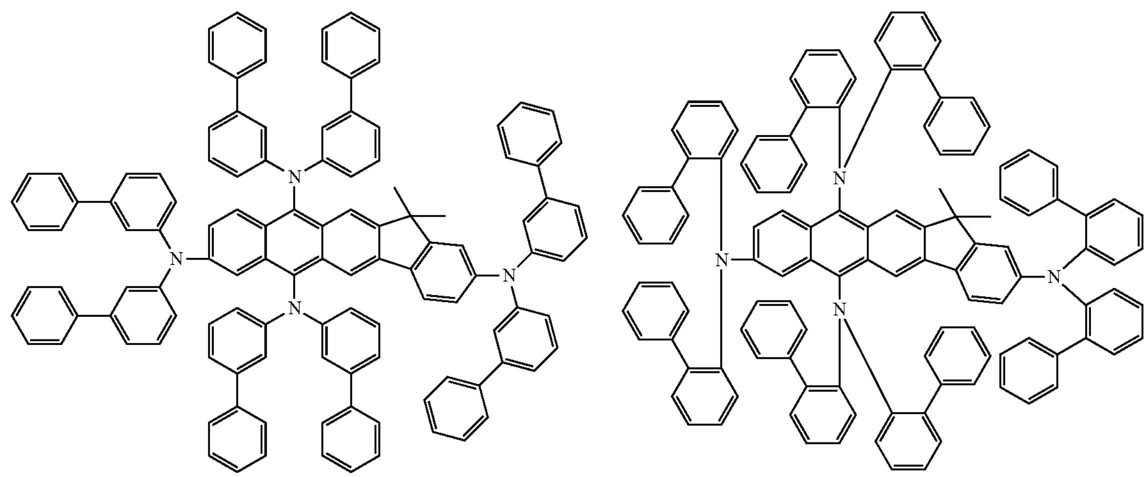
Inv-4-26
Inv-4-27
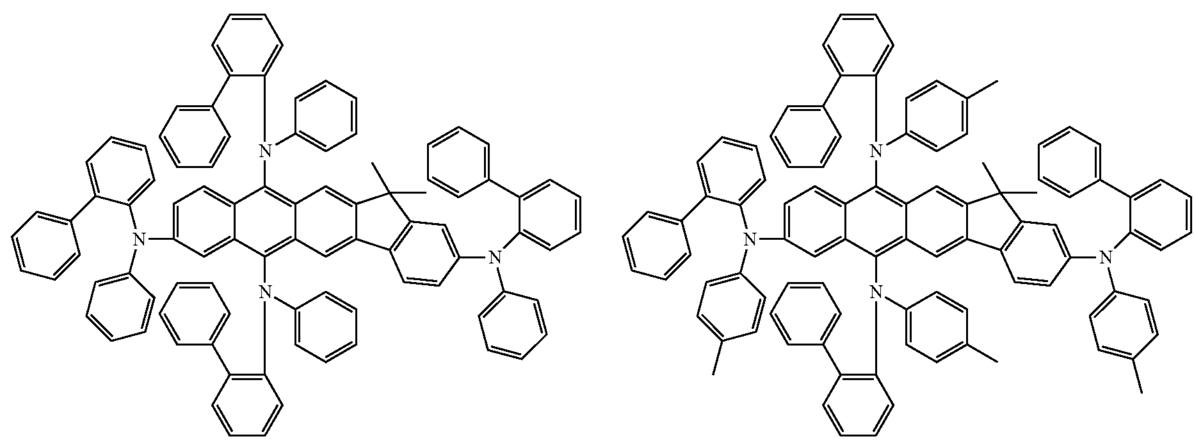

-continued
Inv-4-28
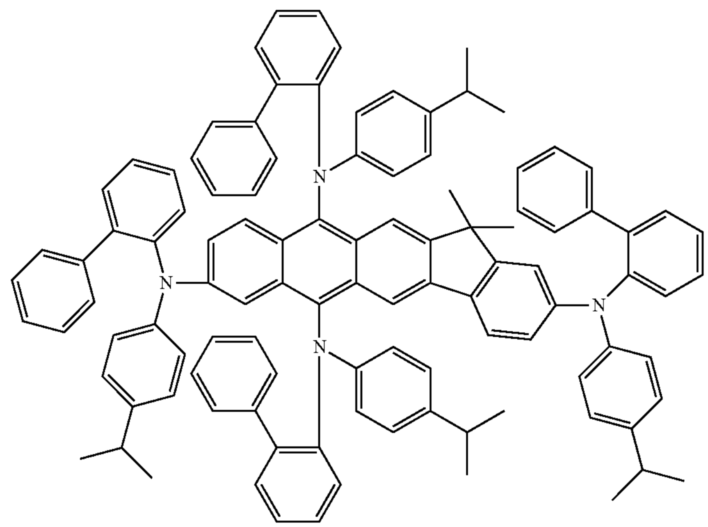
Inv-4-29
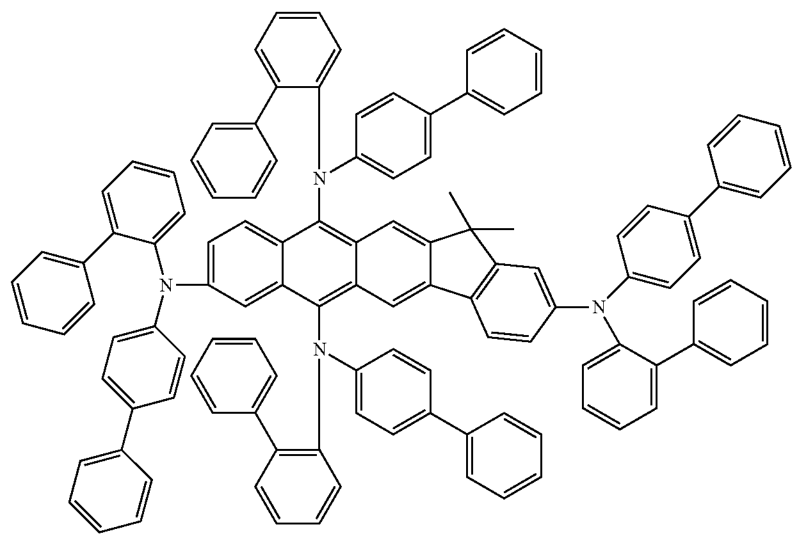
Inv-4-30
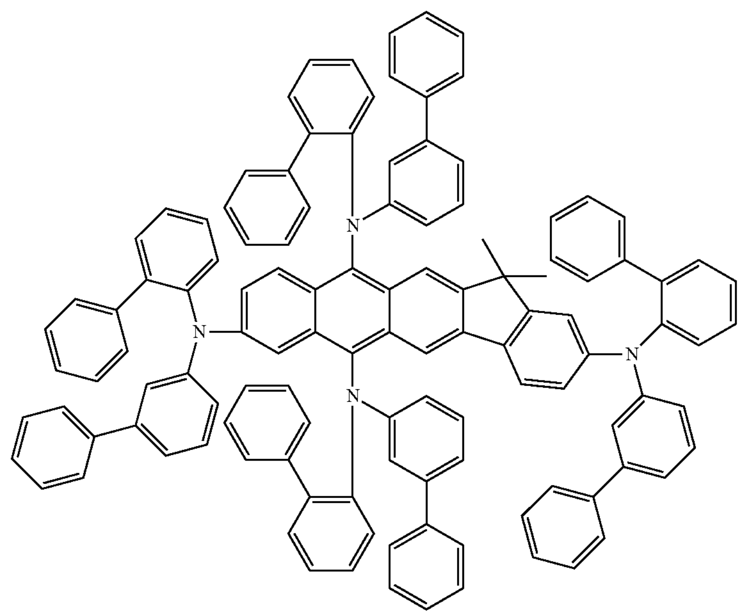

-continued
Inv-4-31
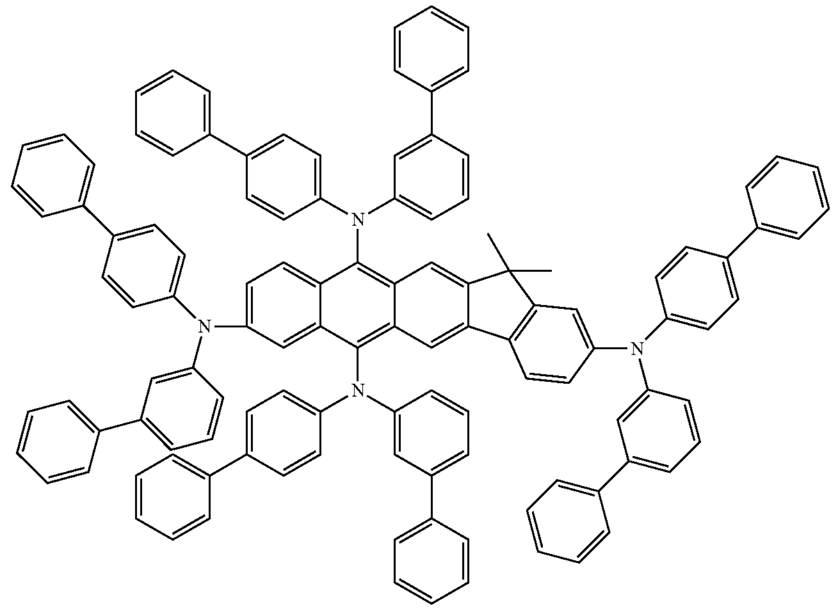
Inv-4-32
Inv-4-33
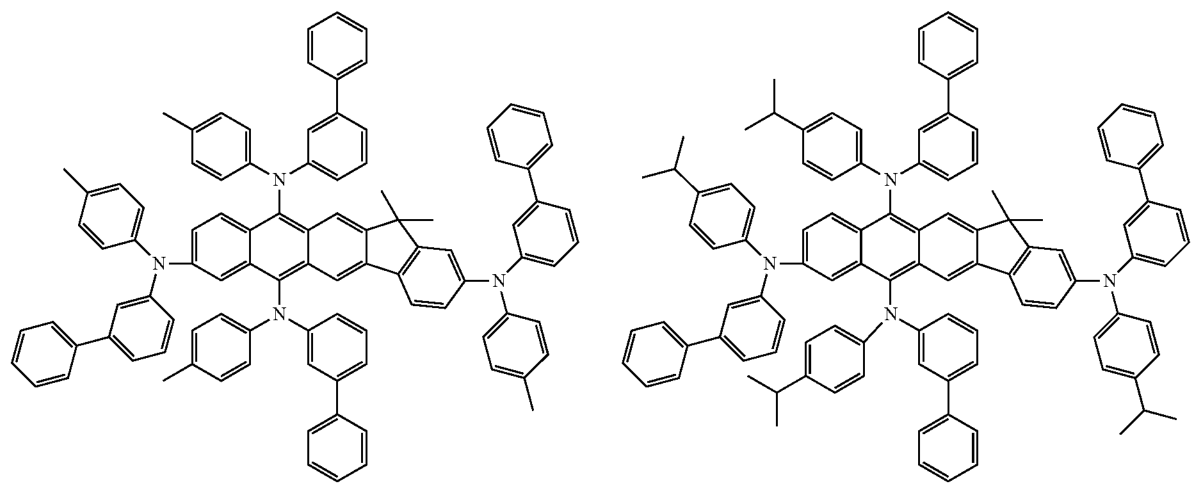
Inv-4-34
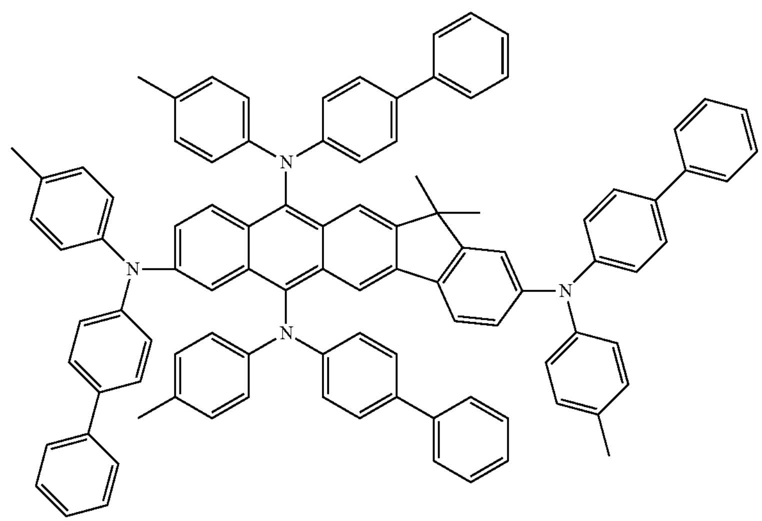

-continued
Inv-4-35
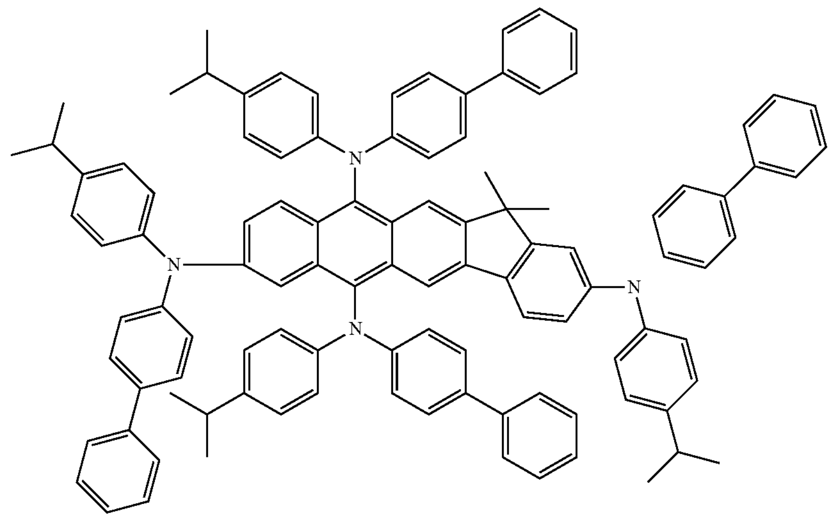
Inv-4-36
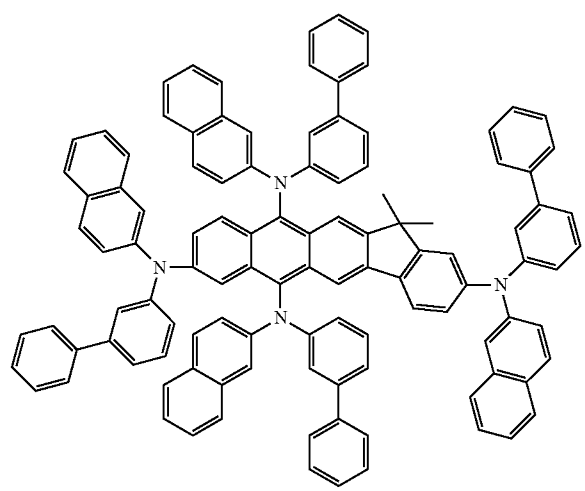
Inv-4-37
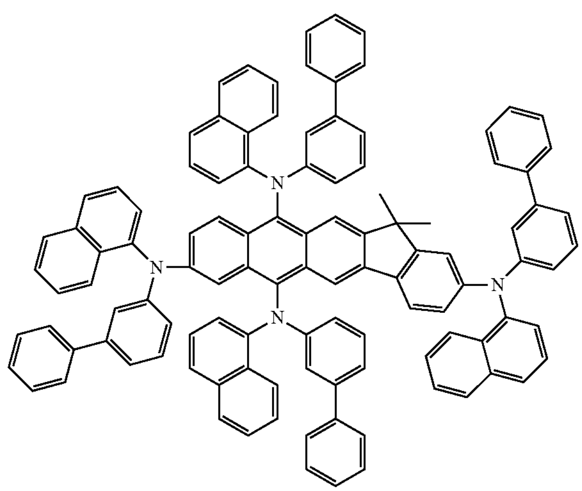
Inv-4-38
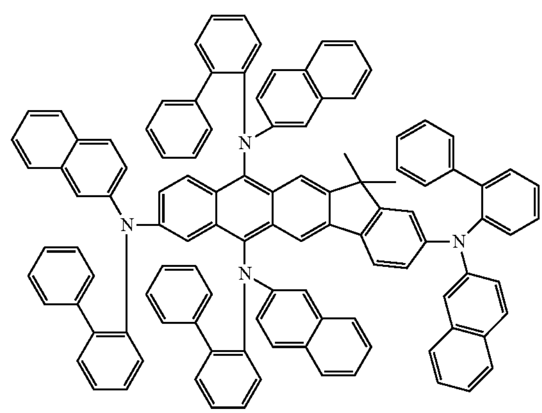
Inv-4-39
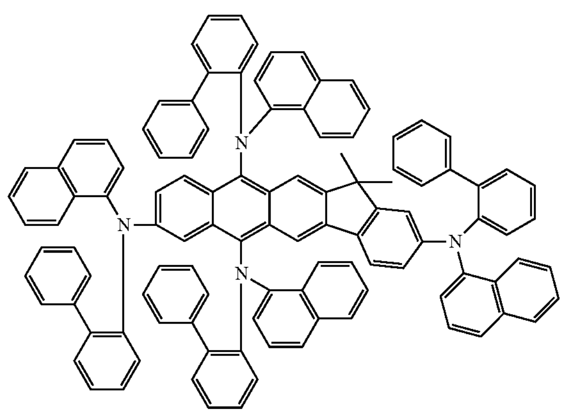

-continued
Inv-4-40
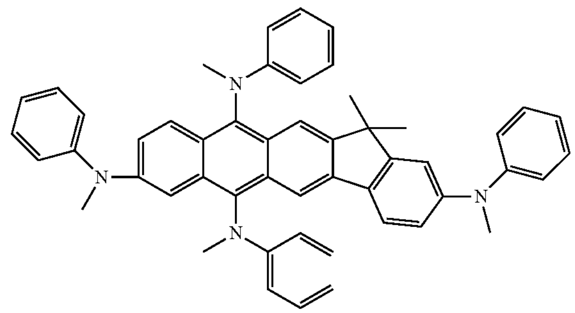
Inv-4-41
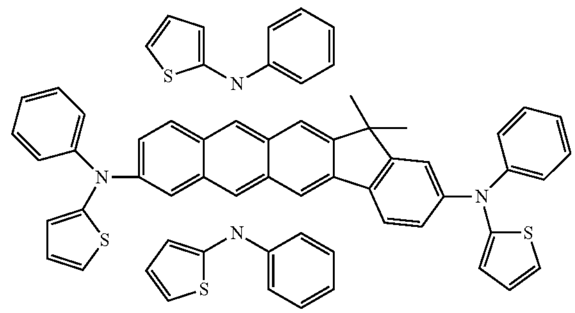
Inv-4-42
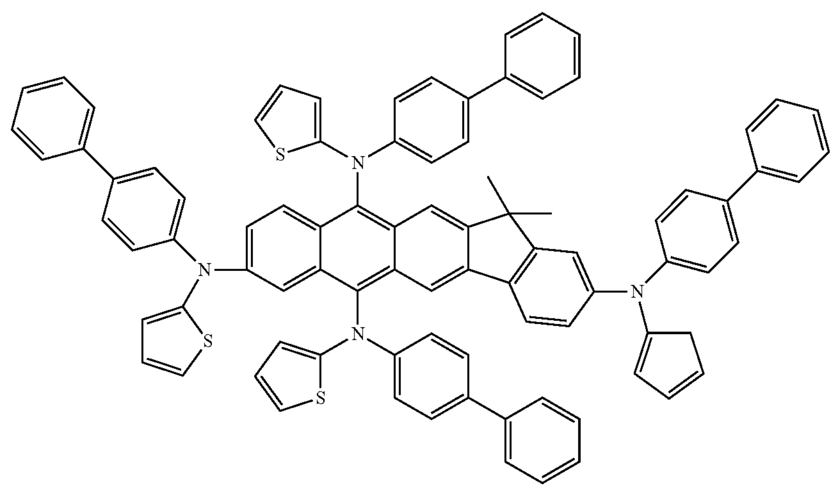
Inv-4-43
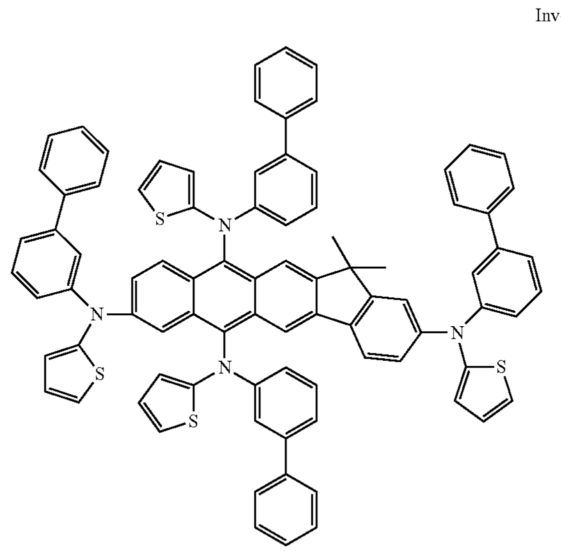
Inv-4-44
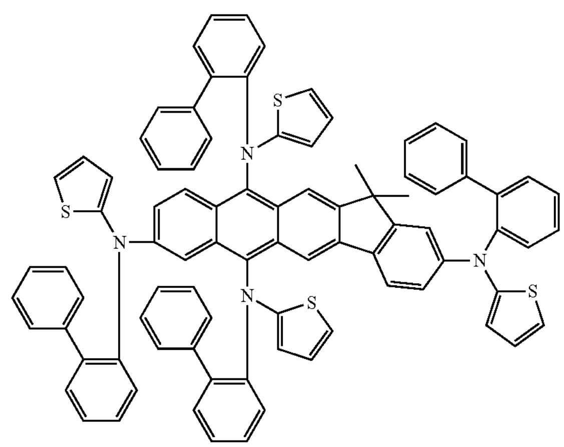

-continued
Inv-4-45
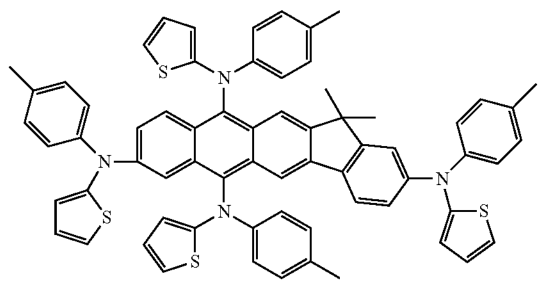
Inv-4-46
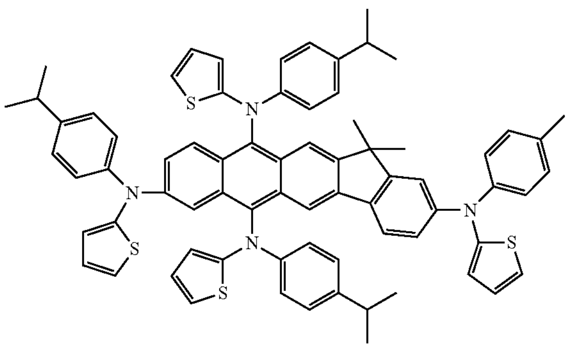
Inv-4-47
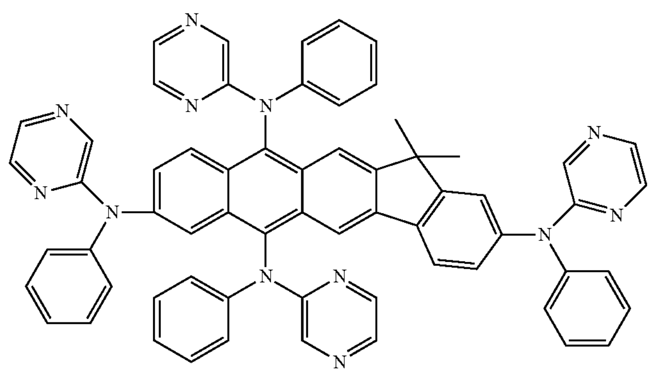
Inv-4-48
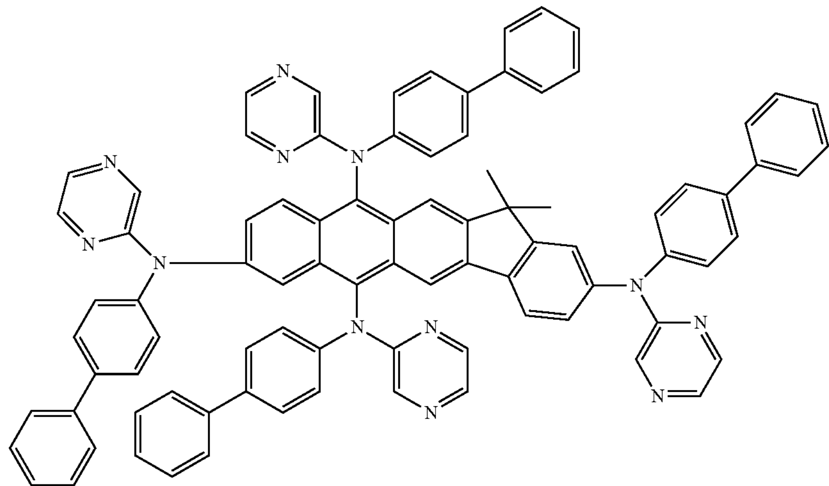

-continued
Inv-4-49
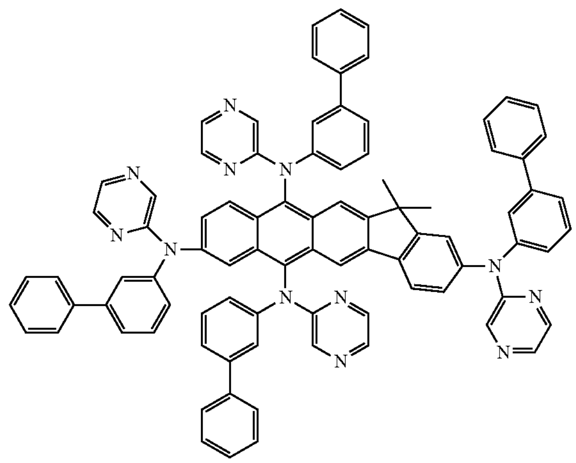
Inv-4-50
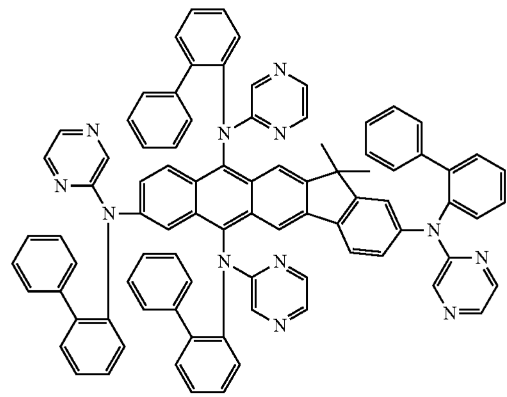
Inv-4-51
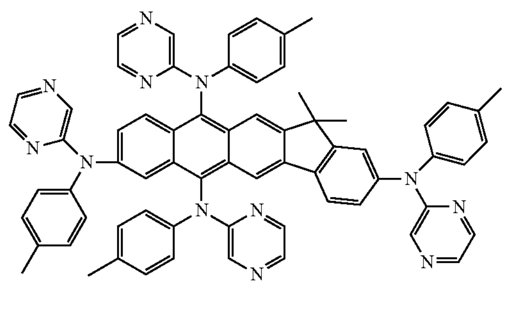
Inv-4-52
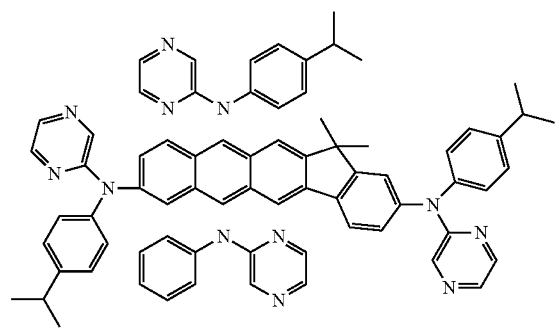
Inv-4-53
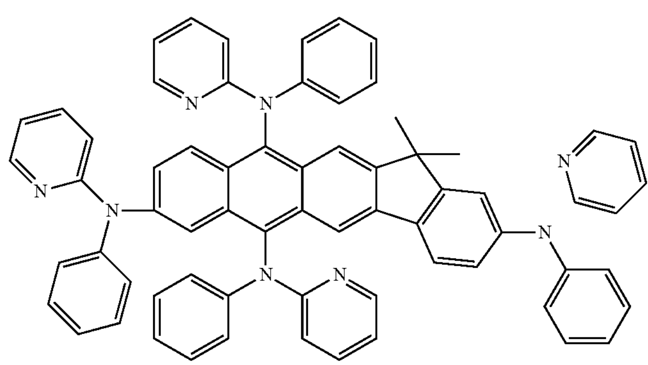

-continued
Inv-4-54
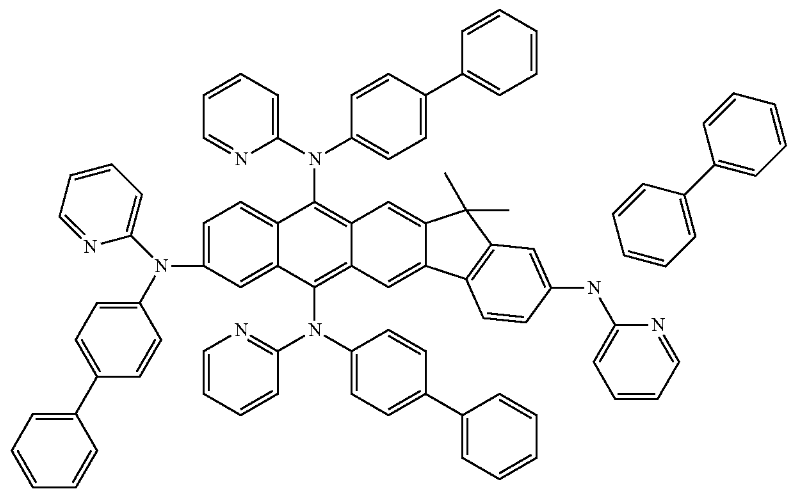
Inv-4-55
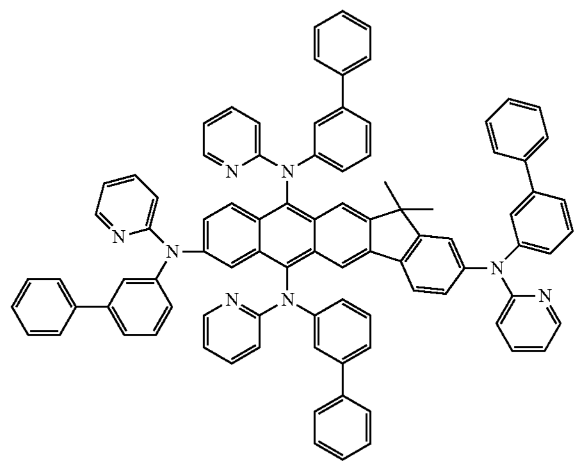
Inv-4-56
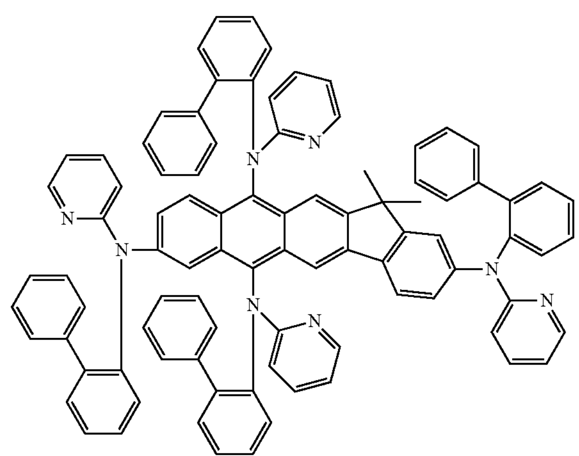
Inv-4-57
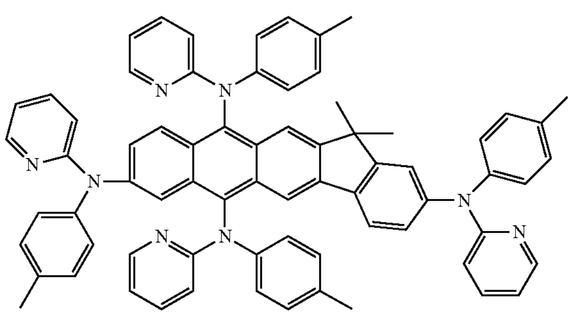

-continued
Inv-4-58
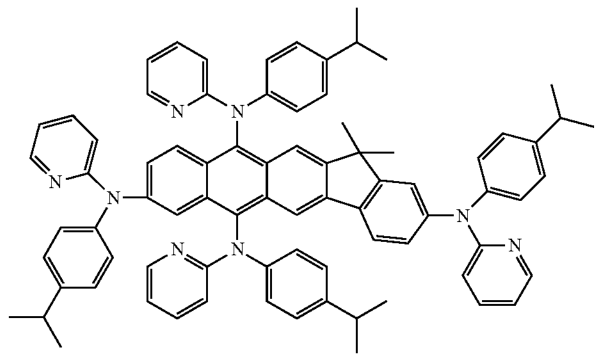
Inv-4-59
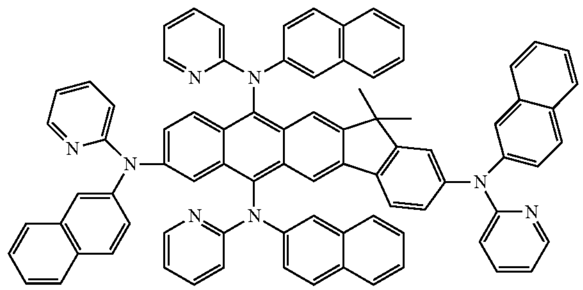
Inv-4-60
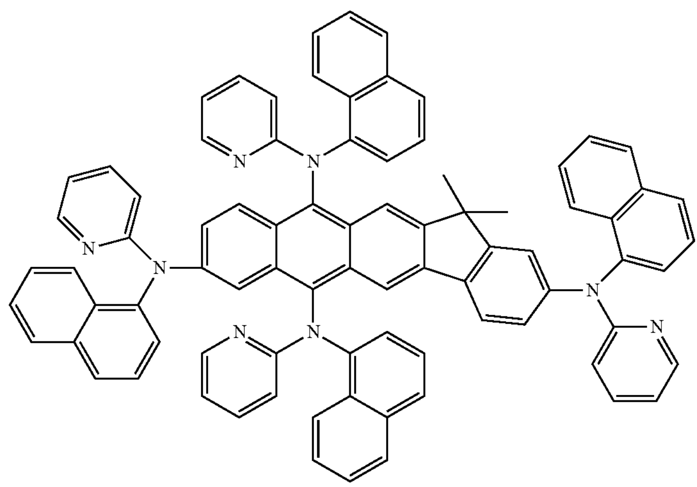
Inv-4-61
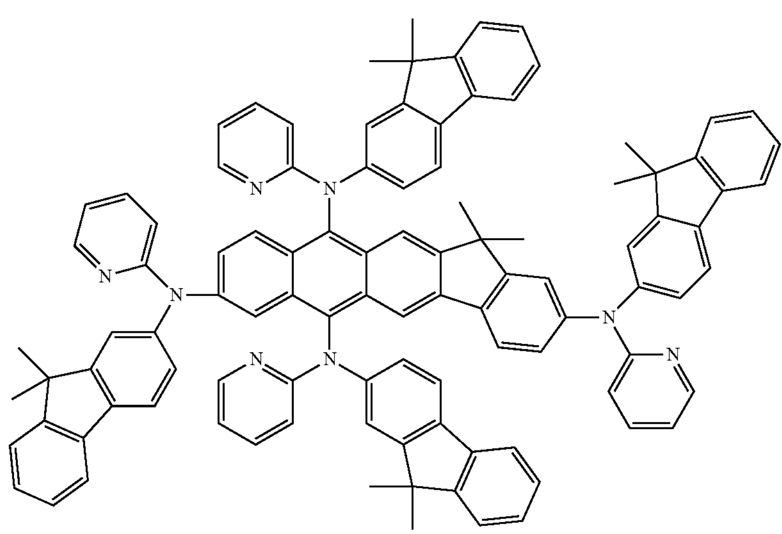

-continued
Inv-4-62
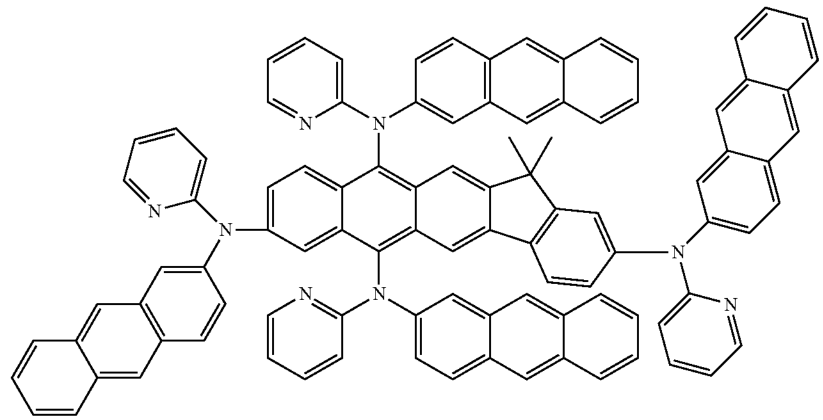
Inv-4-63
Inv-4-64
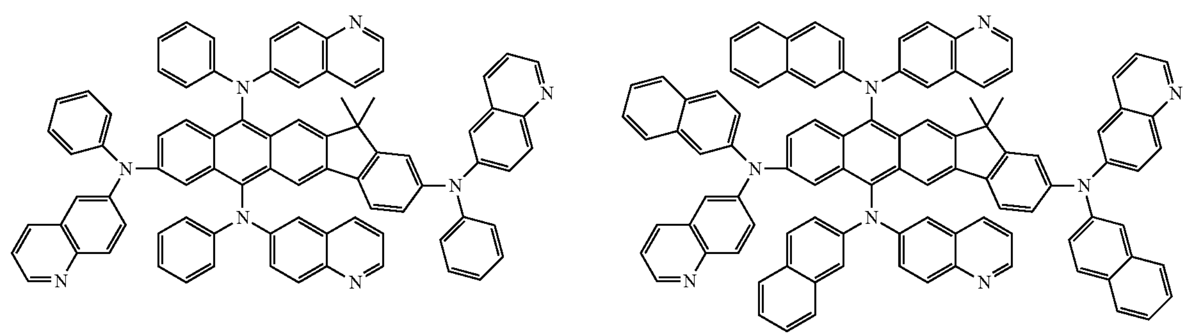
Inv-4-65
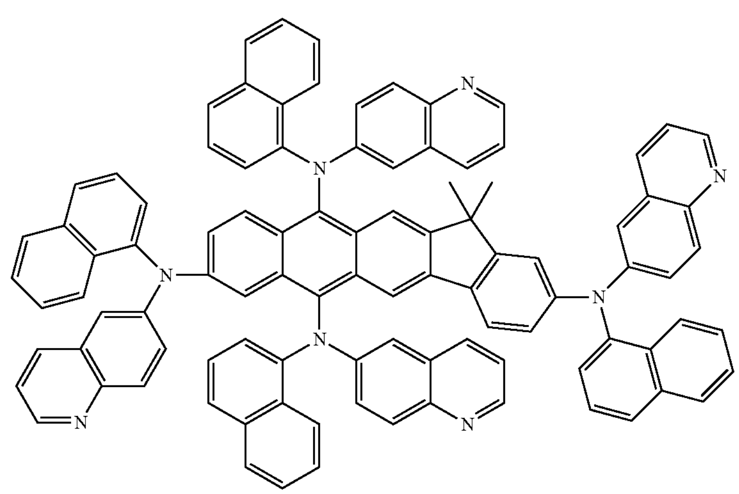

-continued
Inv-4-66
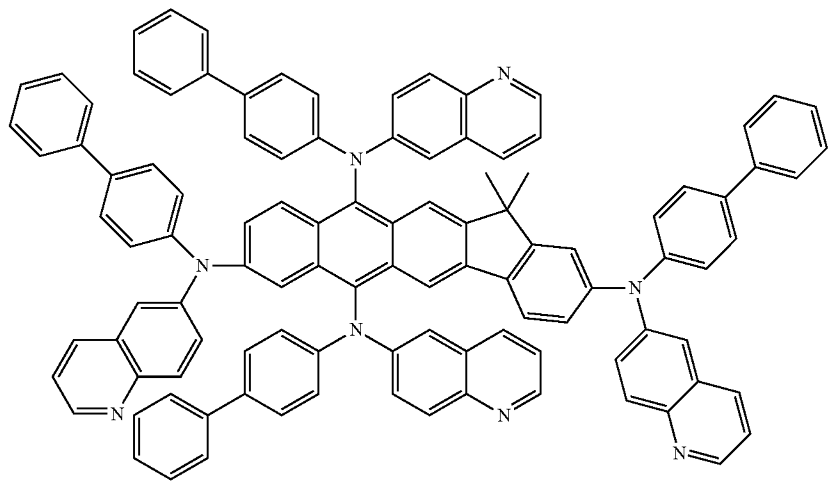
Inv-4-67
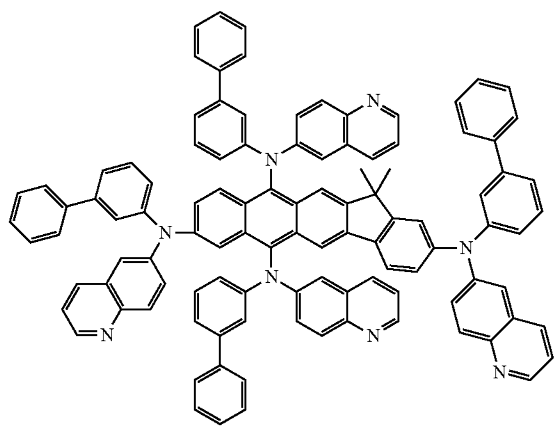
Inv-4-68
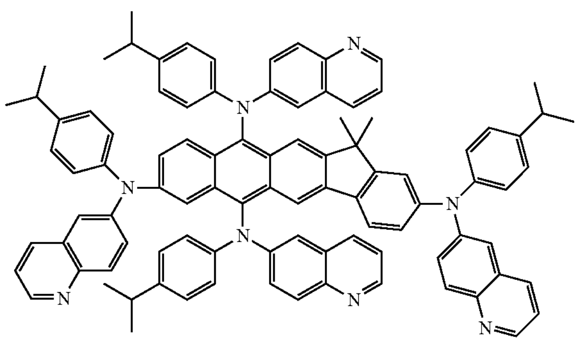
Inv-4-69
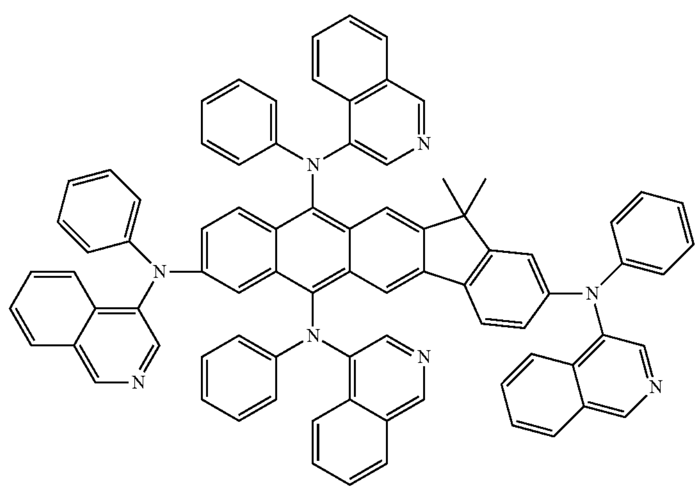

-continued
Inv-4-70
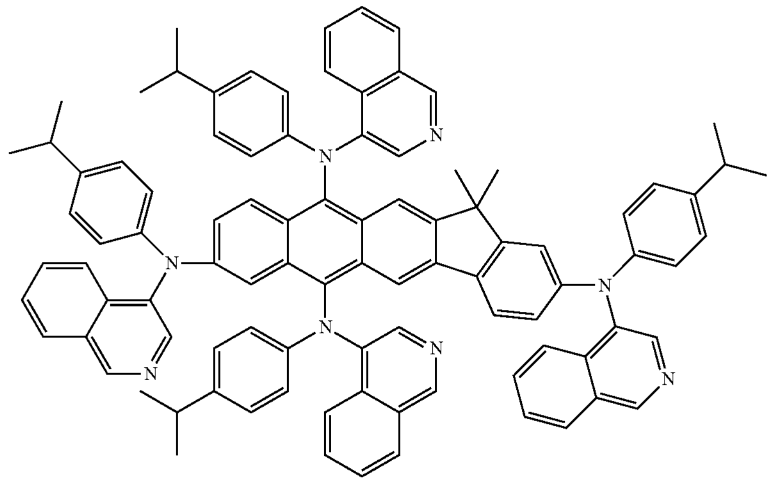
Inv-4-71
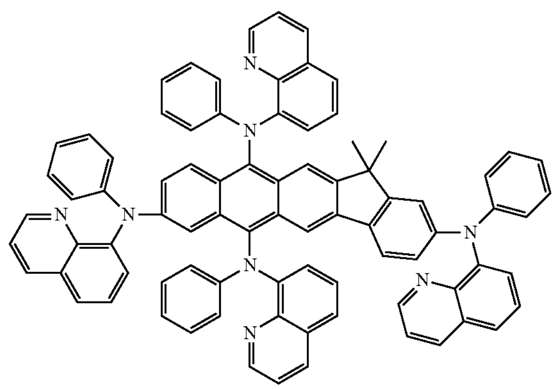
Inv-4-72
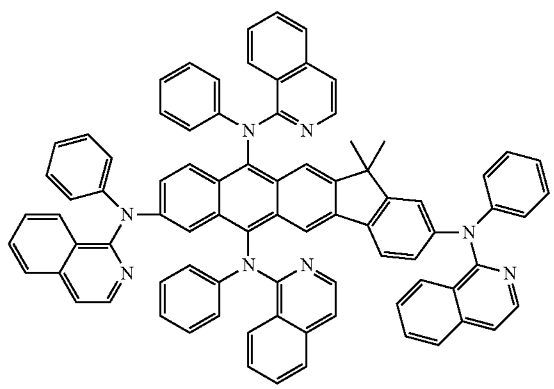
Inv-4-73
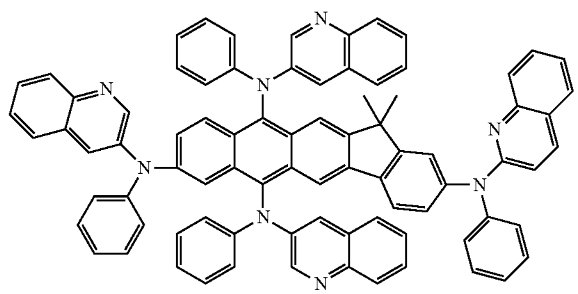
Inv-4-74
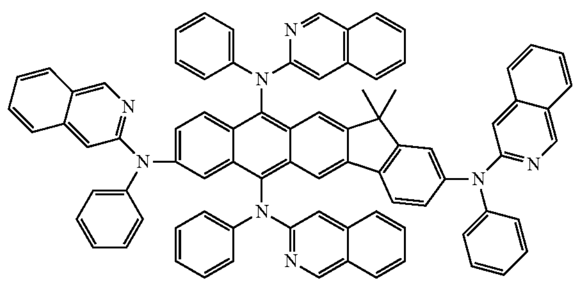
Inv-4-75
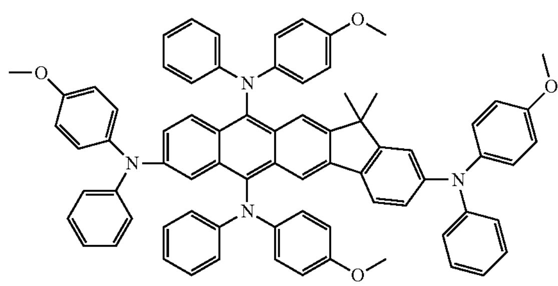
Inv-4-76
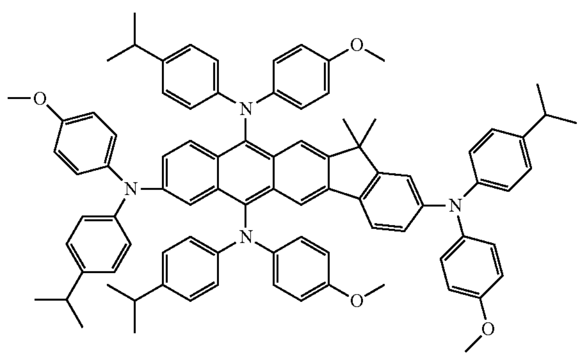

-continued

Inv-4-77

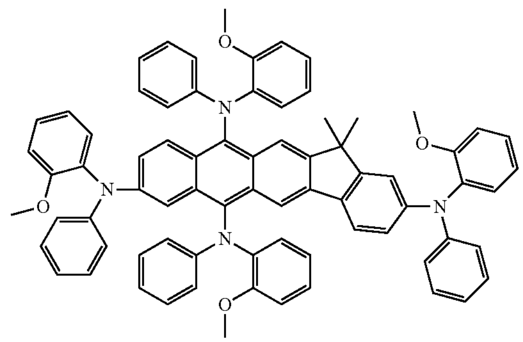

Inv-4-78

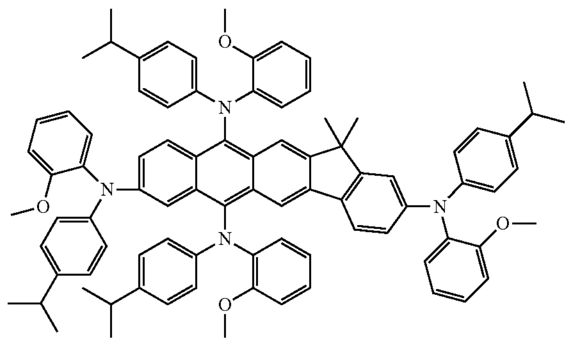

Inv-4-79

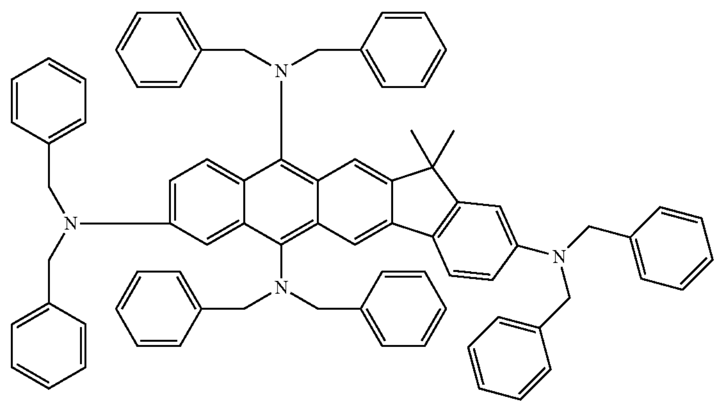

Another aspect of the present invention relates to an organic light emitting layer including the present invention compound represented by Formula 1.

A further aspect of the present invention relates to an organic electro-luminescence device including the present invention compound represented by Formula 1.

Specifically, the present invention organic electro-luminescence device includes (i) an anode; (ii) a cathode; and (iii) one or more organic material layers intervened between the anode and the cathode, wherein at least one layer of the organic material layers includes the compound represented by Formula 1.

The organic material layer including the compound represented by Formula 1 of the present invention may include one or more of a hole injection layer, a hole transport layer, a light emitting layer, an electron transport layer, and an electron injection layer. Preferably, the compound represented by Formula 1 may be included as a light emitting layer material in the organic electro-luminescence device. In this case, the organic electro-luminescence device may be enhanced in luminous efficiency, brightness, power efficiency, thermal stability, and device life span. Accordingly, the organic material layer including the compound represented by Formula 1 is preferably a light emitting layer.

Also, the organic electro-luminescence device according to the present invention may include, the organic material layer including the compound represented by Formula 1 of the present invention, other organic material layers such as a hole injection layer, a hole transport layer, a light emitting layer, and/or an electron transport layer.

As a non-limiting example, the inventive organic electro-luminescence device may be structured such that a substrate, an anode, a hole injection layer, a hole transport layer, a light-emitting layer, an electron transport layer and a cathode are sequentially stacked one onto another. Herein, the light emitting layer includes the compound represented by Formula 1. On the electron transport layer, an electron injection layer may also be disposed.

The present invention organic electro-luminescence device may also be structured such that an anode, one or more organic material layers and a cathode are sequentially stacked, as described above, and an insulating layer or an adhesive layer is interposed between an electrode and an organic material layer.

In the present invention organic electro-luminescence device, the organic material layer including the compound represented by Formula 1 may be formed by vacuum deposition or solution coating. Examples of the solution coating include spin coating, dip coating, doctor blading, inkjet printing, thermal transfer, etc., but are not limited thereto.

In the present invention organic electro-luminescence device, organic material layers and electrodes may be formed of materials known in the art using a method known in the art except that at least one layer of the organic material layers includes the compound represented by Formula 1 of the present invention.

For example, a substrate may be a silicon wafer, quartz, a glass plate, a metal plate, a plastic film or sheet, etc.

An anode material may be a metal such as vanadium, chromium, copper, zinc, or gold, or an alloy thereof; metal oxide such as zinc oxide, indium oxide, indium tin oxide (ITO), indium zinc oxide (IZO); a metal-oxide complex such as ZnO:Al or $SnO_2$:Sb; a conductive polymer such as polythiophene, poly(3-methylthiophene), poly[3,4-(ethylene-1,2-dioxy)thiophene] (PEDT), polypyrrole and polyaniline; carbon black, etc., but is not limited thereto.

A cathode material may be a metal such as magnesium, calcium, sodium, potassium, titanium, indium, yttrium, lithium, gadolinium, aluminum, silver, tin or lead, or an alloy thereof; a multi-layered material such as LiF/Al or $LiO_2$/Al, but is not limited thereto.

Materials for a hole injection layer, a hole transport layer, and an electron transport layer are not particularly limited, and may be materials commonly known in the art.

Hereinafter, the present invention will be described more specifically with reference to the following examples. The following examples are only for illustrative purposes and are not intended to limit the scope of the invention.

Synthesis Example 1

Preparation of 2-(9,9-dimethyl-9H-fluorene-2-carbonyl)benzoic acid

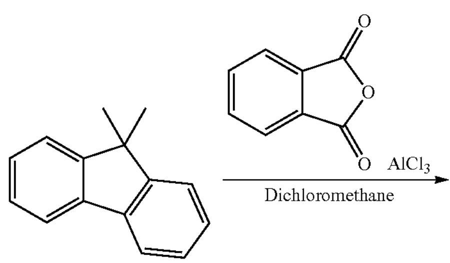

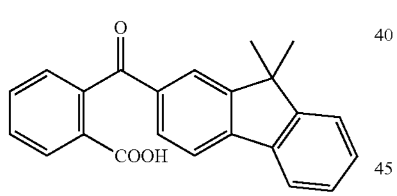

9,9-dimethyl-9H-fluorene (40 g, 1 eq, 0.206 mol) and Phthalic anhydride (33.6 g, 1.1 eq, 0.227 mol) were placed in a reaction vessel, and added with Dichloromethane (1.5 l). At 0° C., aluminum chloride (40.8 g, 1.5 eq, 0.309 mol) was gradually added thereto, and the temperature was raised up to room temperature. Then, the resultant mixture was stirred for 12 hours. After the reaction was completed, the resultant product was gradually added with distilled water at 0° C. The resultant product was extracted with an excess of dichloromethane, and washed several times with distilled water. After solvent removal, the produced solid was placed in a Hexane 2 l-containing vessel, washed, filtered, and dried, 2-(9,9-dimethyl-9H-fluorene-2-carbonyl)benzoic acid (56.4 g, yield 82%) was obtained.

$^1$H-NMR: 1.67 (s, 6H), 7.72 (m, 5H), 7.96 (m, 5H), 8.23 (d, 1H), 12.44 (s, 1H).

Synthesis Example 2

Preparation of 13,13-dimethyl-6H-indeno[1,2-b]anthracene-6,11(13H)-dione

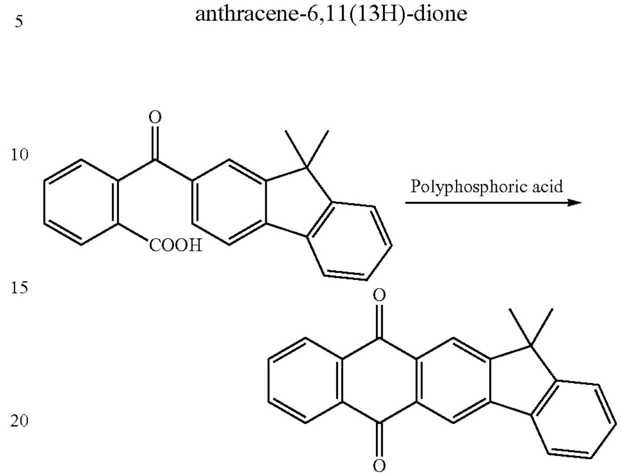

2-(9,9-dimethyl-9H-fluorene-2-carbonyl)benzoic acid (20 g, 1 eq, 0.058 mol) was placed in a flask, and polyphosphoric acid (70 ml) was added thereto. The reaction mixture was stirred at 140° C. for 2 hours while heating, and cooled to less than 50° C., and distilled water was gradually added thereto. The produced solid was filtered, washed with a small amount of methanol, and dried, 2,9-dibromo-13,13-dimethyl-6H-indeno[1,2-b]anthracene-6,11(13H)-dione (14.7 g, yield 78%) was obtained.

$^1$H NMR: 1.57 (s, 6H), 7.30 (t, 2H), 7.55 (d, 1H), 7.70 (d, 1H), 7.85 (d, 1H), 7.94 (s, 1H), 8.09 (s, 1H), 8.30 (t, 2H), 8.38 (s, 1H)

Synthesis Example 3

Preparation of 13,13-dimethyl-13H-indeno[1,2-b]anthracene

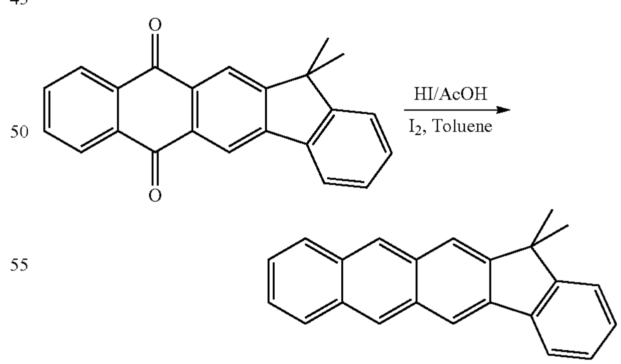

2,9-dibromo-13,13-dimethyl-6H-indeno[1,2-b]anthracene-6,11(13H)-dione (19 g, 0.058 mol) was dissolved in acetic acid (200 ml), and added with 57% HI (50 ml), followed by reflux-stirring for 48 hours. After the reaction was completed, the resultant solution was added with distilled water (500 ml). The produced solid was filtered and dissolved in toluene (200 ml) and iodine (4.56 g, 0.018 mol) was added thereto, followed by reflux-stirring for 3 hours. After the reaction was completed, through extraction and column chromatography, 13,13-dimethyl-13H-indeno[1,2-b]anthracene (10 g, yield 54%) was obtained.

$^1$H NMR: 1.60 (s, 6H), 7.35 (t, 2H), 7.40 (m, 2H), 7.51 (d, 1H), 7.95 (m, 3H), 7.99 (s, 1H), 8.35 (s, 1H), 8.44 (s, 1H), 8.50 (s, 1H); FD-MS: m/z 294 ($M^+$).

Synthesis Example 4

Preparation of 6,11-dibromo-13,13-dimethyl-13H-indeno[1,2-b]anthracene

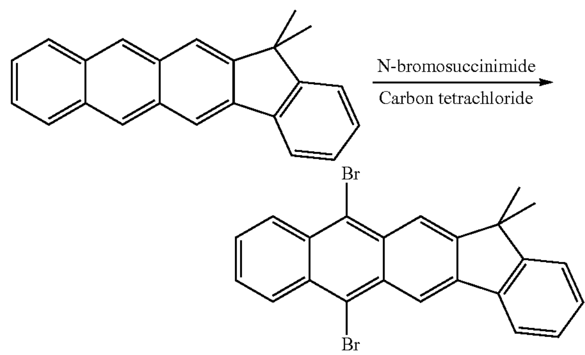

13,13-dimethyl-13H-indeno[1,2-b]anthracene (10 g, 0.034 mol) and N-bromosuccinimide (12.1 g, 0.068 mol) were dissolved in carbon tetrachloride (200 ml), and stirred at 60° C., for 8 hours. After the reaction was completed, the resultant product was extracted with distilled water, and through column chromatography, 6,11-dibromo-13,13-dimethyl-13H-indeno[1,2-b]anthracene (10.9 g, yield 71%) was obtained.

$^1$H NMR: 1.63 (s, 6H), 7.42 (t, 2H), 7.57 (dd, 1H), 7.66 (dd, 2H), 8.08 (dd, 1H), 8.60 (dd, 2H), 8.65 (s, 1H), 8.93 (s, 1H); FD-MS: m/z 452 ($M^+$).

Example 1

Preparation of Inv-1-1

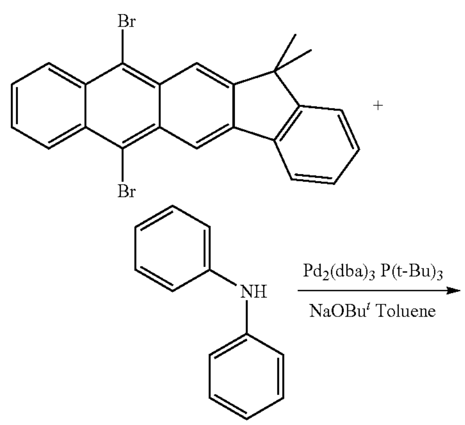

-continued

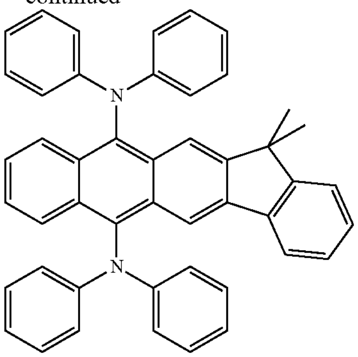

6,11-dibromo-13,13-dimethyl-13H-indeno[1,2-b]anthracene (7.2 g, 16.0 mmol), and diphenylamine (8.1 g, 48.0 mmol) were dissolved in toluene 350 mL, and tris benzylidene acetone dipalladium (0.44 g, 0.48 mmol) was added thereto under a nitrogen atmosphere. Then, P(t-Bu)$_3$ (0.65 g, 3.20 mmol) was added to the resultant mixture, and NaOBu$^t$ (6.15 g, 64.0 mmol) was added thereto. The resultant solution was reflux-stirred for 24 hours. After the reaction was completed, the resultant solution was subjected to high temperature filtration through a thin silica pad so as to remove palladium. The filtrate was worked-up by EA and water, and the EA layer was dried by $MgSO_4$. The organic solvent layer was evaporated under a reduced pressure to remove almost all the solvent. Then, through filtration, a brown solid product was firstly obtained. The filtrate was dissolved in a small amount of methylene chloride, and re-crystallized by lowering the temperature. Then, the resultant product was filtered, a lime green solid (9.2 g, yield 92%) was obtained.

$^1$H NMR: 1.62 (s, 6H), 6.45 (m, 8H), 7.05 (m, 12H), 7.42 (dd, 2H), 7.61 (t, 1H), 7.86 (dd, 2H), 7.93 (t, 1H), 8.07 (s, 1H), 8.21 (t, 2H), 8.37 (s, 1H); FD-MS: m/z 628 ($M^+$).

Example 2

Preparation of Inv-1-2

6,11-dibromo-13,13-dimethyl-13H-indeno[1,2-b]anthracene (5.0 g, 11.1 mmol), and dip-tolylamine (6.6 g, 33.3 mmol) were dissolved in toluene 250 mL. Inv-1-2 (6.91 g, yield 91%) was obtained through the same synthesis method as described in Example 1. FD-MS: m/z 684 ($M^+$).

Example 3

Preparation of Inv-1-3

6,11-dibromo-13,13-dimethyl-13H-indeno[1,2-b]anthracene (5.0 g, 11.1 mmol), and 4-tert-butyl-N-(4-isopropylphenyl)aniline (8.9 g, 33.3 mmol) were dissolved in toluene 250 mL. Inv-1-3 (8.24 g, yield 90%) was obtained through the same synthesis method as described in Example 1. FD-MS: m/z 824 ($M^+$).

Example 4

Preparation of Inv-1-4

6,11-dibromo-13,13-dimethyl-13H-indeno[1,2-b]anthracene (5.0 g, 11.1 mmol), and 4-isopropyl-N-p-tolylaniline (7.5 g, 33.3 mmol) were dissolved in toluene 250 mL.

Inv-1-4 (7.65 g, yield 93%) was obtained through the same synthesis method as described in Example 1. FD-MS: m/z 740 ($M^+$).

Example 5

Preparation of Inv-1-5

6,11-dibromo-13,13-dimethyl-13H-indeno[1,2-b]anthracene (5.0 g, 11.1 mmol), and bis(3,5-dimethylphenyl)amine (7.5 g, 33.3 mmol) were dissolved in toluene 250 mL. Inv-1-5 (7.40 g, yield 90%) was obtained through the same synthesis method as described in Example 1. FD-MS: m/z 740 ($M^+$).

Example 6

Preparation of Inv-1-6

6,11-dibromo-13,13-dimethyl-13H-indeno[1,2-b]anthracene (5.0 g, 11.1 mmol), and N-phenylnaphthalen-2-amine (7.3 g, 33.3 mmol) were dissolved in toluene 250 mL. Inv-1-6 (7.44 g, yield 92%) was obtained through the same synthesis method as described in Example 1. FD-MS: m/z 728 ($M^+$).

Example 7

Preparation of Inv-1-9

6,11-dibromo-13,13-dimethyl-13H-indeno[1,2-b]anthracene (5.0 g, 11.1 mmol), and N-(naphthalen-2-yl)naphthalen-1-amine (8.96 g, 33.3 mmol) were dissolved in toluene 250 mL. Inv-1-9 (8.19 g, yield 89%) was obtained through the same synthesis method as described in Example 1. FD-MS: m/z 828 ($M^+$).

Example 8

Preparation of Inv-1-11

6,11-dibromo-13,13-dimethyl-13H-indeno[1,2-b]anthracene (5.0 g, 11.1 mmol), and dibiphenyl-4-ylamine (10.69 g, 33.3 mmol) were dissolved in toluene 250 mL. Inv-1-11 (8.80 g, yield 85%) was obtained through the same synthesis method as described in Example 1. FD-MS: m/z 932 ($M^+$).

Example 9

Preparation of Inv-1-13

6,11-dibromo-13,13-dimethyl-13H-indeno[1,2-b]anthracene (5.0 g, 11.1 mmol), and N-(biphenyl-4-yl)naphthalen-2-amine (9.83 g, 33.3 mmol) were dissolved in toluene 250 mL. Inv-1-13 (8.41 g, yield 86%) was obtained through the same synthesis method as described in Example 1. FD-MS: m/z 880 ($M^+$).

Example 10

Preparation of Inv-1-15

6,11-dibromo-13,13-dimethyl-13H-indeno[1,2-b]anthracene (5.0 g, 11.1 mmol), and 9,9-dimethyl-N-phenyl-9H-fluoren-2-amine (9.50 g, 33.3 mmol) were dissolved in toluene 250 mL. Inv-1-15 (8.60 g, yield 90%) was obtained through the same synthesis method as described in Example 1. FD-MS: m/z 860 ($M^+$).

Example 11

Preparation of Inv-1-17

6,11-dibromo-13,13-dimethyl-13H-indeno[1,2-b]anthracene (5.0 g, 11.1 mmol), and bis(9,9-dimethyl-9H-fluoren-2-yl)amine (13.36 g, 33.3 mmol) were dissolved in toluene 250 mL. Inv-1-17 (11.17 g, yield 92%) was obtained through the same synthesis method as described in Example 1. FD-MS: m/z 1092 ($M^+$).

Example 12

Preparation of Inv-1-18

6,11-dibromo-13,13-dimethyl-13H-indeno[1,2-b]anthracene (5.0 g, 11.1 mmol), and N-phenylanthracene-2-amine (8.96 g, 33.3 mmol) were dissolved in toluene 250 mL. Inv-1-18 (7.73 g, yield 84%) was obtained through the same synthesis method as described in Example 1. FD-MS: m/z 828 ($M^+$).

Example 13

Preparation of Inv-1-22

6,11-dibromo-13,13-dimethyl-13H-indeno[1,2-b]anthracene (5.0 g, 11.1 mmol), and N-phenyl-9,9'-spirobi[fluoren]-2-amine (21.49 g, 33.3 mmol) were dissolved in toluene 250 mL. Inv-1-22 (9.82 g, yield 80%) was obtained through the same synthesis method as described in Example 1. FD-MS: m/z 1104 ($M^+$).

Example 14

Preparation of Inv-1-26

6,11-dibromo-13,13-dimethyl-13H-indeno[1,2-b]anthracene (5.0 g, 11.1 mmol), and N-phenylbiphenyl-2-amine (8.16 g, 33.3 mmol) were dissolved in toluene 250 mL. Inv-1-26 (7.89 g, yield 91%) was obtained through the same synthesis method as described in Example 1. FD-MS: m/z 780 ($M^+$).

Example 15

Preparation of Inv-1-31

6,11-dibromo-13,13-dimethyl-13H-indeno[1,2-b]anthracene (5.0 g, 11.1 mmol), and N-(biphenyl-4-yl)biphenyl-3-amine (10.69 g, 33.3 mmol) were dissolved in toluene 250 mL. Inv-1-31 (8.29 g, yield 80%) was obtained through the same synthesis method as described in Example 1. FD-MS: m/z 932 ($M^+$).

Example 16

Preparation of Inv-1-35

6,11-dibromo-13,13-dimethyl-13H-indeno[1,2-b]anthracene (5.0 g, 11.1 mmol), and N-(4-isopropylphenyl)biphenyl-4-amine (9.56 g, 33.3 mmol) were dissolved in toluene 250 mL. Inv-1-35 (8.16 g, yield 85%) was obtained through the same synthesis method as described in Example 1. FD-MS: m/z 864 ($M^+$).

Example 17

Preparation of Inv-1-39

6,11-dibromo-13,13-dimethyl-13H-indeno[1,2-b]anthracene (5.0 g, 11.1 mmol), and N-(biphenyl-2-yl)naphthalen-1-amine (9.83 g, 33.3 mmol) were dissolved in toluene 250 mL. Inv-1-39 (8.71 g, yield 89%) was obtained through the same synthesis method as described in Example 1. FD-MS: m/z 880 ($M^+$).

Example 18

Preparation of Inv-1-40

6,11-dibromo-13,13-dimethyl-13H-indeno[1,2-b]anthracene (5.0 g, 11.1 mmol), and N-methylaniline (3.57 g, 33.3 mmol) were dissolved in toluene 250 mL. Inv-1-40 (5.33 g, yield 95%) was obtained through the same synthesis method as described in Example 1. FD-MS: m/z 504 ($M^+$).

Example 19

Preparation of Inv-1-42

6,11-dibromo-13,13-dimethyl-13H-indeno[1,2-b]anthracene (5.0 g, 11.1 mmol), and N-(biphenyl-4-yl)thiophen-2-amine (8.36 g, 33.3 mmol) were dissolved in toluene 250 mL. Inv-1-42 (7.92 g, yield 90%) was obtained through the same synthesis method as described in Example 1. FD-MS: m/z 792 ($M^+$).

Example 20

Preparation of Inv-1-47

6,11-dibromo-13,13-dimethyl-13H-indeno[1,2-b]anthracene (5.0 g, 11.1 mmol), and N-phenylpyrazin-2-amine (5.70 g, 33.3 mmol) were dissolved in toluene 250 mL. Inv-1-47 (6.18 g, yield 88%) was obtained through the same synthesis method as described in Example 1. FD-MS: m/z 632 ($M^+$).

Example 21

Preparation of Inv-1-48

6,11-dibromo-13,13-dimethyl-13H-indeno[1,2-b]anthracene (5.0 g, 11.1 mmol), and N-(biphenyl-4-yl)pyrazin-2-amine (8.23 g, 33.3 mmol) were dissolved in toluene 250 mL. Inv-1-48 (7.58 g, yield 87%) was obtained through the same synthesis method as described in Example 1. FD-MS: m/z 784 ($M^+$).

Example 22

Preparation of Inv-1-52

6,11-dibromo-13,13-dimethyl-13H-indeno[1,2-b]anthracene (5.0 g, 11.1 mmol), and N-(4-isopropylphenyl) pyrazin-2-amine (7.10 g, 33.3 mmol) were dissolved in toluene 250 mL. Inv-1-52 (7.32 g, yield 92%) was obtained through the same synthesis method as described in Example 1. FD-MS: m/z 716 ($M^+$).

Example 23

Preparation of Inv-1-53

6,11-dibromo-13,13-dimethyl-13H-indeno[1,2-b]anthracene (5.0 g, 11.1 mmol), and N-phenylpyridin-2-amine (5.66 g, 33.3 mmol) were dissolved in toluene 250 mL. Inv-1-53 (6.58 g, yield 94%) was obtained through the same synthesis method as described in Example 1. FD-MS: m/z 630 ($M^+$).

Example 24

Preparation of Inv-1-54

6,11-dibromo-13,13-dimethyl-13H-indeno[1,2-b]anthracene (5.0 g, 11.1 mmol), and N-(biphenyl-4-yl)pyridin-2-amine (8.20 g, 33.3 mmol) were dissolved in toluene 250 mL. Inv-1-54 (7.74 g, yield 89%) was obtained through the same synthesis method as described in Example 1. FD-MS: m/z 782 ($M^+$).

Example 25

Preparation of Inv-1-59

6,11-dibromo-13,13-dimethyl-13H-indeno[1,2-b]anthracene (5.0 g, 11.1 mmol), and N-(naphthalen-2-yl)pyridin-2-amine (7.33 g, 33.3 mmol) were dissolved in toluene 250 mL. Inv-1-59 (7.38 g, yield 91%) was obtained through the same synthesis method as described in Example 1. FD-MS: m/z 730 ($M^+$).

Example 26

Preparation of Inv-1-61

6,11-dibromo-13,13-dimethyl-13H-indeno[1,2-b]anthracene (5.0 g, 11.1 mmol), and N-(9,9-dimethyl-9H-fluoren-2-yl)pyridin-2-amine (9.53 g, 33.3 mmol) were dissolved in toluene 250 mL. Inv-1-61 (8.62 g, yield 90%) was obtained through the same synthesis method as described in Example 1. FD-MS: m/z 862 ($M^+$).

Example 27

Preparation of Inv-1-64

6,11-dibromo-13,13-dimethyl-13H-indeno[1,2-b]anthracene (5.0 g, 11.1 mmol), and N-(naphthalen-2-yl)quinolin-6-amine (8.99 g, 33.3 mmol) were dissolved in toluene 250 mL. Inv-1-64 (8.03 g, yield 87%) was obtained through the same synthesis method as described in Example 1. FD-MS: m/z 830 ($M^+$).

Example 28

Preparation of Inv-1-66

6,11-dibromo-13,13-dimethyl-13H-indeno[1,2-b]anthracene (5.0 g, 11.1 mmol), and N-(biphenyl-4-yl)quinolin-6-amine (9.86 g, 33.3 mmol) were dissolved in toluene 250 mL. Inv-1-66 (8.14 g, yield 83%) was obtained through the same synthesis method as described in Example 1. FD-MS: m/z 882 ($M^+$).

Example 29

Preparation of Inv-1-69

6,11-dibromo-13,13-dimethyl-13H-indeno[1,2-b]anthracene (5.0 g, 11.1 mmol), and N-phenylisoquinolin-4-amine (7.33 g, 33.3 mmol) were dissolved in toluene 250 mL. Inv-1-69 (6.98 g, yield 86%) was obtained through the same synthesis method as described in Example 1. FD-MS: m/z 730 ($M^+$).

Example 30

Preparation of Inv-1-72

6,11-dibromo-13,13-dimethyl-13H-indeno[1,2-b]anthracene (5.0 g, 11.1 mmol), and N-phenylisoquinolin-1-amine (7.33 g, 33.3 mmol) were dissolved in toluene 250 mL. Inv-1-72 (6.82 g, yield 84%) was obtained through the same synthesis method as described in Example 1. FD-MS: m/z 730 ($M^+$).

Example 31

Preparation of Inv-1-73

6,11-dibromo-13,13-dimethyl-13H-indeno[1,2-b]anthracene (5.0 g, 11.1 mmol), and N-phenylquinolin-3-amine (7.33 g, 33.3 mmol) were dissolved in toluene 250 mL. Inv-1-73 (6.65 g, yield 82%) was obtained through the same synthesis method as described in Example 1. FD-MS: m/z 730 ($M^+$).

Example 32

Preparation of Inv-1-74

6,11-dibromo-13,13-dimethyl-13H-indeno[1,2-b]anthracene (5.0 g, 11.1 mmol), and N-phenylisoquinolin-3-amine (7.33 g, 33.3 mmol) were dissolved in toluene 250 mL. Inv-1-74 (6.49 g, yield 80%) was obtained through the same synthesis method as described in Example 1. FD-MS: m/z 730 ($M^+$).

Example 33

Preparation of Inv-1-76

6,11-dibromo-13,13-dimethyl-13H-indeno[1,2-b]anthracene (5.0 g, 11.1 mmol), and 4-isopropyl-N-(4-methoxyphenyl)aniline (8.03 g, 33.3 mmol) were dissolved in toluene 250 mL. Inv-1-76 (6.44 g, yield 75%) was obtained through the same synthesis method as described in Example 1. FD-MS: m/z 772 ($M^+$).

Example 34

Preparation of Inv-1-78

6,11-dibromo-13,13-dimethyl-13H-indeno[1,2-b]anthracene (5.0 g, 11.1 mmol), and N-(4-isopropylphenyl)-2-methoxyaniline (8.03 g, 33.3 mmol) were dissolved in toluene 250 mL. Inv-1-78 (6.26 g, yield 73%) was obtained through the same synthesis method as described in Example 1. FD-MS: m/z 772 ($M^+$).

Example 35

Preparation of Inv-1-79

6,11-dibromo-13,13-dimethyl-13H-indeno[1,2-b]anthracene (5.0 g, 11.1 mmol), and dibenzylamine (6.56 g, 33.3 mmol) were dissolved in toluene 250 mL. Inv-1-79 (6.23 g, yield 82%) was obtained through the same synthesis method as described in Example 1. FD-MS: m/z 684 ($M^+$).

Synthesis Example 5

Preparation of 5-bromo-2-(9,9-dimethyl-9H-fluorene-2-carbonyl)benzoic acid

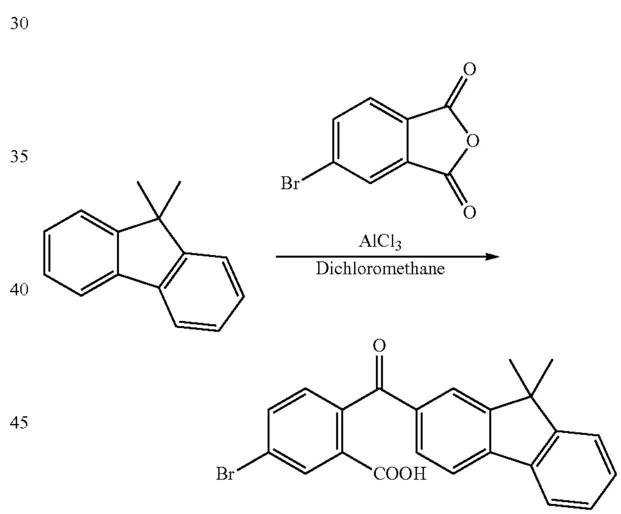

9,9-dimethyl-9H-fluorene (27.78 g, 0.143 mol) and 4-Bromo Phthalic anhydride (48.69 g, 0.214 mol) were placed in a reaction vessel, and added with Dichloromethane (700 ml). At 0° C., aluminum chloride (28.7 g, 0.214 mol) was gradually added thereto, and the temperature was raised up to room temperature. Then, the resultant mixture was stirred for 12 hours. After the reaction was completed, the resultant product was gradually added with distilled water. The resultant product was extracted with an excess of dichloromethane, and washed several times with distilled water. After solvent removal, the produced solid was placed in a Hexane 2 l-containing vessel, washed, filtered, and dried, 5-bromo-2-(9,9-dimethyl-9H-fluorene-2-carbonyl)benzoic acid (30 g, yield 50%) was obtained.

$^1$H NMR: 1.63 (s, 6H), 7.30 (t, 2H), 7.55 (d, 1H), 7.84 (d, 1H), 7.92 (m, 3H), 7.99 (s, 1H), 8.08 (s, 1H), 8.12 (d, 1H), 12.31 (s, 1H)

Synthesis Example 6

Preparation of 8-bromo-13,13-dimethyl-6H-indeno[1,2-b]anthracene-6,11(13H)-dione

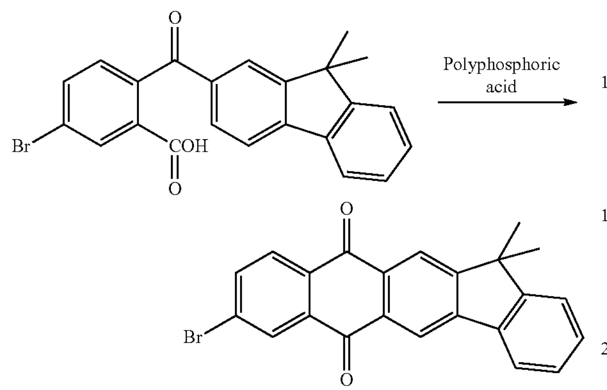

5-bromo-2-(9,9-dimethyl-9H-fluorene-2-carbonyl)benzoic acid (18.53 g, 0.044 mol) was placed in a flask, and polyphosphoric acid (50 ml) was added thereto. The reaction mixture was heated at 140° C. for 2 hours and then and cooled to less than 50° C., and distilled water was gradually added thereto. The produced solid was filtered, washed with a small amount of methanol, and dried, 8-bromo-13,13-dimethyl-6H-indeno[1,2-b]anthracene-6,11(13H)-dione (11 g, yield 62%) was obtained.

$^1$H NMR: 1.68 (s, 6H), 7.08 (t, 1H), 7.28 (t, 1H), 7.55 (d, 1H), 7.70 (m, 2H), 7.84 (d, 1H), 7.97 (s, 1H), 8.09 (s, 1H), 8.21 (s, 1H).

Synthesis Example 7

Preparation of 8-bromo-13,13-dimethyl-13H-indeno[1,2-b]anthracene

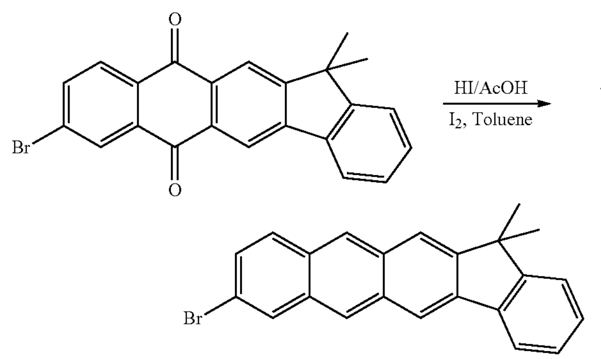

8-bromo-13,13-dimethyl-6H-indeno[1,2-b]anthracene-6,11(13H)-dione (20 g, 0.05 mol) was dissolved in acetic acid (200 ml) and added with 57% HI (50 ml), followed by reflux-stirring for 48 hours. After the reaction was completed, the resultant solution was added with distilled water 500 ml. The produced solid was filtered and dissolved in toluene 200 ml and iodine (4.05 g, 0.016 mol) was added thereto, followed by reflux-stirring for 3 hours. After the reaction was completed, through extraction and column chromatography, 8-bromo-13,13-dimethyl-13H-indeno[1,2-b]anthracene (11.1 g, yield 60%) was obtained.

$^1$H NMR: 1.60 (s, 6H), 7.36 (t, 2H), 7.50 (m, 2H), 7.95 (m, 2H), 8.06 (s, 1H), 8.22 (s, 1H), 8.35 (s, 1H), 8.40 (s, 1H), 8.51 (s, 1H); FD-MS: m/z 374 ($M^+$).

Synthesis Example 8

Preparation of 6,8,11-tribromo-13,13-dimethyl-13H-indeno[1,2-b]anthracene

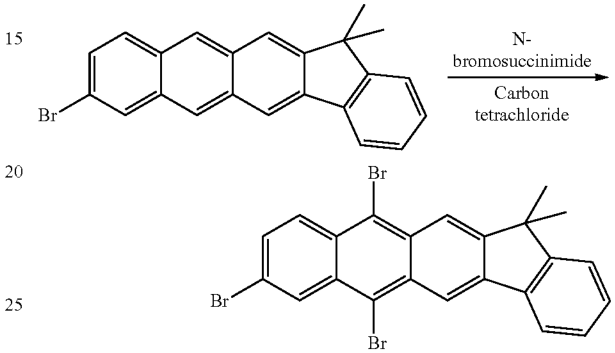

8-bromo-13,13-dimethyl-13H-indeno[1,2-b]anthracene (11 g, 0.03 mol) and N-bromosuccinimide (11.39 g, 0.064 mol) were dissolved in carbon tetrachloride (200 ml), and stirred at 60° C., for 8 hours. After the reaction was completed, the resultant product was extracted with distilled water, and through column chromatography, 6,8,11-tribromo-13,13-dimethyl-13H-indeno[1,2-b]anthracene (11.7 g, yield 75%) was obtained.

$^1$H NMR: 1.56 (s, 6H), 7.44 (t, 2H), 7.58 (d, 1H), 7.74 (t, 1H), 8.09 (d, 1H), 8.51 (dd, 1H), 8.62 (s, 1H), 8.78 (s, 1H), 8.90 (s, 1H); FD-MS: m/z 532 ($M^+$).

Example 36

Preparation of Inv-2-1

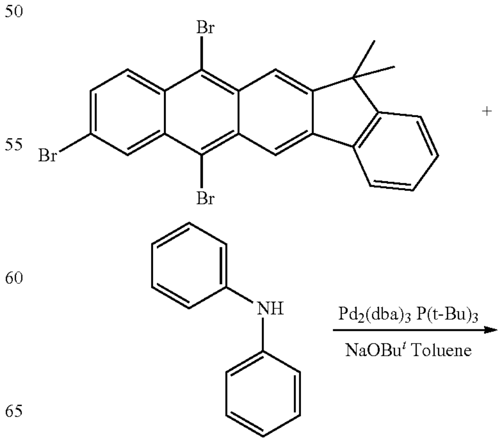

-continued

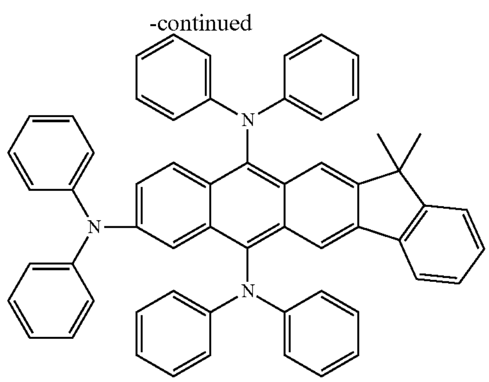

6,8,11-tribromo-13,13-dimethyl-13H-indeno[1,2-b]anthracene (5.0 g, 9.47 mmol), and diphenylamine (4.81 g, 28.4 mmol) were dissolved in toluene (300 mL), and tris benzylidene acetone dipalladium (0.26 g, 0.28 mmol) was added thereto under a nitrogen atmosphere. Then, $P(t\text{-}Bu)_3$ (0.38 g, 1.89 mmol) was added to the resultant mixture, and $NaOBu^t$ (3.64 g, 37.89 mmol) was added thereto. The resultant solution was reflux-stirred for hours. After the reaction was completed, the resultant solution was subjected to high temperature filtration through a thin silica pad so as to remove palladium. The filtrate was worked-up by EA and water, and the EA layer was dried by $MgSO_4$. The organic solvent layer was evaporated under a reduced pressure to remove almost all the solvent. Then, through filtration, a brown solid product was firstly obtained. The filtrate was dissolved in a small amount of methylene chloride, and re-crystallized by lowering the temperature. Then, the resultant product was filtered to gain a yellow solid (6.78 g, yield 90%).

$^1$H NMR: 1.64 (s, 6H), 6.47 (m, 12H), 7.09 (m, 18H), 7.40 (t, 1H), 7.52 (s, 1H), 7.63 (t, 1H), 7.78 (dd, 2H), 7.91 (t, 1H), 8.12 (s, 1H), 8.28 (t, 2H), 8.43 (s, 1H); FD-MS: m/z 796 ($M^+$).

Example 37

Preparation of Inv-2-3

6,8,11-tribromo-13,13-dimethyl-13H-indeno[1,2-b]anthracene (5.0 g, 9.47 mmol), and 4-tert-butyl-N-(4-isopropylphenyl)aniline (7.59 g, 28.4 mmol) were dissolved in toluene 250 mL. Inv-2-3 (8.98 g, yield 87%) was obtained through the same synthesis method as described in Example 36. FD-MS: m/z 1090 ($M^+$).

Example 38

Preparation of Inv-2-5

6,8,11-tribromo-13,13-dimethyl-13H-indeno[1,2-b]anthracene (5.0 g, 9.47 mmol), and bis(3,5-dimethylphenyl) amine (6.39 g, 28.4 mmol) were dissolved in toluene 250 mL. Inv-2-5 (8.21 g, yield 90%) was obtained through the same synthesis method as described in Example 36. FD-MS: m/z 963 ($M^+$).

Example 39

Preparation of Inv-2-7

6,8,11-tribromo-13,13-dimethyl-13H-indeno[1,2-b]anthracene (5.0 g, 9.47 mmol), and N-phenylnaphthalen-1-amine (6.22 g, 28.4 mmol) were dissolved in toluene 250 mL. Inv-2-7 (7.88 g, yield 88%) was obtained through the same synthesis method as described in Example 36. FD-MS: m/z 945 ($M^+$).

Example 40

Preparation of Inv-2-10

6,8,11-tribromo-13,13-dimethyl-13H-indeno[1,2-b]anthracene (5.0 g, 9.47 mmol), and dinaphthalen-2-ylamine (7.64 g, 28.4 mmol) were dissolved in toluene 250 mL. Inv-2-10 (8.71 g, yield 84%) was obtained through the same synthesis method as described in Example 36. FD-MS: m/z 1095 ($M^+$).

Example 41

Preparation of Inv-2-11

6,8,11-tribromo-13,13-dimethyl-13H-indeno[1,2-b]anthracene (5.0 g, 9.47 mmol), and dibiphenyl-4-ylamine (9.12 g, 28.4 mmol) were dissolved in toluene 250 mL. Inv-2-11 (9.24 g, yield 78%) was obtained through the same synthesis method as described in Example 36. FD-MS: m/z 1252 ($M^+$).

Example 42

Preparation of Inv-2-14

6,8,11-tribromo-13,13-dimethyl-13H-indeno[1,2-b]anthracene (5.0 g, 9.47 mmol), and N-(biphenyl-4-yl)naphthalen-1-amine (8.38 g, 28.4 mmol) were dissolved in toluene 250 mL. Inv-2-14 (8.78 g, yield 79%) was obtained through the same synthesis method as described in Example 36. FD-MS: m/z 1174 ($M^+$).

Example 43

Preparation of Inv-2-16

6,8,11-tribromo-13,13-dimethyl-13H-indeno[1,2-b]anthracene (5.0 g, 9.47 mmol), and N-(biphenyl-4-yl)-9,9-dimethyl-9H-fluoren-2-amine (10.26 g, 28.4 mmol) were dissolved in toluene 250 mL. Inv-2-16 (10.01 g, yield 77%) was obtained through the same synthesis method as described in Example 36. FD-MS: m/z 1373 ($M^+$).

Example 44

Preparation of Inv-2-17

6,8,11-tribromo-13,13-dimethyl-13H-indeno[1,2-b]anthracene (5.0 g, 9.47 mmol), and bis(9,9-dimethyl-9H-fluoren-2-yl)amine (11.39 g, 28.4 mmol) were dissolved in toluene 250 mL. Inv-2-17 (10.60 g, yield 75%) was obtained through the same synthesis method as described in Example 36. FD-MS: m/z 1492 ($M^+$).

Example 45

Preparation of Inv-2-21

6,8,11-tribromo-13,13-dimethyl-13H-indeno[1,2-b]anthracene (5.0 g, 9.47 mmol), and N-(biphenyl-4-yl)anthracene-2-amine (9.80 g, 28.4 mmol) were dissolved in toluene 250 mL. Inv-2-21 (9.02 g, yield 72%) was obtained through the same synthesis method as described in Example 36. FD-MS: m/z 1324 ($M^+$).

Example 46

Preparation of Inv-2-23

6,8,11-tribromo-13,13-dimethyl-13H-indeno[1,2-b]anthracene (5.0 g, 9.47 mmol), and N-(biphenyl-4-yl)-9,9'-spirobi[fluoren]-2-amine (13.72 g, 28.4 mmol) were dissolved in toluene 250 mL. Inv-2-23 (10.7 g, yield 65%) was obtained through the same synthesis method as described in Example 36. FD-MS: m/z 1738 ($M^+$).

Example 47

Preparation of Inv-2-25

6,8,11-tribromo-13,13-dimethyl-13H-indeno[1,2-b]anthracene (5.0 g, 9.47 mmol), and dibiphenyl-2-ylamine (9.12 g, 28.4 mmol) were dissolved in toluene 250 mL. Inv-2-25 (8.53 g, yield 72%) was obtained through the same synthesis method as described in Example 36. FD-MS: m/z 1252 ($M^+$).

Example 48

Preparation of Inv-2-28

6,8,11-tribromo-13,13-dimethyl-13H-indeno[1,2-b]anthracene (5.0 g, 9.47 mmol), and N-(4-isopropylphenyl)biphenyl-2-amine (8.16 g, 28.4 mmol) were dissolved in toluene 250 mL. Inv-2-28 (8.17 g, yield 75%) was obtained through the same synthesis method as described in Example 36. FD-MS: m/z 1150 ($M^+$).

Example 49

Preparation of Inv-2-35

6,8,11-tribromo-13,13-dimethyl-13H-indeno[1,2-b]anthracene (5.0 g, 9.47 mmol), and N-(4-isopropylphenyl)biphenyl-4-amine (8.16 g, 28.4 mmol) were dissolved in toluene 250 mL. Inv-2-35 (7.95 g, yield 73%) was obtained through the same synthesis method as described in Example 36. FD-MS: m/z 1150 ($M^+$).

Example 50

Preparation of Inv-2-41

6,8,11-tribromo-13,13-dimethyl-13H-indeno[1,2-b]anthracene (5.0 g, 9.47 mmol), and N-phenylthiophen-2-amine (4.97 g, 28.4 mmol) were dissolved in toluene 250 mL. Inv-2-41 (6.08 g, yield 79%) was obtained through the same synthesis method as described in Example 36. FD-MS: m/z 813 ($M^+$).

Example 51

Preparation of Inv-2-42

6,8,11-tribromo-13,13-dimethyl-13H-indeno[1,2-b]anthracene (5.0 g, 9.47 mmol), and N-(biphenyl-4-yl)thiophen-2-amine (7.13 g, 28.4 mmol) were dissolved in toluene 250 mL. Inv-2-42 (7.10 g, yield 72%) was obtained through the same synthesis method as described in Example 36. FD-MS: m/z 1041 ($M^+$).

Example 52

Preparation of Inv-2-47

6,8,11-tribromo-13,13-dimethyl-13H-indeno[1,2-b]anthracene (5.0 g, 9.47 mmol), and N-phenylpyrazin-2-amine (4.86 g, 28.4 mmol) were dissolved in toluene 250 mL. Inv-2-47 (6.07 g, yield 80%) was obtained through the same synthesis method as described in Example 36. FD-MS: m/z 801 ($M^+$).

Example 53

Preparation of Inv-2-49

6,8,11-tribromo-13,13-dimethyl-13H-indeno[1,2-b]anthracene (5.0 g, 9.47 mmol), and N-(biphenyl-3-yl)pyrazin-2-amine (7.02 g, 28.4 mmol) were dissolved in toluene 250 mL. Inv-2-49 (7.41 g, yield 76%) was obtained through the same synthesis method as described in Example 36. FD-MS: m/z 1029 ($M^+$).

Example 54

Preparation of Inv-2-53

6,8,11-tribromo-13,13-dimethyl-13H-indeno[1,2-b]anthracene (5.0 g, 9.47 mmol), and N-phenylpyridin-2-amine (4.83 g, 28.4 mmol) were dissolved in toluene 250 mL. Inv-2-53 (6.05 g, yield 80%) was obtained through the same synthesis method as described in Example 36. FD-MS: m/z 798 ($M^+$).

Example 55

Preparation of Inv-2-58

6,8,11-tribromo-13,13-dimethyl-13H-indeno[1,2-b]anthracene (5.0 g, 9.47 mmol), and N-(4-isopropylphenyl)pyridin-2-amine (6.02 g, 28.4 mmol) were dissolved in toluene 250 mL. Inv-2-58 (7.18 g, yield 82%) was obtained through the same synthesis method as described in Example 36. FD-MS: m/z 924 ($M^+$).

Example 56

Preparation of Inv-2-60

6,8,11-tribromo-13,13-dimethyl-13H-indeno[1,2-b]anthracene (5.0 g, 9.47 mmol), and N-(naphthalen-1-yl)pyridin-2-amine (6.25 g, 28.4 mmol) were dissolved in toluene 250 mL. Inv-2-60 (7.10 g, yield 79%) was obtained through the same synthesis method as described in Example 36. FD-MS: m/z 948 ($M^+$).

Example 57

Preparation of Inv-2-61

6,8,11-tribromo-13,13-dimethyl-13H-indeno[1,2-b]anthracene (5.0 g, 9.47 mmol), and N-(9,9-dimethyl-9H-fluoren-2-yl)pyridin-2-amine (8.13 g, 28.4 mmol) were dissolved in toluene 250 mL. Inv-2-60 (8.69 g, yield 80%) was obtained through the same synthesis method as described in Example 36. FD-MS: m/z 1147 ($M^+$).

Example 58

Preparation of Inv-2-66

6,8,11-tribromo-13,13-dimethyl-13H-indeno[1,2-b]anthracene (5.0 g, 9.47 mmol), and N-(biphenyl-4-yl)quinolin-6-amine (8.41 g, 28.4 mmol) were dissolved in toluene 250 mL. Inv-2-66 (8.36 g, yield 75%) was obtained through the same synthesis method as described in Example 36. FD-MS: m/z 1176 ($M^+$).

Example 59

Preparation of Inv-2-71

6,8,11-tribromo-13,13-dimethyl-13H-indeno[1,2-b]anthracene (5.0 g, 9.47 mmol), and N-phenylquinolin-8-amine (6.25 g, 28.4 mmol) were dissolved in toluene 250 mL. Inv-2-71 (7.27 g, yield 81%) was obtained through the same synthesis method as described in Example 36. FD-MS: m/z 948 ($M^+$).

Example 60

Preparation of Inv-2-74

6,8,11-tribromo-13,13-dimethyl-13H-indeno[1,2-b]anthracene (5.0 g, 9.47 mmol), and N-phenylisoquinolin-3-amine (6.25 g, 28.4 mmol) were dissolved in toluene 250 mL. Inv-2-74 (7.36 g, yield 82%) was obtained through the same synthesis method as described in Example 36. FD-MS: m/z 948 ($M^+$).

Example 61

Preparation of Inv-2-76

6,8,11-tribromo-13,13-dimethyl-13H-indeno[1,2-b]anthracene (5.0 g, 9.47 mmol), and 4-isopropyl-N-(4-methoxyphenyl)benzenamine (6.85 g, 28.4 mmol) were dissolved in toluene 250 mL. Inv-2-76 (8.05 g, yield 84%) was obtained through the same synthesis method as described in Example 36. FD-MS: m/z 1012 ($M^+$).

Example 62

Preparation of Inv-2-78

6,8,11-tribromo-13,13-dimethyl-13H-indeno[1,2-b]anthracene (5.0 g, 9.47 mmol), and N-(4-isopropylphenyl)-2-methoxybenzenamine (6.85 g, 28.4 mmol) were dissolved in toluene 250 mL. Inv-2-78 (7.85 g, yield 82%) was obtained through the same synthesis method as described in Example 36. FD-MS: m/z 1012 ($M^+$).

Example 63

Preparation of Inv-2-79

6,8,11-tribromo-13,13-dimethyl-13H-indeno[1,2-b]anthracene (5.0 g, 9.47 mmol), and dibenzylamine (5.60 g, 28.4 mmol) were dissolved in toluene 250 mL. Inv-2-79 (7.08 g, yield 85%) was obtained through the same synthesis method as described in Example 36. FD-MS: m/z 879 ($M^+$).

Synthesis Example 9

Preparation of 2-(7-bromo-9,9-dimethyl-9H-fluorene-2-carbonyl)benzoic acid

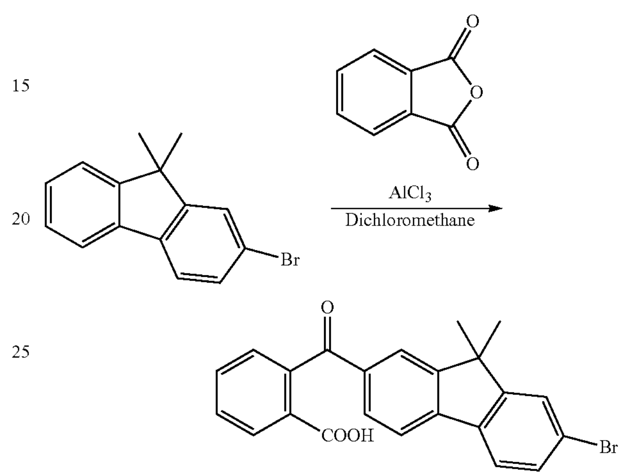

2-bromo-9,9-dimethyl-9H-fluorene (25.0 g, 0.092 mol) and phthalic anhydride (17.68 g, 0.119 mol) were placed in a reaction vessel, and added with dichloromethane (700 ml). At 0° C., aluminum chloride (18.5 g, 0.138 mol) was gradually added thereto, and the temperature was raised up to room temperature. Then, the resultant mixture was stirred for 12 hours. After the reaction was completed, the resultant product was gradually added with distilled water. The resultant product was extracted with an excess of dichloromethane, and washed several times with distilled water. After solvent removal, the produced solid was placed in a Hexane 2 l-containing vessel, washed, filtered, and dried, 2-(7-bromo-9,9-dimethyl-9H-fluorene-2-carbonyl)benzoic acid (23.2 g, yield 60%) was obtained.

$^1$H NMR: 1.66 (s, 6H), 7.28 (t, 2H), 7.47 (dd, 2H), 7.62 (t, 1H), 7.84 (t, 1H), 7.92 (m, 2H), 7.99 (s, 1H), 8.08 (s, 1H), 8.12 (d, 1H), 12.31 (s, 1H).

Synthesis Example 10

Preparation of 2-bromo-13,13-dimethyl-13H-indeno[1,2-b]anthracene-6,11-dione

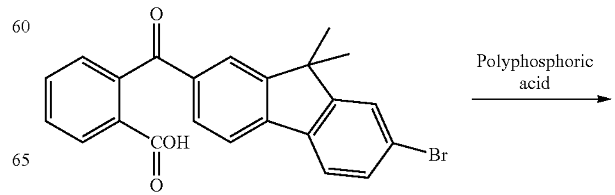

-continued

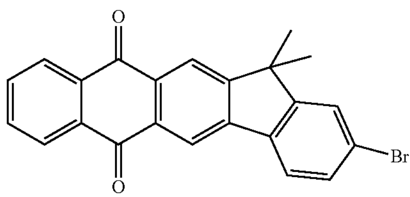

2-(7-bromo-9,9-dimethyl-9H-fluorene-2-carbonyl)benzoic acid (23.0 g, 0.055 mol) was placed in a flask, and polyphosphoric acid (80 ml) was added thereto. The reaction mixture was heated at 140° C. for 2 hours, and cooled to less than 50° C., and distilled water was gradually added thereto. The produced solid was filtered, washed with a small amount of methanol, and dried, 2-bromo-13,13-dimethyl-13H-indeno[1,2-b]anthracene-6,11-dione (16.0 g, yield 72%) was obtained.

$^1$H NMR: 1.64 (s, 6H), 7.13 (t, 1H), 7.23 (t, 1H), 7.51 (d, 2H), 7.67 (m, 2H), 7.97 (s, 1H), 8.09 (s, 1H), 8.21 (s, 1H).

Synthesis Example 11

Preparation of 2-bromo-13,13-dimethyl-13H-indeno[1,2-b]anthracene

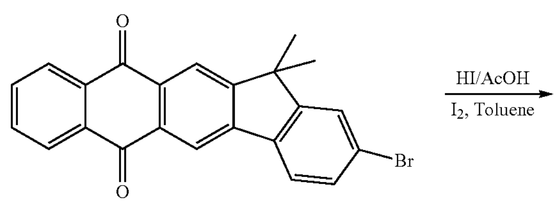

2-bromo-13,13-dimethyl-13H-indeno[1,2-b]anthracene-6,11-dione (20 g, 0.05 mol) was dissolved in acetic acid (200 ml), and added with 57% HI (50 ml), followed by reflux-stirring for 48 hours. After the reaction was completed, the resultant solution was added with distilled water (500 ml). The produced solid was filtered and dissolved in toluene (200 ml) and iodine (4.05 g, 0.016 mol) was added thereto, followed by reflux-stirring for 3 hours. After the reaction was completed, through extraction and column chromatography, 2-bromo-13,13-dimethyl-13H-indeno[1,2-b]anthracene (11.3 g, yield 61%) was obtained.

$^1$H NMR: 1.61 (s, 6H), 7.42 (dd, 2H), 7.54 (d, 1H), 7.73 (dd, 1H), 7.88 (d, 1H), 7.99 (dd, 2H), 8.05 (s, 1H), 8.37 (s, 1H), 8.45 (s, 1H), 8.50 (s, 1H); FD-MS: m/z 374 ($M^+$).

Synthesis Example 12

Preparation of 2,6,11-tribromo-13,13-dimethyl-13H-indeno[1,2-b]anthracene

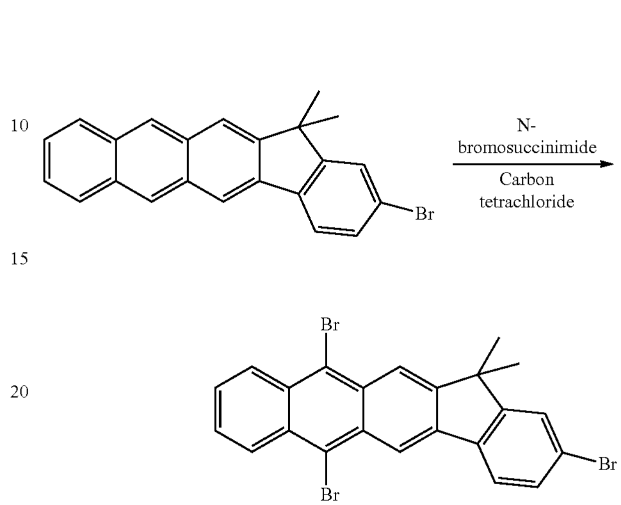

2-bromo-13,13-dimethyl-13H-indeno[1,2-b]anthracene (11 g, 0.03 mol) and N-bromosuccinimide 11.39 g (0.064 mol) were dissolved in carbon tetrachloride (200 ml), and stirred at 60° C., for 8 hours. After the reaction was completed, the resultant product was extracted with distilled water, and through column chromatography, 2,6,11-tribromo-13,13-dimethyl-13H-indeno[1,2-b]anthracene (11.5 g, yield 73%) was obtained.

$^1$H NMR: 1.67 (s, 6H), 7.61 (d, 1H), 7.68 (dd, 2H), 7.80 (s, 1H), 8.03 (d, 1H), 8.59 (dd, 2H), 8.64 (s, 1H), 8.95 (s, 1H); FD-MS: m/z 530 ($M^+$).

Example 64

Preparation of Inv-3-1

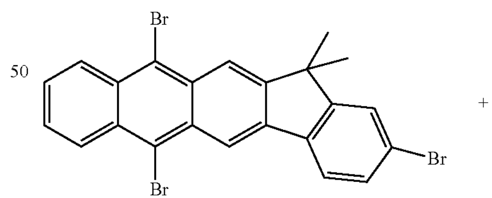

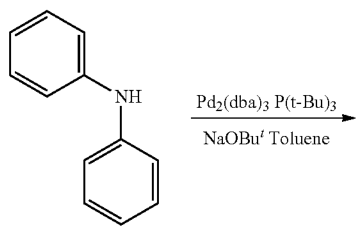

-continued

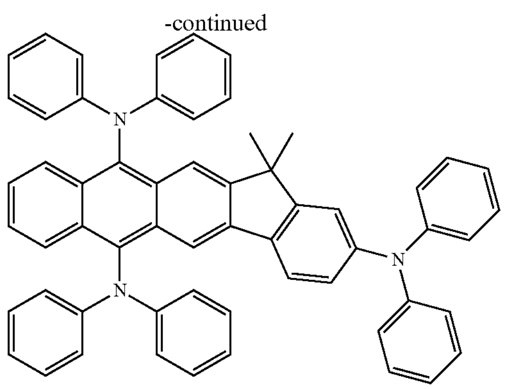

2,6,11-tribromo-13,13-dimethyl-13H-indeno[1,2-b]anthracene (5.0 g, 9.47 mmol), and diphenylamine (6.41 g, 37.9 mmol) were dissolved in toluene (300 mL), and tris benzylidene acetone dipalladium (0.26 g, 0.28 mmol) was added thereto under a nitrogen atmosphere. Then, $P(t\text{-}Bu)_3$ (0.38 g, 1.89 mmol) was added to the resultant mixture, and $NaOBu^t$ (3.64 g, 37.89 mmol) was added thereto. The resultant solution was reflux-stirred for hours. After the reaction was completed, the resultant solution was subjected to high temperature filtration through a thin silica pad so as to remove palladium. The filtrate was worked-up by EA and water, and the EA layer was dried by $MgSO_4$. The organic solvent layer was evaporated under a reduced pressure to remove almost all the solvent. Then, through filtration, a brown solid product was firstly obtained. The filtrate was dissolved in a small amount of methylene chloride, and re-crystallized by lowering the temperature. Then, the resultant product was filtered to gain a yellow solid (6.85 g, yield 91%).

$^1$H NMR: 1.62 (s, 6H), 6.45 (m, 12H), 7.05 (m, 18H), 7.36 (t, 1H), 7.49 (s, 1H), 7.62 (t, 1H), 7.79 (dd, 2H), 7.95 (t, 1H), 8.14 (s, 1H), 8.24 (t, 2H), 8.47 (s, 1H); FD-MS: m/z 795 ($M^+$).

Example 65

Preparation of Inv-3-4

2,6,11-tribromo-13,13-dimethyl-13H-indeno[1,2-b]anthracene (5.0 g, 9.47 mmol), and 4-isopropyl-N-p-tolylbenzenamine (8.53 g, 37.9 mmol) were dissolved in toluene 250 mL. Inv-3-4 (8.21 g, yield 90%) was obtained through the same synthesis method as described in Example 64. FD-MS: m/z 964 ($M^+$).

Example 66

Preparation of Inv-3-5

2,6,11-tribromo-13,13-dimethyl-13H-indeno[1,2-b]anthracene (5.0 g, 9.47 mmol), and bis(3,5-dimethylphenyl) amine (8.53 g, 37.9 mmol) were dissolved in toluene 250 mL. Inv-3-5 (8.39 g, yield 92%) was obtained through the same synthesis method as described in Example 64. FD-MS: m/z 964 ($M^+$).

Example 67

Preparation of Inv-3-7

2,6,11-tribromo-13,13-dimethyl-13H-indeno[1,2-b]anthracene (5.0 g, 9.47 mmol), and N-phenylnaphthalen-1-amine (8.30 g, 37.9 mmol) were dissolved in toluene 250 mL. Inv-3-7 (7.97 g, yield 89%) was obtained through the same synthesis method as described in Example 64. FD-MS: m/z 945 ($M^+$).

Example 68

Preparation of Inv-3-9

2,6,11-tribromo-13,13-dimethyl-13H-indeno[1,2-b]anthracene (5.0 g, 9.47 mmol), and N-(naphthalen-2-yl)naphthalen-1-amine (10.19 g, 37.9 mmol) were dissolved in toluene 250 mL. Inv-3-9 (8.91 g, yield 87%) was obtained through the same synthesis method as described in Example 64. FD-MS: m/z 1095 ($M^+$).

Example 69

Preparation of Inv-3-13

2,6,11-tribromo-13,13-dimethyl-13H-indeno[1,2-b]anthracene (5.0 g, 9.47 mmol), and N-(biphenyl-4-yl)naphthalen-2-amine (11.18 g, 37.9 mmol) were dissolved in toluene 250 mL. Inv-3-13 (9.11 g, yield 82%) was obtained through the same synthesis method as described in Example 64. FD-MS: m/z 1174 ($M^+$).

Example 70

Preparation of Inv-3-15

2,6,11-tribromo-13,13-dimethyl-13H-indeno[1,2-b]anthracene (5.0 g, 9.47 mmol), and 9,9-dimethyl-N-phenyl-9H-fluoren-2-amine (10.80 g, 37.9 mmol) were dissolved in toluene 250 mL. Inv-3-15 (9.10 g, yield 84%) was obtained through the same synthesis method as described in Example 64. FD-MS: m/z 1144 ($M^+$).

Example 71

Preparation of Inv-3-17

2,6,11-tribromo-13,13-dimethyl-13H-indeno[1,2-b]anthracene (5.0 g, 9.47 mmol), and bis(9,9-dimethyl-9H-fluoren-2-yl)amine (15.20 g, 37.9 mmol) were dissolved in toluene 250 mL. Inv-3-17 (11.30 g, yield 80%) was obtained through the same synthesis method as described in Example 64. FD-MS: m/z 1492 ($M^+$).

Example 72

Preparation of Inv-3-18

2,6,11-tribromo-13,13-dimethyl-13H-indeno[1,2-b]anthracene (5.0 g, 9.47 mmol), and N-phenylanthracene-2-amine (10.19 g, 37.9 mmol) were dissolved in toluene 250 mL. Inv-3-18 (8.10 g, yield 78%) was obtained through the same synthesis method as described in Example 64. FD-MS: m/z 1095 ($M^+$).

Example 73

Preparation of Inv-3-22

2,6,11-tribromo-13,13-dimethyl-13H-indeno[1,2-b]anthracene (5.0 g, 9.47 mmol), and N-phenyl-9,9'-spirobi[fluoren]-2-amine (15.42 g, 37.9 mmol) were dissolved in toluene 250 mL. Inv-3-22 (9.86 g, yield 69%) was obtained through the same synthesis method as described in Example 64. FD-MS: m/z 1510 ($M^+$).

Example 74

Preparation of Inv-3-30

2,6,11-tribromo-13,13-dimethyl-13H-indeno[1,2-b]anthracene (5.0 g, 9.47 mmol), and N-(biphenyl-3-yl)biphenyl-2-amine (12.17 g, 37.9 mmol) were dissolved in toluene 250 mL. Inv-3-30 (8.06 g, yield 68%) was obtained through the same synthesis method as described in Example 64. FD-MS: m/z 1252 ($M^+$).

Example 75

Preparation of Inv-3-33

2,6,11-tribromo-13,13-dimethyl-13H-indeno[1,2-b]anthracene (5.0 g, 9.47 mmol), and N-(4-isopropylphenyl)biphenyl-3-amine (10.88 g, 37.9 mmol) were dissolved in toluene 250 mL. Inv-3-33 (7.95 g, yield 73%) was obtained through the same synthesis method as described in Example 64. FD-MS: m/z 1150 ($M^+$).

Example 76

Preparation of Inv-3-41

2,6,11-tribromo-13,13-dimethyl-13H-indeno[1,2-b]anthracene (5.0 g, 9.47 mmol), and N-phenylthiophen-2-amine (6.63 g, 37.9 mmol) were dissolved in toluene 250 mL. Inv-3-41 (6.55 g, yield 85%) was obtained through the same synthesis method as described in Example 64. FD-MS: m/z 813 ($M^+$).

Example 77

Preparation of Inv-3-46

2,6,11-tribromo-13,13-dimethyl-13H-indeno[1,2-b]anthracene (5.0 g, 9.47 mmol), and N-(4-isopropylphenyl)thiophen-2-amine (8.22 g, 37.9 mmol) were dissolved in toluene 250 mL. Inv-3-46 (7.74 g, yield 87%) was obtained through the same synthesis method as described in Example 64. FD-MS: m/z 939 ($M^+$).

Example 78

Preparation of Inv-3-47

2,6,11-tribromo-13,13-dimethyl-13H-indeno[1,2-b]anthracene (5.0 g, 9.47 mmol), and N-phenylpyrazin-2-amine (6.48 g, 37.9 mmol) were dissolved in toluene 250 mL. Inv-3-47 (6.30 g, yield 83%) was obtained through the same synthesis method as described in Example 64. FD-MS: m/z 801 ($M^+$).

Example 79

Preparation of Inv-3-49

2,6,11-tribromo-13,13-dimethyl-13H-indeno[1,2-b]anthracene (5.0 g, 9.47 mmol), and N-(biphenyl-3-yl)pyrazin-2-amine (9.36 g, 37.9 mmol) were dissolved in toluene 250 mL. Inv-3-49 (7.70 g, yield 79%) was obtained through the same synthesis method as described in Example 64. FD-MS: m/z 1029 ($M^+$).

Example 80

Preparation of Inv-3-53

2,6,11-tribromo-13,13-dimethyl-13H-indeno[1,2-b]anthracene (5.0 g, 9.47 mmol), and N-phenylpyridin-2-amine (6.44 g, 37.9 mmol) were dissolved in toluene 250 mL. Inv-3-53 (6.65 g, yield 88%) was obtained through the same synthesis method as described in Example 64. FD-MS: m/z 798 ($M^+$).

Example 81

Preparation of Inv-3-54

2,6,11-tribromo-13,13-dimethyl-13H-indeno[1,2-b]anthracene (5.0 g, 9.47 mmol), and N-(biphenyl-4-yl)pyridin-2-amine (9.32 g, 37.9 mmol) were dissolved in toluene 250 mL. Inv-3-54 (7.78 g, yield 80%) was obtained through the same synthesis method as described in Example 64. FD-MS: m/z 1026 ($M^+$).

Example 82

Preparation of Inv-3-61

2,6,11-tribromo-13,13-dimethyl-13H-indeno[1,2-b]anthracene (5.0 g, 9.47 mmol), and N-(9,9-dimethyl-9H-fluoren-2-yl)pyridin-2-amine (10.84 g, 37.9 mmol) were dissolved in toluene 250 mL. Inv-3-61 (9.01 g, yield 83%) was obtained through the same synthesis method as described in Example 64. FD-MS: m/z 1147 ($M^+$).

Example 83

Preparation of Inv-3-64

2,6,11-tribromo-13,13-dimethyl-13H-indeno[1,2-b]anthracene (5.0 g, 9.47 mmol), and N-(naphthalen-2-yl)quinolin-6-amine (10.23 g, 37.9 mmol) were dissolved in toluene 250 mL. Inv-3-64 (8.11 g, yield 78%) was obtained through the same synthesis method as described in Example 64. FD-MS: m/z 1098 ($M^+$).

Example 84

Preparation of Inv-3-66

2,6,11-tribromo-13,13-dimethyl-13H-indeno[1,2-b]anthracene (5.0 g, 9.47 mmol), and N-(biphenyl-4-yl)quinolin-6-amine (11.22 g, 37.9 mmol) were dissolved in toluene 250 mL. Inv-3-66 (8.58 g, yield 77%) was obtained through the same synthesis method as described in Example 64. FD-MS: m/z 1177 ($M^+$).

Example 85

Preparation of Inv-3-72

2,6,11-tribromo-13,13-dimethyl-13H-indeno[1,2-b]anthracene (5.0 g, 9.47 mmol), and N-phenylisoquinolin-1-amine (8.34 g, 37.9 mmol) were dissolved in toluene 250 mL.

Inv-3-72 (7.19 g, yield 80%) was obtained through the same synthesis method as described in Example 64. FD-MS: m/z 948 ($M^+$).

Example 86

Preparation of Inv-3-74

2,6,11-tribromo-13,13-dimethyl-13H-indeno[1,2-b]anthracene (5.0 g, 9.47 mmol), and N-phenylisoquinolin-3-amine (8.34 g, 37.9 mmol) were dissolved in toluene 250 mL. Inv-3-74 (7.27 g, yield 81%) was obtained through the same synthesis method as described in Example 64. FD-MS: m/z 948 ($M^+$).

Example 87

Preparation of Inv-3-76

2,6,11-tribromo-13,13-dimethyl-13H-indeno[1,2-b]anthracene (5.0 g, 9.47 mmol), and 4-isopropyl-N-(4-methoxyphenyl)benzenamine (9.13 g, 37.9 mmol) were dissolved in toluene 250 mL. Inv-3-76 (8.05 g, yield 84%) was obtained through the same synthesis method as described in Example 64. FD-MS: m/z 1012 ($M^+$).

Example 88

Preparation of Inv-3-79

2,6,11-tribromo-13,13-dimethyl-13H-indeno[1,2-b]anthracene (5.0 g, 9.47 mmol), and dibenzylamine (7.47 g, 37.9 mmol) were dissolved in toluene 250 mL. Inv-3-79 (7.16 g, yield 86%) was obtained through the same synthesis method as described in Example 64. FD-MS: m/z 880 ($M^+$).

Synthesis Example 13

Preparation of 5-bromo-2-(7-bromo-9,9-dimethyl-9H-fluorene-2-carbonyl)benzoic acid

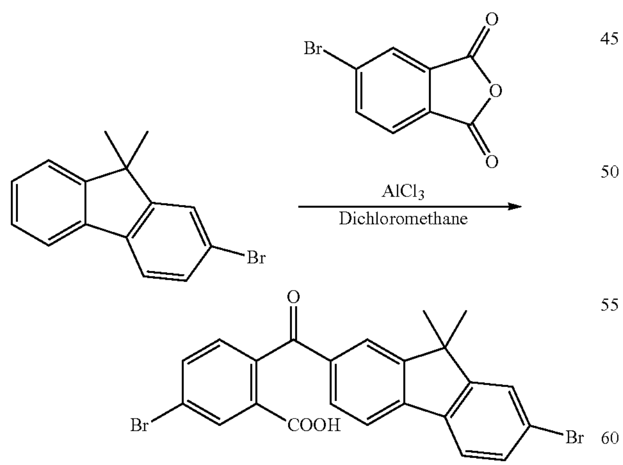

2-bromo-9,9-dimethyl-9H-fluorene (25.0 g, 0.092 mol) and 5-bromoisobenzofuran-1,3-dione (26.89 g, 0.119 mol) were placed in a reaction vessel, and added with dichloromethane (700 ml). At 0° C., aluminum chloride (18.5 g, 0.138 mol) was gradually added thereto, and the temperature was raised up to room temperature. Then, the resultant mixture was stirred for 12 hours. After the reaction was completed, the resultant product was gradually added with distilled water. The resultant product was extracted with an excess of dichloromethane, and washed several times with distilled water. After solvent removal, the produced solid was placed in a Hexane 2 l-containing vessel, washed, filtered, and dried, 5-bromo-2-(7-bromo-9,9-dimethyl-9H-fluorene-2-carbonyl)benzoic acid (27.9 g, yield 61%) was obtained.

$^1$H NMR: 1.62 (s, 6H), 7.28 (t, 1H), 7.41 (dd, 2H), 7.53 (s, 1H), 7.62 (t, 1H), 7.91 (d, 1H), 7.97 (s, 1H), 8.08 (s, 1H), 8.12 (d, 1H), 12.31 (s, 1H).

Synthesis Example 14

Preparation of 2,8-dibromo-13,13-dimethyl-13H-indeno[1,2-b]anthracene-6,11-dione

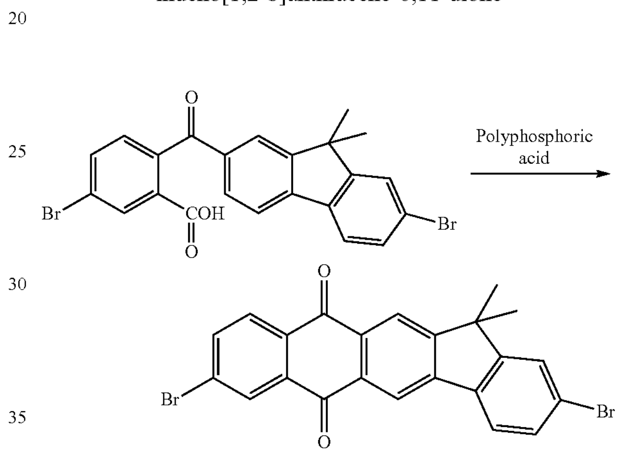

5-bromo-2-(7-bromo-9,9-dimethyl-9H-fluorene-2-carbonyl)benzoic acid (27.0 g, 0.054 mol) was placed in a flask, and polyphosphoric acid (100 ml) was added thereto. The reaction mixture was heated at 140° C. for 2 hours, and cooled to less than 50° C., and distilled water was gradually added thereto. The produced solid was filtered, washed with a small amount of methanol, and dried, 2,8-dibromo-13,13-dimethyl-13H-indeno[1,2-b]anthracene-6,11-dione (18.1 g, yield 70%) was obtained.

$^1$H NMR: 1.63 (s, 6H), 7.13 (s, 1H), 7.51 (d, 2H), 7.67 (m, 2H), 7.97 (s, 1H), 8.09 (s, 1H), 8.21 (s, 1H).

Synthesis Example 15

Preparation of 2,8-dibromo-13,13-dimethyl-13H-indeno[1,2-b]anthracene

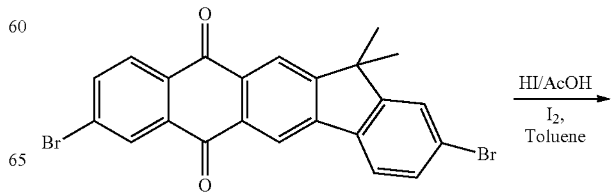

-continued

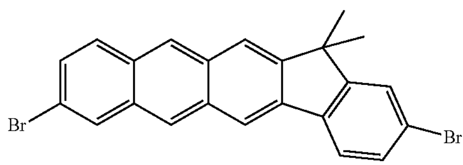

2,8-dibromo-13,13-dimethyl-13H-indeno[1,2-b]anthracene-6,11-dione (20 g, 0.04 mol) was dissolved in acetic acid (200 ml), and added with 57% HI (50 ml), followed by reflux-stirring for 48 hours. After the reaction was completed, the resultant solution was added with distilled water (500 ml). The produced solid was filtered and dissolved in toluene (200 ml) and iodine (4.05 g, 0.016 mol) was added thereto, followed by reflux-stirring for 3 hours. After the reaction was completed, through extraction and column chromatography, 2,8-dibromo-13,13-dimethyl-13H-indeno[1,2-b]anthracene (10.9 g, yield 59%) was obtained.

$^{1}$H NMR: 1.62 (s, 6H), 7.41 (dd, 1H), 7.51 (s, 1H), 7.76 (dd, 1H), 7.90 (d, 1H), 7.98 (dd, 2H), 8.12 (s, 1H), 8.37 (s, 1H), 8.42 (s, 1H), 8.55 (s, 1H); FD-MS: m/z 450 ($M^+$).

Synthesis Example 16

Preparation of 2,6,8,11-tetrabromo-13,13-dimethyl-13H-indeno[1,2-b]anthracene

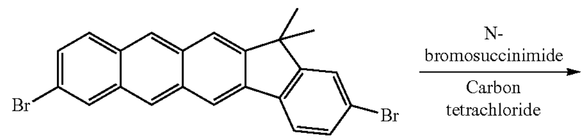

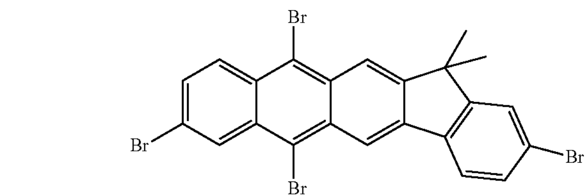

2,8-dibromo-13,13-dimethyl-13H-indeno[1,2-b]anthracene (10 g, 0.02 mol) and N-bromosuccinimide (8.90 g, 0.050 mol) were dissolved in carbon tetrachloride (200 ml), and stirred at 60° C., for 8 hours. After the reaction was completed, the resultant product was extracted with distilled water, and through column chromatography, 2,6,8,11-tetrabromo-13,13-dimethyl-13H-indeno[1,2-b]anthracene (10.3 g, yield 77%) was obtained.

$^{1}$H NMR: 1.62 (s, 6H), 7.58 (dd, 1H), 7.66 (dd, 2H), 7.88 (s, 1H), 8.01 (s, 1H), 8.52 (dd, 1H), 8.67 (s, 1H), 8.91 (s, 1H); FD-MS: m/z 606 ($M^+$).

Example 89

Preparation of Inv-4-1

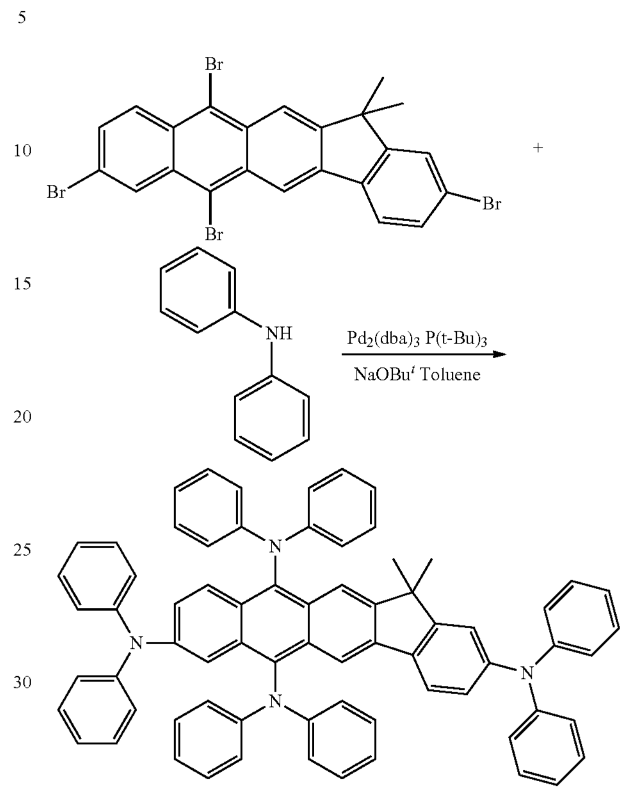

2,6,8,11-tetrabromo-13,13-dimethyl-13H-indeno[1,2-b]anthracene (5.0 g, 8.25 mmol), and diphenylamine (8.38 g, 49.5 mmol) were dissolved in toluene (300 mL), and tris benzylidene acetone dipalladium (0.30 g, 0.33 mmol) was added thereto under a nitrogen atmosphere. Then, $P(t\text{-}Bu)_3$ (0.50 g, 2.48 mmol) was added to the resultant mixture, and $NaOBu^t$ (4.76 g, 49.5 mmol) was added thereto. The resultant solution was reflux-stirred for hours. After the reaction was completed, the resultant solution was subjected to high temperature filtration through a thin silica pad so as to remove palladium. The filtrate was worked-up by EA and water, and the EA layer was dried by $MgSO_4$. The organic solvent layer was evaporated under a reduced pressure to remove almost all the solvent. Then, through filtration, a brown solid product was firstly obtained. The filtrate was dissolved in a small amount of methylene chloride, and re-crystallized by lowering the temperature. Then, the resultant product was filtered to gain a yellow solid (7.15 g, yield 90%).

$^{1}$H NMR: 1.63 (s, 6H), 6.38 (m, 16H), 7.05 (m, 24H), 7.55 (dd, 1H), 7.64 (dd, 2H), 7.85 (s, 1H), 7.99 (s, 1H), 8.48 (dd, 1H), 8.62 (s, 1H), 8.87 (s, 1H); FD-MS: m/z 962 ($M^+$).

Example 90

Preparation of Inv-4-3

2,6,8,11-tetrabromo-13,13-dimethyl-13H-indeno[1,2-b]anthracene (5.0 g, 8.25 mmol), and 4-tert-butyl-N-(4-isopropylphenyl)benzenamine (13.23 g, 49.5 mmol) were dissolved in toluene (300 mL). Inv-4-3 (6.48 g, yield 58%) was obtained through the same synthesis method as described in Example 89. FD-MS: m/z 1355 ($M^+$).

Example 91

Preparation of Inv-4-9

2,6,8,11-tetrabromo-13,13-dimethyl-13H-indeno[1,2-b] anthracene (5.0 g, 8.25 mmol), and N-(naphthalen-2-yl)naphthalen-1-amine (13.32 g, 49.5 mmol) were dissolved in toluene 300 mL. Inv-4-9 (6.07 g, yield 54%) was obtained through the same synthesis method as described in Example 89. FD-MS: m/z 1363 ($M^+$).

Example 92

Preparation of Inv-4-11

2,6,8,11-tetrabromo-13,13-dimethyl-13H-indeno[1,2-b] anthracene (5.0 g, 8.25 mmol), and dibiphenyl-4-ylamine (15.9 g, 49.5 mmol) were dissolved in toluene 300 mL. Inv-4-11 (6.48 g, yield 50%) was obtained through the same synthesis method as described in Example 89. FD-MS: m/z 1571 ($M^+$).

Example 93

Preparation of Inv-4-13

2,6,8,11-tetrabromo-13,13-dimethyl-13H-indeno[1,2-b] anthracene (5.0 g, 8.25 mmol), and N-(biphenyl-4-yl)naphthalen-2-amine (14.61 g, 49.5 mmol) were dissolved in toluene (300 mL). Inv-4-13 (6.17 g, yield 51%) was obtained through the same synthesis method as described in Example 89. FD-MS: m/z 1467 ($M^+$).

Example 94

Preparation of Inv-4-15

2,6,8,11-tetrabromo-13,13-dimethyl-13H-indeno[1,2-b] anthracene (5.0 g, 8.25 mmol), and 9,9-dimethyl-N-phenyl-9H-fluoren-2-amine (14.11 g, 49.5 mmol) were dissolved in toluene (300 mL). Inv-4-15 (6.24 g, yield 53%) was obtained through the same synthesis method as described in Example 89. FD-MS: m/z 1427 ($M^+$).

Example 95

Preparation of Inv-4-17

2,6,8,11-tetrabromo-13,13-dimethyl-13H-indeno[1,2-b] anthracene (5.0 g, 8.25 mmol), and bis(9,9-dimethyl-9H-fluoren-2-yl)amine (19.86 g, 49.5 mmol) were dissolved in toluene 300 mL. Inv-4-17 (7.49 g, yield 48%) was obtained through the same synthesis method as described in Example 89. FD-MS: m/z 1891 ($M^+$).

Example 96

Preparation of Inv-4-18

2,6,8,11-tetrabromo-13,13-dimethyl-13H-indeno[1,2-b] anthracene (5.0 g, 8.25 mmol), and N-phenylanthracene-2-amine (13.32 g, 49.5 mmol) were dissolved in toluene (300 mL). Inv-4-18 (5.28 g, yield 47%) was obtained through the same synthesis method as described in Example 89. FD-MS: m/z 1363 ($M^+$).

Example 97

Preparation of Inv-4-22

2,6,8,11-tetrabromo-13,13-dimethyl-13H-indeno[1,2-b] anthracene (5.0 g, 8.25 mmol), and N-phenyl-9,9'-spirobi [fluoren]-2-amine (20.15 g, 49.5 mmol) were dissolved in toluene 300 mL. Inv-4-22 (6.63 g, yield 42%) was obtained through the same synthesis method as described in Example 89. FD-MS: m/z 1915 ($M^+$).

Example 98

Preparation of Inv-4-28

2,6,8,11-tetrabromo-13,13-dimethyl-13H-indeno[1,2-b] anthracene (5.0 g, 8.25 mmol), and N-(4-isopropylphenyl) biphenyl-2-amine (14.21 g, 49.5 mmol) were dissolved in toluene (300 mL). Inv-4-28 (6.04 g, yield 51%) was obtained through the same synthesis method as described in Example 89. FD-MS: m/z 1435 ($M^+$).

Example 99

Preparation of Inv-4-40

2,6,8,11-tetrabromo-13,13-dimethyl-13H-indeno[1,2-b] anthracene (5.0 g, 8.25 mmol), and N-methylbenzenamine (5.30 g, 49.5 mmol) were dissolved in toluene (300 mL). Inv-4-40 (4.89 g, yield 83%) was obtained through the same synthesis method as described in Example 89. FD-MS: m/z 714 ($M^+$).

Example 100

Preparation of Inv-4-41

2,6,8,11-tetrabromo-13,13-dimethyl-13H-indeno[1,2-b] anthracene (5.0 g, 8.25 mmol), and N-phenylthiophen-2-amine (8.66 g, 49.5 mmol) were dissolved in toluene (300 mL). Inv-4-41 (6.35 g, yield 78%) was obtained through the same synthesis method as described in Example 89. FD-MS: m/z 986 ($M^+$).

Example 101

Preparation of Inv-4-43

2,6,8,11-tetrabromo-13,13-dimethyl-13H-indeno[1,2-b] anthracene (5.0 g, 8.25 mmol), and N-(biphenyl-3-yl) thiophen-2-amine (12.43 g, 49.5 mmol) were dissolved in toluene (300 mL). Inv-4-43 (6.28 g, yield 59%) was obtained through the same synthesis method as described in Example 89. FD-MS: m/z 1290 ($M^+$).

Example 102

Preparation of Inv-4-47

2,6,8,11-tetrabromo-13,13-dimethyl-13H-indeno[1,2-b] anthracene (5.0 g, 8.25 mmol), and N-phenylpyrazin-2-amine (8.47 g, 49.5 mmol) were dissolved in toluene (300 mL). Inv-4-47 (5.92 g, yield 74%) was obtained through the same synthesis method as described in Example 89. FD-MS: m/z 970 ($M^+$).

Example 103

Preparation of Inv-4-52

2,6,8,11-tetrabromo-13,13-dimethyl-13H-indeno[1,2-b] anthracene (5.0 g, 8.25 mmol), and N-(4-isopropylphenyl) pyrazin-2-amine (10.55 g, 49.5 mmol) were dissolved in toluene (300 mL). Inv-4-52 (6.48 g, yield 69%) was obtained through the same synthesis method as described in Example 89. FD-MS: m/z 1139 ($M^+$).

Example 104

Preparation of Inv-4-53

2,6,8,11-tetrabromo-13,13-dimethyl-13H-indeno[1,2-b] anthracene (5.0 g, 8.25 mmol), and N-phenylpyridin-2-amine (8.42 g, 49.5 mmol) were dissolved in toluene (300 mL). Inv-4-53 (6.54 g, yield 82%) was obtained through the same synthesis method as described in Example 89. FD-MS: m/z 967 ($M^+$).

Example 105

Preparation of Inv-4-58

2,6,8,11-tetrabromo-13,13-dimethyl-13H-indeno[1,2-b] anthracene (5.0 g, 8.25 mmol), and N-(4-isopropylphenyl) pyridin-2-amine (10.50 g, 49.5 mmol) were dissolved in toluene (300 mL). Inv-4-58 (7.49 g, yield 80%) was obtained through the same synthesis method as described in Example 89. FD-MS: m/z 1135 ($M^+$).

Example 106

Preparation of Inv-4-60

2,6,8,11-tetrabromo-13,13-dimethyl-13H-indeno[1,2-b] anthracene (5.0 g, 8.25 mmol), and N-(naphthalen-1-yl)pyridin-2-amine (10.89 g, 49.5 mmol) were dissolved in toluene (300 mL). Inv-4-60 (7.03 g, yield 73%) was obtained through the same synthesis method as described in Example 89. FD-MS: m/z 1167 ($M^+$).

Example 107

Preparation of Inv-4-61

2,6,8,11-tetrabromo-13,13-dimethyl-13H-indeno[1,2-b] anthracene (5.0 g, 8.25 mmol), and N-(9,9-dimethyl-9H-fluoren-2-yl)pyridin-2-amine (14.16 g, 49.5 mmol) were dissolved in toluene (300 mL). Inv-4-61 (8.14 g, yield 69%) was obtained through the same synthesis method as described in Example 89. FD-MS: m/z 1431 ($M^+$).

Example 108

Preparation of Inv-4-63

2,6,8,11-tetrabromo-13,13-dimethyl-13H-indeno[1,2-b] anthracene (5.0 g, 8.25 mmol), and N-phenylquinolin-6-amine (10.89 g, 49.5 mmol) were dissolved in toluene (300 mL). Inv-4-63 (6.93 g, yield 72%) was obtained through the same synthesis method as described in Example 89. FD-MS: m/z 1167 ($M^+$).

Example 109

Preparation of Inv-4-69

2,6,8,11-tetrabromo-13,13-dimethyl-13H-indeno[1,2-b] anthracene (5.0 g, 8.25 mmol), and N-phenylisoquinolin-4-amine (10.89 g, 49.5 mmol) were dissolved in toluene (300 mL). Inv-4-69 (7.03 g, yield 73%) was obtained through the same synthesis method as described in Example 89. FD-MS: m/z 1167 ($M^+$).

Example 110

Preparation of Inv-4-72

2,6,8,11-tetrabromo-13,13-dimethyl-13H-indeno[1,2-b] anthracene (5.0 g, 8.25 mmol), and N-phenylisoquinolin-1-amine (10.89 g, 49.5 mmol) were dissolved in toluene (300 mL). Inv-4-72 (7.22 g, yield 75%) was obtained through the same synthesis method as described in Example 89. FD-MS: m/z 1167 ($M^+$).

Example 111

Preparation of Inv-4-77

2,6,8,11-tetrabromo-13,13-dimethyl-13H-indeno[1,2-b] anthracene (5.0 g, 8.25 mmol), and 2-methoxy-N-phenylbenzenamine (9.86 g, 49.5 mmol) were dissolved in toluene (300 mL). Inv-4-77 (7.23 g, yield 81%) was obtained through the same synthesis method as described in Example 89. FD-MS: m/z 1083 ($M^+$).

Example 112

Preparation of Inv-4-79

2,6,8,11-tetrabromo-13,13-dimethyl-13H-indeno[1,2-b] anthracene (5.0 g, 8.25 mmol), and dibenzylamine (9.76 g, 49.5 mmol) were dissolve din toluene (300 mL). Inv-4-(7.36 g, yield 83%) was obtained through the same synthesis method as described in Example 89. FD-MS: m/z 1075 ($M^+$).

Fabrication Example

Fabrication of an Organic Electro-Luminescence Device

Each of the products synthesized in Examples was used as a green dopant material to fabricate the organic electro-luminescence device as noted in Table 1. The test result on the fabricated device is noted in Tables 2 and 3.

The organic electro-luminescence device was manufactured as follows.

On the ITO (anode), DS-205 (Doosan) was thermal/vacuum-deposited to a thickness of 800 Å so as to form a hole injection layer, and α-NPB (N,N'-di(naphthalene-1-yl)-N,N'-diphenyl-benzidine) as a hole transport material was vacuum-deposited to a thickness of 300 Å on the hole injection layer to form a hole transport layer.

On the hole transport layer, the compound from Examples 1 to 112, as a green dopant material, and DS-H522 (Doosan), as a green light-emitting host material were vacuum-deposited to a thickness of 300 so as to form a light emitting layer. On the light emitting layer, tris-8-hydroquinoline aluminum (Alq3) as an electron transport material was vacuum-deposited to a thickness of 350 so as to form an electron transport layer. On the electron transport layer, LiF as an electron injection material was deposited to a thickness of 10 to form an electron injection layer, and then on the electron injection layer, aluminum was vacuum-deposited to a thickness of 2000 to form a cathode.

Comparative Example

Fabrication of an Organic Electro-Luminescence Device

An organic electro-luminescence device was fabricated in the same manner as described in Fabrication Example except that Alq3 and C-545T (representative system for a Green device), instead of the compound from Examples 1 to 112, and DS-H522 (Doosan), were used in the formation of the light emitting layer. The test result on the fabricated device is noted in Table 3.

TABLE 1

| | Hole injection layer (HIL) | Hole transport layer (HTL) | Organic light emitting layer (EML) | Electron transport layer (ETL) | Electron injection layer (EIL) | Cathode |
|---|---|---|---|---|---|---|
| Fabrication Example | DS-205 | a-NPB | DS- H522 + Inv-x | Alq3 | LiF | Al |
| Comparative Example | DS-205 | a-NPB | Alq3 + C-545T | Alq3 | LiF | Al |
| Thickness | 800 Å | 300 Å | 290 + 10 Å | 350 Å | 10 Å | 2000 Å |

TABLE 2

| Compounds | Current Density (mA/cm2) | Voltage (V) | Luminance (cd/m2) | Efficiency (cd/A) | Color |
|---|---|---|---|---|---|
| Inv-1-1 | 10 | 6.7 | 949 | 9.5 | Blueish Green |
| Inv-1-3 | 10 | 6.9 | 1054 | 10.5 | Green |
| Inv-1-6 | 10 | 6.6 | 986 | 9.9 | Green |
| Inv-1-9 | 10 | 6.8 | 1024 | 10.2 | Green |
| Inv-1-11 | 10 | 7 | 1013 | 10.1 | Green |
| Inv-1-15 | 10 | 6.5 | 1022 | 10.2 | Green |
| Inv-1-17 | 10 | 6.9 | 1123 | 11.2 | Green |
| Inv-1-18 | 10 | 7.2 | 1215 | 12.2 | Green |
| Inv-1-22 | 10 | 6.9 | 1170 | 11.7 | Green |
| Inv-1-26 | 10 | 6.6 | 1054 | 10.5 | Green |
| Inv-1-35 | 10 | 6.8 | 953 | 9.5 | Blueish Green |
| Inv-1-42 | 10 | 6.4 | 985 | 9.9 | Green |
| Inv-1-47 | 10 | 6.8 | 956 | 8.6 | Blueish Green |
| Inv-1-53 | 10 | 7.1 | 1055 | 10.6 | Green |
| Inv-1-59 | 10 | 6.5 | 1043 | 10.4 | Green |
| Inv-1-63 | 10 | 6.9 | 932 | 9.3 | Blueish Green |
| Inv-1-78 | 10 | 6.3 | 869 | 8.7 | Blueish Green |
| Inv-1-79 | 10 | 6.5 | 765 | 7.7 | Blueish Green |

TABLE 3

| Compounds | Current Density (mA/cm2) | Voltage (V) | Luminance (cd/m2) | Efficiency (cd/A) | Color |
|---|---|---|---|---|---|
| Inv-2-1 | 10 | 6.7 | 986 | 9.9 | Green |
| Inv-2-3 | 10 | 6.8 | 1132 | 11.3 | Green |
| Inv-2-5 | 10 | 6.7 | 1054 | 10.5 | Green |
| Inv-2-10 | 10 | 6.9 | 1122 | 11.2 | Green |
| Inv-2-11 | 10 | 6.7 | 1073 | 10.7 | Green |
| Inv-2-16 | 10 | 6.4 | 1116 | 11.2 | Green |
| Inv-2-23 | 10 | 7.1 | 1006 | 10.1 | Green |
| Inv-2-28 | 10 | 6.5 | 972 | 9.7 | Green |
| Inv-2-42 | 10 | 6.9 | 952 | 9.5 | Green |
| Inv-2-49 | 10 | 6.7 | 1086 | 10.9 | Green |
| Inv-2-61 | 10 | 6.8 | 996 | 10 | Green |
| Inv-3-1 | 10 | 6.8 | 994 | 9.9 | Green |
| Inv-3-4 | 10 | 6.7 | 1035 | 10.4 | Green |
| Inv-3-9 | 10 | 6.9 | 1137 | 11.4 | Green |
| Inv-3-18 | 10 | 7.1 | 1095 | 11 | Green |
| Inv-3-22 | 10 | 7.1 | 1024 | 10.2 | Green |
| Inv-3-33 | 10 | 6.7 | 988 | 9.9 | Green |
| Inv-3-46 | 10 | 6.6 | 962 | 9.6 | Green |
| Inv-3-53 | 10 | 6.4 | 986 | 9.9 | Green |
| Inv-3-64 | 10 | 6.9 | 1174 | 11.7 | Green |
| Inv-3-72 | 10 | 6.8 | 995 | 10 | Green |
| Inv-3-76 | 10 | 6.9 | 984 | 9.8 | Green |
| Inv-3-79 | 10 | 6.7 | 965 | 9.7 | Green |
| Inv-4-1 | 10 | 6.9 | 1058 | 10.6 | Green |
| Inv-4-13 | 10 | 6.9 | 1074 | 10.7 | Orange |
| Inv-4-17 | 10 | 7.1 | 1286 | 12.9 | Orange |
| Comp. Exp | 10 | 6.9 | 953 | 9.5 | Green |

As described above, the organic electro-luminescence device (Fabrication Example) using the present invention compound showed a higher performance in view of voltage and efficiency, as compared to the organic electro-luminescence device (Comparative Example) using conventional C545T.

Although a preferred embodiment of the present invention has been described for illustrative purposes, those skilled in the art will appreciate that various modifications, additions and substitutions are possible, without departing from the scope and spirit of the invention as disclosed in the accompanying claims.

INDUSTRIAL APPLICABILITY

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A compound of Formula 1 below

Formula 1

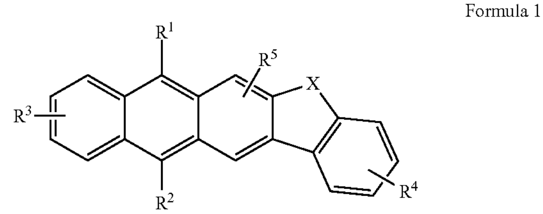

X is $CR^6R^7$, or $S(=O)_2$, $R^1$ to $R^7$ are the same or different, and each is independently selected from the group consisting of hydrogen, deuterium, an alkyl group of $C_1$~$C_{40}$, an alkenyl group of $C_2$~$C_{40}$, an alkynyl group of $C_2$~$C_{40}$, an aryl group of $C_5$~$C_{40}$, a heteroaryl group of $C_5$~$C_{40}$, an aryloxy group of $C_5$~$C_{40}$, an alkyloxy group of $C_1$~$C_{40}$, an arylalkyl group of $C_6$~$C_{40}$, a cycloalkyl group of $C_3$~$C_{40}$, a heterocycloalkyl group of $C_3$~$C_{40}$ and a substituent of Formula 2 below; or a group binding with an adjacent group to form a fused aliphatic ring, a fused aromatic ring, a fused heteroaliphatic ring or a fused heteroaromatic ring;

wherein, one or three or four of $R^1$ to $R^4$ is a substituent of Formula 2 below, Formula 2

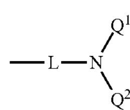

$Q^1$ and $Q^2$ are the same or different, and each is independently selected from the group consisting of hydrogen, deuterium, an alkyl group of $C_1$~$C_{40}$, an alkenyl group of $C_2$~$C_{40}$, an alkynyl group of $C_2$~$C_{40}$, an aryl group of $C_5$~$C_{40}$, a heteroaryl group of $C_5$~$C_{40}$, an aryloxy group of $C_5$~$C_{40}$, an alkyloxy group of $C_1$~$C_{40}$, an arylalkyl group of $C_6$~$C_{40}$, a cycloalkyl group of $C_3$~$C_{40}$, and a heterocycloalkyl group of $C_3$~$C_{40}$; or a group binding with an adjacent group to form a fused aliphatic ring, a fused aromatic ring, a fused heteroaliphatic ring or a fused heteroaromatic ring;

L is selected from the group consisting of a single bond, an alkylene group of $C_1$~$C_{40}$, an alkenylene group of $C_2$~$C_{40}$, an alkynylene group of $C_2$~$C_{40}$, an arylene group of $C_5$~$C_{40}$, a heteroarylene group of $C_5$~$C_{40}$, an aryloxy group of $C_5$~$C_{40}$, an alkyloxy group of $C_1$~$C_{40}$, an arylalkylene group of $C_6$~$C_{40}$, a cycloalkylene group of $C_3$~$C_{40}$, and a heterocycloalkylene group of $C_3$~$C_{40}$.

2. The compound as claimed in claim 1, wherein $R^1$ to $R^7$ and, $Q^1$ and $Q^2$, the alkyl group of $C_1$~$C_{40}$, the alkenyl group of $C_2$~$C_{40}$, the alkynyl group of $C_2$~$C_{40}$, the aryl group of $C_5$~$C_{40}$, the heteroaryl group of $C_5$~$C_{40}$, the aryloxy group of $C_5$~$C_{40}$, the alkyloxy group of $C_1$~$C_{40}$, the arylamino group of $C_5$~$C_{40}$, the diarylamino group of $C_5$~$C_{40}$, the arylalkyl group of $C_6$~$C_{40}$, the cycloalkyl group of $C_3$~$C_{40}$, and the heterocycloalkyl group of $C_3$~$C_{40}$ are each independently unsubstituted or substituted by at least one substituent selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$, and a heteroaryl group of $C_5$~$C_{40}$.

3. An organic electro-luminescence device comprising (i) an anode; (ii) a cathode; and (iii) one or more organic material layers intervened between the anode and the cathode, wherein at least one layer of the organic material layers comprises the compound of Formula 1 as claimed in claim 1.

4. The organic electro-luminescence device as claimed in claim 3, wherein the organic material layer comprising the compound of Formula 1 is a light emitting layer.

5. The organic electro-luminescence device as claimed in claim 3, wherein $R^1$ to $R^7$ and, $Q^1$ and $Q^2$ of the compound of Formula 1, the alkyl group of $C_1$~$C_{40}$, the alkenyl group of $C_2$~$C_{40}$, the alkynyl group of $C_2$~$C_{40}$, the aryl group of $C_5$~$C_{40}$, the heteroaryl group of $C_5$~$C_{40}$, the aryloxy group of $C_5$~$C_{40}$, the alkyloxy group of $C_1$~$C_{40}$, the arylamino group of $C_5$~$C_{40}$, the diarylamino group of $C_5$~$C_{40}$, the arylalkyl group of $C_6$~$C_{40}$, the cycloalkyl group of $C_3$~$C_{40}$, and the heterocycloalkyl group of $C_3$~$C_{40}$ are each independently unsubstituted or substituted by at least one substituent selected from the group consisting of deuterium, halogen, nitrile, nitro, an alkyl group of $C_1$~$C_{40}$, an alkenyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an aryl group of $C_6$~$C_{40}$, and a heteroaryl group of $C_5$~$C_{40}$.

* * * * *